United States Patent
Strober et al.

(10) Patent No.: US 11,020,428 B2
(45) Date of Patent: *Jun. 1, 2021

(54) COMBINED ORGAN AND HEMATOPOIETIC CELLS FOR TRANSPLANTATION TOLERANCE OF GRAFTS

(71) Applicant: The Board of Trustees of the Leland Stanford Junior University, Stanford, CA (US)

(72) Inventors: Samuel Strober, Stanford, CA (US); Robert Lowsky, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 16/196,806

(22) Filed: Nov. 20, 2018

(65) Prior Publication Data

US 2019/0083530 A1 Mar. 21, 2019

Related U.S. Application Data

(63) Continuation of application No. 15/914,736, filed on Mar. 7, 2018, now Pat. No. 10,159,694, which is a continuation of application No. 15/387,292, filed on Dec. 21, 2016, now Pat. No. 9,974,807, which is a continuation of application No. 14/438,159, filed as application No. PCT/US2014/015394 on Feb. 7, 2014, now Pat. No. 9,561,253.

(60) Provisional application No. 61/769,596, filed on Feb. 26, 2013.

(51) Int. Cl.
| | |
|---|---|
| *A61K 35/17* | (2015.01) |
| *A61K 35/12* | (2015.01) |
| *A61K 35/28* | (2015.01) |
| *A61K 35/22* | (2015.01) |
| *A61K 35/14* | (2015.01) |
| *A61K 38/19* | (2006.01) |
| *A61K 41/00* | (2020.01) |
| *A61K 45/06* | (2006.01) |
| *A61K 31/365* | (2006.01) |
| *A61K 31/436* | (2006.01) |
| *A61K 31/573* | (2006.01) |
| *A61K 38/13* | (2006.01) |
| *A61K 39/00* | (2006.01) |
| *A61K 39/395* | (2006.01) |
| *A61N 5/10* | (2006.01) |

(52) U.S. Cl.
CPC .......... *A61K 35/12* (2013.01); *A61K 31/365* (2013.01); *A61K 31/436* (2013.01); *A61K 31/573* (2013.01); *A61K 35/14* (2013.01); *A61K 35/17* (2013.01); *A61K 35/22* (2013.01); *A61K 35/28* (2013.01); *A61K 38/13* (2013.01); *A61K 38/193* (2013.01); *A61K 39/001* (2013.01); *A61K 39/39541* (2013.01); *A61K 41/00* (2013.01); *A61K 45/06* (2013.01); *A61N 5/10* (2013.01); *A61K 39/395* (2013.01); *A61K 2035/122* (2013.01); *A61K 2035/124* (2013.01); *A61K 2039/515* (2013.01); *A61K 2039/54* (2013.01); *A61K 2039/57* (2013.01)

(58) Field of Classification Search
None
See application file for complete search history.

(56) References Cited

U.S. PATENT DOCUMENTS

| | | |
|---|---|---|
| 6,558,662 B2 | 5/2003 | Sykes et al. |
| 6,877,514 B2 | 4/2005 | Sykes et al. |
| 7,332,157 B2 | 2/2008 | Skyes et al. |
| 7,638,121 B2 | 12/2009 | Skyes et al. |
| 7,811,815 B2 | 10/2010 | Brown et al. |
| 7,939,062 B2 | 5/2011 | Skyes et al. |
| 8,277,811 B2 | 10/2012 | Zeng et al. |
| 8,916,147 B2 | 12/2014 | Reisner |
| 8,980,329 B2 | 3/2015 | Brown et al. |
| 9,504,717 B2 | 11/2016 | Strober et al. |
| 9,545,427 B2 | 1/2017 | Brown et al. |
| 9,561,253 B2 | 2/2017 | Strober et al. |
| 2002/0042370 A1 | 4/2002 | Hancock et al. |
| 2003/0099622 A1 | 5/2003 | Hering et al. |
| 2009/0232774 A1 | 9/2009 | Reisner et al. |
| 2011/0110909 A1 | 5/2011 | Ildstad et al. |

(Continued)

FOREIGN PATENT DOCUMENTS

| | | |
|---|---|---|
| WO | 9939727 | 8/1999 |
| WO | 2002/040640 A2 | 5/2002 |

(Continued)

OTHER PUBLICATIONS

Nakamura R et al. (2001) "Transplant dose of CD34+ and CD3+ cells predicts outcome inpatients with haematological malignancies undergoing Tcell-depleted peripheral blood stem cell transplants with delayed donor lymphocyte add-back", British Journal of Haematology, vol. 115, pp. 95-1004.

(Continued)

*Primary Examiner* — Michail A Belyavskyi
(74) *Attorney, Agent, or Firm* — Pamela J. Sherwood; Bozicevic, Field & Francis LLP

(57) ABSTRACT

Methods and compositions are provided for combined transplantation of a solid organ and hematopoietic cells to a recipient, where tolerance to the graft is established through development of a persistent mixed chimerism. An individual with persistent mixed chimerism, usually for a period of at least six months, is able to withdraw from the use of immunosuppressive drugs after a period of time sufficient to establish tolerance.

10 Claims, 4 Drawing Sheets

(56) References Cited

U.S. PATENT DOCUMENTS

| | | | |
|---|---|---|---|
| 2012/0177621 | A1 | 7/2012 | Strober et al. |
| 2012/0329668 | A1 | 12/2012 | Sarwal et al. |
| 2015/0017130 | A1 | 1/2015 | Yang et al. |
| 2017/0106086 | A1 | 4/2017 | Strober et al. |

FOREIGN PATENT DOCUMENTS

| | | |
|---|---|---|
| WO | 2002083187 | 10/2002 |
| WO | 2003/012060 A2 | 2/2003 |
| WO | 2006133450 | 12/2006 |
| WO | 2011/068829 A1 | 6/2011 |
| WO | 2012/024427 A2 | 2/2012 |
| WO | 2012/096974 A1 | 7/2012 |
| WO | 2014/133729 A1 | 9/2014 |

OTHER PUBLICATIONS

Arbab et al. "Efficient magnetic cell labeling with protamine sulfate complexed to ferumoxides for cellular MRI" Blood, Aug. 15, 2004, pp. 1-22, 104(4), American Society of Hematology, Washington, D.C.
Beelen et al., "Transplantation of highly purified HLA-identical sibling donor peripheral blood CD34+ cells without prophylactic post-transplant immunosuppression in adult patients with first chronic phase chronic myeloid leukemia: results of a phase II study", Bone Marrow Transplantation, Oct. 16, 2000, pp. 823-829, 26, Macmillan Publishers Ltd., Basingstoke, United Kingdom.
European Search Report dated Dec. 21, 2015 for EP Application No. 14756899.2.
International Search Report dated May 6, 2014 for International Application No. PCT/US2014/015394.
June et al. "Adoptive T cell therapy for cancer in clinic" J Clin Invest., Jun. 1, 2007, pp. 1466-1476, 117(6), American Society for Clinical Investigation, Ann Arbor, MI.
Kalwak et al., "Higher CD341 and CD31 Cell Doses in the Graft Promote Long-Term Survival, and Have No Impact on the Incidence of Severe Acute or Chronic Graft-versus-Host Disease after In Vivo T Cell-Depleted Unrelated Donor Hematopoietic Stem Cell Transplantation in Children", Biol Blood Marrow Transplant, 2010, pp. 1388-1401, 16, Elsevier Inc., Amsterdam, Netherlands.
Kawai et al. ""HLA-mismatched Renal Transplantation without Maintenance Immunosuppression"" The New EnglandJournal of Medicine, Jan. 24, 2008, pp. 353-361, 358(4), Massachusetts Medical Society, Waltham, MA.
Kohrt et aL, ""TLI and ATG Conditioning with Low Risk of Graft-Versus-Host Disease Retains Antitumor Reactionsafter Allogeneic Hematopoietic Cell Transplantation from Related and Unrelated Donors"", Blood,Jul. 30, 2009 (Jul. 30, 2009), pp. 1099-1109, vol. 114, No. 5, The American Society of Hematology, Washington,DC.
Ledford, "Organ Transplant without Rejection", Nature, Jan. 23, 2008, pp. 1-3, Macmillan Publishers Ltd., Basingstoke, United Kingdom.
Leventhal et al. "Chimerism and tolerance without GVHD or engraftment syndrome in HLA-mismatched combined kidney and hematopoietic stem cell transplantation" Sci Transl Med., Mar. 7, 2012, pp. 1-22, 4(124), AAAS, Washington, DC.
Leventhal et al. "Tolerance Induction in HLA Disparate Living Donor Kidney Transplantation by Donor Stem CellInfusion: durable chimerism predicts outcome" Transplantation, Jan. 15, 2013 pp. 169-176, 95(1), LippincottWilliams & Wilkins, Philadelphia, PA.
Millan et al., ""Mixed chimerism and immunosuppressive drug withdrawal after HLA-mismatched kidney andnematopoietic progenitor transplantation"", Transplantation, May 2002, pp. 1386-1391, vol. 73, Lippincott Williams &Wilkins, Philadelphia, PA.
Notice of Allowance dated Sep. 16, 2016 for U.S. Appl. No. 14/175,832.
Notice of Allowance dated Dec. 2, 2016 for U.S. Appl. No. 14/438,159.
Office Action dated Feb. 23, 2016 for U.S. Appl. No. 14/175,832.
Office Action dated Mar. 4, 2016 for U.S. Appl. No. 14/438,159.
Office Action dated Jun. 14, 2016 for U.S. Appl. No. 14/438,159.
Office Action dated Oct. 12, 2016 for U.S. Appl. No. 14/438,159.
Perez-Pujol et al., "Proteomic analysis of gray platelet syndrome by iTRAQ Labelling and mass spetroscopy: a potential new diagnostic strategy for platelet disorders", Blood, (ASH Annual Meeting Abstracts), 2005, vol. 106, Issue: 11, p. 2161, Abstract, The American Society of Hematology, Washington, D.C.
Scandling et al. "Tolerance and withdrawal of immunosuppressive drugs in patients given kidney and hematopoietic cell transplants" Am J Transplant, May 2012, pp. 1133-1145, vol. 12, Issue 5, Wiley, Hoboken, NJ.
Scandling et al., ""Chimerism, Graft Survival, and Withdrawal of Immunosuppressive Drugs in HLA Matchedand Mismatched Patients After Living Donor Kidney and Hematopoietic Cell Transplantation"", American Journal ofTransplantation, 2015, pp. 695-704,15, Wiley Periodicals Inc., Hoboken, NJ.
Scandling et al., "Tolerance and Chimerism after Renal and Hematopoietic-Cell Transplantation", N Engl J Med., Jan. 24, 2008, pp. 362-368, 358, Massachusetts Medical Society, Waltham, MA.
Stanford University Medical Center. ""Stanford Team Prevents Kidney Transplant Rejection Without Drugs."" ScienceDaily, Apr. 24, 2002, pp. 1-3, downloaded from www.sciencedaily.com/releases/2002/04/020424072642.htm, ScienceDaily, Rockville, MD.
Strober et al. ""Translational studies in hematopoietic cell transplantation: treatment of hematologic malignancies as a stepping stone to tolerance induction"", Semin Immunol., Aug. 2011, pp. 273-281, vol. 23, Issue 4, Elsevier, Amsterdam, Netherlands.
Szabolcs et al. ""Tolerance after solid organ and hematopoietic cell transplantation"", Biol Blood Marrow Transplant, Jan. 2012, pp. S193-S200, vol. 18, Issue 1, Supplement, Elsevier, Amsterdam, Netherlands.
Urbano-Ispizua et al., "The number of donor CD31 cells is the most important factor for graft failure after allogeneic transplantation of CD341 selected cells from peripheral blood from HLA-identical siblings", Blood, Jan. 15, 2001, pp. 383-387, vol. 97, No. 2, The American Society of Hematology, Washington, D.C.
Collins et al., "The Effect of the Composition of Unrelated Donor Bone Marrow and Peripheral Blood Progenitor Cell Grafts on Transplantation Outcomes", Bioi Blood Marrow Transplant, Feb. 2010, pp. 253-262, vol. 16, Issue 2, Elsevier, New York City, NY.
Matthias et al., "Faster Engraftment and Immune Reconstitution after Haploidentical Allogenic Hematopoietic Cell Transplantation with CD3/CD19 Depleted as Compared to CD34 Selected Grafts", Blood, 2005, p. 220, vol. 106, Issue 11, American Society of Hematology, Washington, DC.
Pecheux et al., "Impact of Graft CD34 Cell Dose on Chronic Graft-Versus-Host Disease (cGVHD) and Predictive Values of CD3 Cell Dose and Day 56 Chimerism on Survival in Nonmyeloablative (NMA) Allogeneic Hematopoietic Stem Cell Transplant (HSCT)", Biology of Blood and Marrow Transplantation, Feb. 2012, pp. S262-S263, vol. 18, Issue 2, Supplement, Elsevier, New York City, NY.
Prebet et al., "mpact of Hematopoietic Stem Cell (HSC) Recruitment and Graft Composition on Transplant Outcome after Reduced Intensity Allogeneic Peripheral Blood Stem Cell Transplantation (PBSCT): A Study of the Société Française de Greffe de Moelle Osseuse et de Thérapie Cellulaire (SFGM-TC) Registry", Blood, 2005, p. 1146, vol. 106, Issue 11, American Society of Hematology, Washington, DC.
Hayakawa et al. (2010) "5% dimethyl sulfoxide (DMSO) and penstarch improves cyopreservation of cord blood cells over 10%DMSO", Transfusion, vol. 50, No. 10, pp. 2158-2166.
Markiewicz et al. (2004) "Allogeneic transplantation of selected peripheral CD34+ cells with controlled CD3+ cells add-back in high risk patients", Transplantation Proceedings, vol. 36, pp. 3194-3199.
Korbling M. et al.(1995) "Allogenic blood stem cell transplantation for refractory leukemia and lymphoma: Potential advantage of blood over marrow allografts", Blood, vol. 86, No. 6, pp. 1659-1665.
Kim et al. (2004) "A pilot study of cytoreductive chemotherapy combined with infusion of additional peripheral blood stem cells reserved at time of harvest for transplantation in case or relapsed

(56) References Cited

OTHER PUBLICATIONS hematologic malignancies after allogeneic peripheral blood stem cell transplant", Bone Marrow Transplantation, vol. 33, pp. 231-236.

Liang et al. (2004) "Donor CD8+ T Cells Facilitate Induction of Chimerism and Tolerance without GVHD in Autoimmune NOD Mice Conditioned with Anti-CD3 mAb", v.104, p. 1204.

| Patients* | Age/Gender | ESRD Cause | Total Dose TLI (cGy) | CD34* Cell Dose(x$10^5$/kg) | CD3* Cell Dose(x$10^5$/kg) | Serum creatinine at last observation (mg/dL) | Duration of chimerism |
|---|---|---|---|---|---|---|---|
| 1 (26 mo) | 47/M | IgA | 1200 | 11.8 | 3 | 1.7 | 1 mo |
| 2 (10 mo) | 24/F | SLE | 1200 | 14.5 | 10 | 0.9 | 10 mo |
| 3 (6 mo) | 35/F | Unknown | 1200 | 21.9 | 10 | 1.0 | 6 mo |
| 4 (6 mo) | 33/M | Unknown | 1200 | 9 | 10 | 1.3 | <1 mo |

* parentheses show duration of follow-up from kidney transplant

FIG. 2

Days after Transplantation

COMBINED ORGAN AND HEMATOPOIETIC CELLS FOR TRANSPLANTATION TOLERANCE OF GRAFTS

CROSS-REFERENCE

This application claims benefit and is a Continuation of application Ser. No. 15/914,736 filed Mar. 7, 2018, now issued as U.S. Pat. No. 10,159,694, which is a Continuation of application Ser. No. 15/387,292 filed Dec. 21, 2016, now U.S. Pat. No. 9,974,807, issued May 22, 2018, which is a Continuation of application Ser. No. 14/438,159 filed Apr. 23, 2015, now U.S. Pat. No. 9,561,253 issued Feb. 7, 2017, which is a 371 application and claims the benefit of PCT Application No. PCT/US2014/015394, filed Feb. 7, 2014, which claims benefit of U.S. Provisional Application No. 61/769,596, filed Feb. 26, 2013, which application is incorporated herein by reference.

BACKGROUND

Advances in surgical techniques and improved drugs that prevent infection and rejection have allowed transplantation of solid organs to become an effective treatment for many diseases. Transplanted organs include heart, intestine, liver, lung, pancreas and kidney. Kidney transplantation, or renal transplantation, is the organ transplant of a kidney into a patient with end-stage renal disease. Kidney transplantation can be classified as deceased or living-donor transplantation, and may further be classified according to the degree of relationship between donor and recipient, as related or non-related, and according to the number of human leukocyte antigen (HLA)-matches or HLA-mismatches.

The indication for kidney transplantation is end-stage renal disease (ESRD), regardless of the primary cause, defined as a glomerular filtration rate below a pre-determined level. Common diseases leading to ESRD include malignant hypertension, infections, diabetes mellitus, and focal segmental glomerulosclerosis; genetic causes include polycystic kidney disease, a number of inborn errors of metabolism, and autoimmune conditions such as lupus. Diabetes is a common cause of kidney transplantation, accounting for approximately 25% of those in the US. The majority of renal transplant recipients are on dialysis at the time of transplantation.

The major barrier to organ transplantation between genetically non-identical patients lies in the recipient's immune system, which can respond to the transplanted kidney as "non-self" and reject it. Thus, having medications to suppress the immune system is essential, however, suppressing an individual's immune system places that individual at greater risk of infection and cancer, in addition to the side effects of the medications. Recipients usually receive a mixture of three maintenance immunosuppressive drugs, including a calcineurin inhibitor such as cyclosporine A, tacrolimus or sirolimus; prednisone; and an inhibitor of nucleic acid synthesis such as mycophenolate mofetil. The latter drugs have side effects that include hypertension, nephrotoxicity, infection, and heart disease that contribute to long term patient disability and graft loss. In spite of modern immunosuppressive drugs, in some centers acute rejection can occur in 10-25% of people after transplant.

Generally transplant recipients will take immunosuppressive anti-rejection drugs for as long as the transplanted kidney functions. Even for a mixture of widely used immunosuppressives the cost can be high.

Preclinical studies have shown that conditioning with total lymphoid irradiation (TLI) and anti-thymocyte globulin (ATG) is advantageous for inducing tolerance after combined organ and bone marrow transplantation because the conditioning regimen prevents graft versus host disease (GVHD) as compared to total body irradiation (TBI). For a review, see Strober et al. (2011) Seminars in Immunology 23:273-281.

It is therefore of great clinical interest to develop therapeutic regimens that achieve tolerance and complete withdrawal of immunosuppressive drugs in adult transplant patients and without induction of GVHD.

SUMMARY

Methods and compositions are provided herein for the combined transplantation of a solid organ and hematopoietic cells to a recipient, where tolerance to the graft is established through development of a stable mixed chimera. Preferably, the solid organ is a kidney. An individual with stable mixed chimerism, usually for a period of at least six months, is able to withdraw from the use of immunosuppressive drugs after a period of time sufficient to establish tolerance.

Disclosed herein are methods for organ transplantation. The methods provided herein describe, in some cases, following transplantation of an HLA-matched or HLA-mismatched solid organ, administration of donor-derived hematopoietic stem cells to a recipient. In some cases, the donor-derived hematopoietic stem cells may be prepared to be at least 70% pure prior to formulation as an engineered hematopoietic cell composition.

In some cases, a method for transplantation of an HLA-mismatched solid organ from a donor comprising implanting the HLA-mismatched solid human organ from the donor in a recipient human body, treating the recipient with non-myeloablative conditioning, infusing the recipient with an engineered hematopoietic cell composition comprising at least $1 \times 10^6$ CD34$^+$ cells/kg and at least $1.0 \times 10^7$ CD3$^+$ cells/kg, and maintaining the recipient on an immunosuppressive regimen for a period of time sufficient to develop mixed chimerism for at least six months is disclosed.

In some cases, the methods may include infusing at least $10 \times 10^6$ CD34$^+$ cells/kg recipient weight and at least $1.0 \times 10^6$ CD3$^+$ cells/kg into the recipient. In some cases, at least $10 \times 10^6$ CD34$^+$ cells/kg recipient weight and at least $1.0 \times 10^7$ CD3$^+$ cells/kg are infused into the recipient. In some cases, at least $10 \times 10^6$ CD34$^+$ cells/kg recipient weight and between $1.0$-$5.0 \times 10^6$ CD3$^+$ cells/kg are infused into the recipient. In some cases, less than $15 \times 10^6$ CD34$^+$ cells/kg recipient weight and at least $50 \times 10^6$ CD3$^+$ cells/kg are infused into the recipient.

In some cases, a method is provided for transplantation of a solid organ, the method comprising implanting the solid human organ from a donor in a recipient human body, and infusing the recipient with an allogeneic hematopoietic cell composition comprising donor-derived CD34$^+$ cells and CD3$^+$ cells for a period of time sufficient to allow withdrawal from immunosuppressive drugs in said recipient for a period of at least six months is disclosed. For example, the cellular concentration of iron (e.g. bound to or internalized) in the donor-derived CD34$^+$ cells and/or the cellular concentration of iron in the donor-derived CD3$^+$ cells may be between 5 and 100 pg.

In some cases, a method is provided for transplantation of a solid organ, the method comprising, implanting the solid human organ from a donor in a recipient human body; and infusing the recipient with an allogeneic hematopoietic cell composition comprising donor-derived CD34$^+$ cells of at least 70% purity and CD3$^+$ cells for a period of time sufficient to allow withdrawal from immunosuppressive drugs in said recipient for a period of at least six months.

In some cases, the methods may include isolation of CD34+ cells from at least one apheresis product, two apheresis products, three apheresis products, four apheresis products or five apheresis products. In some cases, the apheresis product is isolated from a solid organ donor. In some cases, the CD3+ cells are isolated from a CD34- depleted fraction of the apheresis product. In some cases, the CD34-depleted fraction of the apheresis product is the CD34-depleted flow-through fraction from an affinity column.

In some cases, the methods may include transplantation of a solid organ from a donor to a recipient, wherein the solid organ is selected from a group consisting of a heart, intestine, liver, lung, pancreas and kidney. The solid organ may be a portion of a whole organ, may be obtained from a living donor or a deceased donor and/or may be related or non-related to the recipient.

In some cases, the methods may include determining whether a donor and a recipient are HLA-matched or HLA-mismatched by typing the six HLA alleles of HLA-A, HLA-B and HLA-DR in each of the donor and the recipient. HLA-matched cells are those in which all six of the HLA alleles are the same between the donor and the recipient. HLA-mismatched cells are those in which at least one HLA allele of the six is different between the donor and the recipient.

In some cases, the methods may include that the recipient undergoes non-myeloablative conditioning, which conditioning comprises lymphoid tissue irradiation in combination with T cell depleting antibodies or drugs prior to infusing the cell composition. In some cases, the methods may include that the recipient undergoes an immunosuppressive regimen that can include but is not limited to a calcineurin inhibitor, and a purine metabolism inhibitor for a period of at least six months.

In some cases, the methods may also include monitoring the recipient for stable mixed chimerism. Mixed chimerism is defined as an individual having at least 1% and less than 95% circulating donor hematopoietic and/or immune cells. In some cases, stable mixed chimerism is defined as having at least 1% and less than 10% circulating donor hematopoietic and/or immune cells, less than 15%, less than 20%, less than 25%, less than 30%, less than 35%, less than 40%, less than 45%, less than 50%, less than 55%, less than 60%, less than 65%, less than 70%, less than 75%, less than 80%, less than 85% or less than 90% circulating donor hematopoietic and/or immune cells, for a period of time, for example for at least 1 month, at least 2 months, at least 3 months, at least 4 months, at least 5 months at least 6 months.

In some cases, the methods may include withdrawal of immunosuppression from individuals found to have mixed chimerism for at least three months, for at least six months or for at least twelve months.

Disclosed herein are compositions for use with organ transplantation. The compositions provided herein find use, in some cases, for administration of a composition of donor-derived hematopoietic stem cells to a recipient following transplantation of an HLA-matched or HLA-mismatched solid organ. In some cases, such compositions comprise donor-derived hematopoietic stem cells, which may be at least 70% pure. In some cases, the allogeneic hematopoietic cell composition comprises donor-derived CD34$^+$ cells and donor-derived CD3$^+$ cells, the cellular concentration of iron in each of the donor-derived cells is between 5 and 100 pg, wherein the number of cells is an amount sufficient to allow withdrawal from immunosuppressive drugs when transplanted in a recipient at least one year following solid organ transplantation.

In some cases, the compositions may include infusion of at least 10×10$^6$ CD34$^+$ cells/kg recipient weight and at least 1.0×10$^6$ CD3$^+$ cells/kg into the recipient. In some cases, at least 10×10$^6$ CD34$^+$ cells/kg recipient weight and at least 1.0×10$^7$ CD3$^+$ cells/kg into the recipient. In some cases, at least 10×10$^6$ CD34$^+$ cells/kg recipient weight and between 1.0-5.0×10$^6$ CD3$^+$ cells/kg into the recipient. In some cases, less than 15×10$^6$ CD34$^+$ cells/kg recipient weight and at least 50×10$^6$ CD3$^+$ cells/kg into the recipient.

In some cases, the solid organ is HLA-matched or HLA-mismatched. In some cases, the solid organ is selected from a group consisting of a heart, intestine, liver, lung, pancreas and kidney.

In some cases, the composition may be administered along with transplantation of a solid organ from a donor to a recipient, wherein the solid organ is selected from a group consisting of a heart, intestine, liver, lung, pancreas and kidney. The solid organ may be a portion of a whole organ, may be obtained from a living donor or a deceased donor and/or may be related or non-related to the recipient.

In some cases, the compositions may be administered after determining whether a donor and a recipient are HLA-matched or HLA-mismatched by typing HLA alleles HLA-A, HLA-B and HLA-DR in the donor and the recipient. HLA-matched may refer to a match wherein each of the HLA alleles at HLA-A, HLA-B and HLA-DR are the same between the donor and the recipient. HLA-mismatched may refer to a match wherein at least one HLA allele at HLA-A, HLA-B and HLA-DR is different between the donor and the recipient.

In some cases, a composition of isolated hematopoietic cells formulated for administration to a recipient may comprise at least 1×10$^6$/kg intended recipient of CD34$^+$ cells isolated from a donor-derived apheresis product, wherein a cellular concentration of iron in the CD34$^+$ cells is between 5 and 100 pg of iron per cell, and at least 1×10$^7$/kg intended recipient of CD3$^+$ T cells isolated from a donor-derived apheresis product, wherein a cellular concentration of iron in the CD3$^+$ cells is between 5 and 100 pg of iron per cell, and a pharmaceutical carrier. Weight of an intended recipient may be determined prior to formulation of the engineered product. Alternatively a product can be formulated with the appropriate number of or ratio of CD34$^+$ cells and CD3$^+$ cells, and the appropriate volume of the product administered to the recipient.

In some cases, the composition may be generated from an apheresis product that is derived from a donor treated with at least 10 micrograms/kg of G-CSF. In some cases, the G-CSF is administered to the donor in two doses. In some cases, the apheresis product is isolated from the donor less than five hours after the second dose of G-CSF.

In some cases, the composition may include CD34+ cells and CD3+ cells isolated from the apheresis product using at least an affinity agent and a column, the CD34+ cells located in an eluate from the column and the CD3+ cells located in a CD34+ cell depleted flow-through fraction from the column.

In some cases, the cellular concentration of iron in the CD34$^+$ cells in the composition is between 5 and 100 pg per cell, for example 5 and 10 pg of iron per cell, 7.5 and 15 pg of iron per cell, 10 and 20 pg of iron per cell, 15 and 30 pg of iron per cell, 20 and 40 pg of iron per cell, 30 and 50 pg of iron per cell, 40 and 60 pg of iron per cell, 50 and 70 pg of iron per cell, 60 and 80 pg of iron per cell, 70 and 90 pg of iron per cell or 80 and 100 pg of iron per cell.

In some cases, the cellular concentration of iron in the CD3+ cells in the composition is between 5 and 10 pg of iron per cell, 7.5 and 15 pg of iron per cell, 10 and 20 pg of iron per cell, 15 and 30 pg of iron per cell, 20 and 40 pg of iron per cell, 30 and 50 pg of iron per cell, 40 and 60 pg of iron per cell, 50 and 70 pg of iron per cell, 60 and 80 pg of iron per cell, 70 and 90 pg of iron per cell or 80 and 100 pg of iron per cell.

In some cases, the CD34+ cells of the hematopoietic cell composition are at least 70% pure prior to formulation of the hematopoietic cell composition. In some cases, the composition is administered to a recipient that is HLA-matched to the CD34+ cells and CD3+ cells, or HLA-mismatched to the CD34+ cells and CD3+ cells. In some cases, the cells of the composition are determined to be HLA-matched or HLA-mismatched by typing HLA alleles HLA-A, HLA-B, and HLA-DR in the donor and the recipient.

In some cases, a cellular composition is generated from hematopoietic cells which are HLA-matched, where HLA alleles HLA-A, HLA-B, HLA-DR are the same between the donor and the recipient. In some cases, the composition is generated from hematopoietic cells which are HLA-mismatched, where at least one HLA allele of HLA-A, HLA-B, HLA-DR is different between the donor and the recipient. In some cases, the composition is generated from an apheresis product taken from a donor that is related or non-related to the recipient.

In some cases, the compositions may include CD34+ cells that are isolated from at least one apheresis product, two apheresis products, three apheresis products, four apheresis products or five apheresis products. In some cases, the apheresis product is isolated from a solid organ donor. In some cases, the CD3+ cells are isolated from a CD34-depleted fraction of the apheresis product. In some cases, the CD34-depleted fraction of the apheresis product is the CD34-depleted flow-through fraction from an affinity column.

Disclosed herein are kits for organ transplantation. The kits provided herein describe, in some cases, preparation of a composition of hematopoietic stem cells which may be administered to a recipient following transplantation of an HLA-matched or HLA-mismatched solid organ. In some cases, the kit of component parts capable for use in preparing an engineered hematopoietic cell composition comprises at least one affinity reagent for CD34, at least one device for separating CD34+ cells from a plurality of cells, at least one agent for determining a number of CD3+ cells; and instructions for isolating CD34+ cells from a plurality of cells and determining the number of CD3+ cells using at least the component parts of the kit to generate the engineered hematopoietic cell composition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 2 is a table of results from haplotype matched organ transplants.

DETAILED DESCRIPTION

Figure 1:
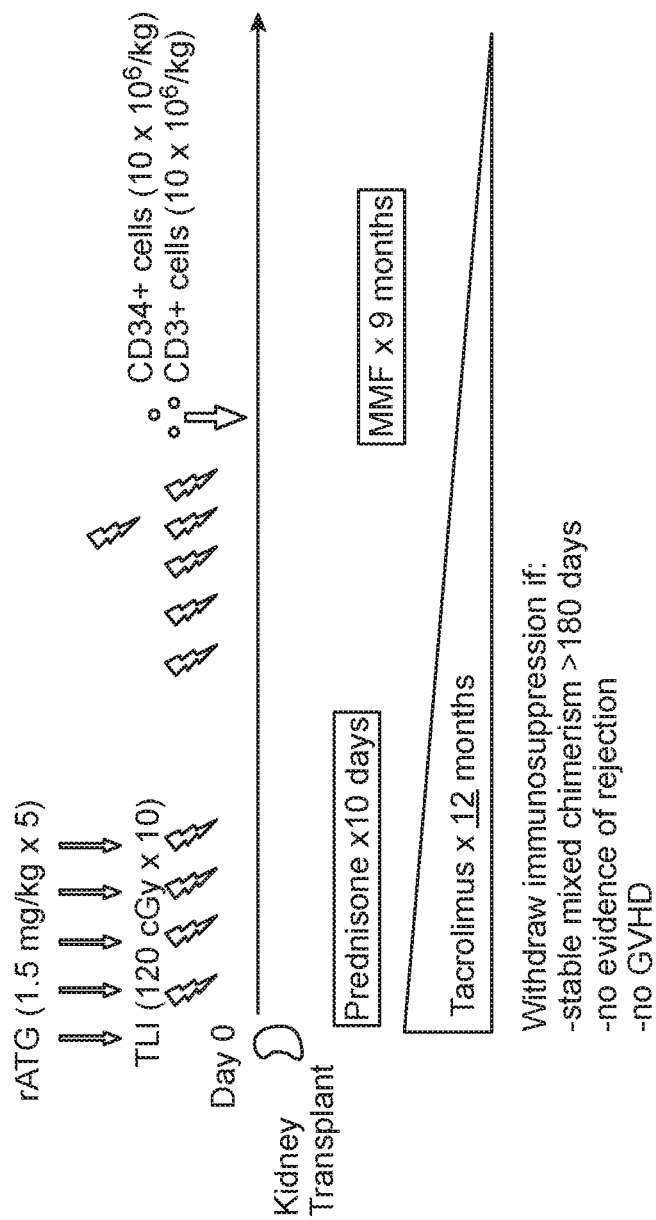
FIG. 1 illustrates a protocol for kidney and hematopoietic cell transplantation for a haplotype matched donor and recipient.
Figure 3:
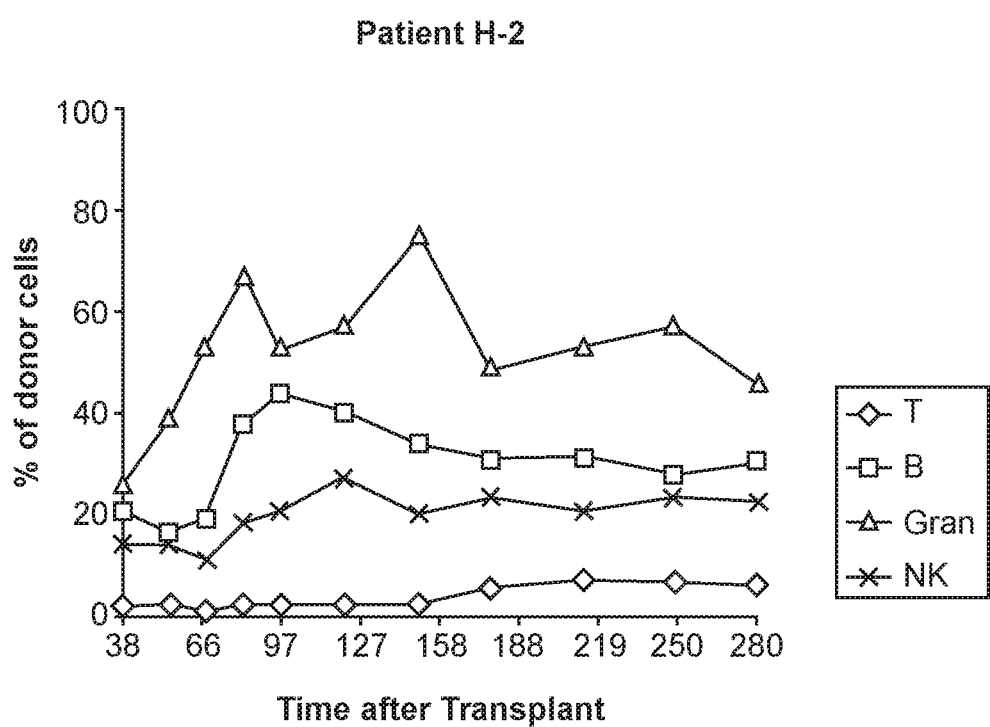
FIG. 3 provides a graph assessment of chimerism following haplotype matched combined organ transplant in patient #2 from FIG. 2.

While preferred aspects of the present disclosure have been shown and described herein, it is to be understood that the disclosure is not limited to the particular aspects of the disclosure described below, as variations of the particular aspects may be made and still fall within the scope of the appended claims. It is also to be understood that the terminology employed is for the purpose of describing particular aspects of the disclosure, and is not intended to be limiting. Instead, the scope of the present disclosure is established by the appended claims. In this specification and the appended claims, the singular forms "a," "an" and "the" include plural reference unless the context clearly dictates otherwise.

Definitions

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the disclosure provided herein.

Unless defined otherwise, all technical and scientific terms used herein have the same meaning as commonly understood to one of ordinary skill in the art to which this disclosure belongs. Although any methods, devices and materials similar or equivalent to those described herein can be used in the practice or testing of the disclosure, the preferred methods, devices and materials are now described.

"Major histocompatibility complex antigens" ("MHC", also called "human leukocyte antigens", HLA) are protein molecules expressed on the surface of cells that confer a unique antigenic identity to these cells. MHC/HLA antigens are target molecules that are recognized by T-cells and natural killer (NK) cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans)

render each cell recognizable as "self," whereas HLA class II antigens (DR, DP, and DQ in humans) are involved in reactions between lymphocytes and antigen presenting cells. Both have been implicated in the rejection of transplanted organs.

An important aspect of the HLA gene system is its polymorphism. Each gene, MHC class I (A, B and C) and MHC class II (DP, DQ and DR) exists in different alleles. HLA alleles are designated by numbers and subscripts. For example, two unrelated individuals may carry class I HLA-B, genes B5, and Bw41, respectively. Allelic gene products differ in one or more amino acids in the α and/or β domain(s). Large panels of specific antibodies or nucleic acid reagents are used to type HLA haplotypes of individuals, using leukocytes that express class I and class II molecules. The genes most important for HLA typing are the six MHC Class I and Class II proteins, two alleles for each of HLA-A; HLA-B and HLA-DR.

The HLA genes are clustered in a "super-locus" present on chromosome position 6p21, which encodes the six classical transplantation HLA genes and at least 132 protein coding genes that have important roles in the regulation of the immune system as well as some other fundamental molecular and cellular processes. The complete locus measures roughly 3.6 Mb, with at least 224 gene loci. One effect of this clustering is that "haplotypes", i.e. the set of alleles present on a single chromosome, which is inherited from one parent, tend to be inherited as a group. The set of alleles inherited from each parent forms a haplotype, in which some alleles tend to be associated together. Identifying a patient's haplotypes can help predict the probability of finding matching donors and assist in developing a search strategy, because some alleles and haplotypes are more common than others and they are distributed at different frequencies in different racial and ethnic groups.

As used herein, the term "HLA matched" refers to a donor recipient pair in which none of the HLA antigens are mismatched between the donor and recipient. HLA matched (i.e., where all of the 6 alleles are matched) donor/recipient pairs have a decreased risk of graft v. host disease (GVHD) relative to mismatched pairs (i.e. where at least one of the 6 alleles is mismatched).

As used herein, the term "HLA mismatched" refers to a donor recipient pair in which at least one HLA antigen, in particular with respect to HLA-A, HLA-B and HLA-DR, is mismatched between the donor and recipient. In some cases, one haplotype is matched and the other is mismatched. This situation is frequently found with organs from living or deceased donors. HLA mismatched donor/recipient pairs have an increased risk of GVHD relative to perfectly matched pairs (i.e. where all 6 alleles are matched).

HLA alleles are typically noted with a variety of levels of detail. Most designations begin with HLA- and the locus name, then * and some (even) number of digits specifying the allele. The first two digits specify a group of alleles. Older typing methodologies often could not completely distinguish alleles and so stopped at this level. The third through fourth digits specify a synonymous allele. Digits five through six denote any synonymous mutations within the coding frame of the gene. The seventh and eighth digits distinguish mutations outside the coding region. Letters such as L, N, Q, or S may follow an allele's designation to specify an expression level or other non-genomic data known about it. Thus, a completely described allele may be up to 9 digits long, not including the HLA-prefix and locus notation.

As used herein, a "recipient" is an individual to whom an organ, tissue or cells from another individual (donor), commonly of the same species, has been transferred. For the purposes of the present disclosure, a recipient and a donor are either HLA-matched or HLA-mismatched.

As used herein, the term "solid organ transplantation" is used in accordance with the conventional meaning of the term, where an organ from a donor, which donor may be living or deceased, in placed into the body of a recipient in the appropriate position and cardiovascular connections to be physiologically integrated into the recipient. Transplantation of a kidney is of particular interest for the methods of the disclosure, although the methods do not exclude transplantation of other organs, e.g. pancreas and including pancreatic islet cells; heart; lungs, intestine, liver, and the like as known in the art. The transplanted organ may be referenced as a "graft", and the physiological integration of the organ may be referred to as engraftment.

Hematopoietic stem cell transplantation (HCT) is the transplantation of multipotent hematopoietic stem cells, usually derived from bone marrow, peripheral blood, or umbilical cord blood. For the methods of the disclosure, the hematopoietic cells may be engineered into one of two products. The hematopoietic cells are engineered into a product for infusion having a specific pre-determined number of purified (e.g., ≥70% purity) CD34+ progenitor cells and CD3+ T cells. The hematopoietic cells can be obtained from the solid organ donor, and thus are HLA-matched to the solid organ, and HLA-mismatched to the organ recipient. The hematopoietic cells may be obtained from the solid organ donor, and thus are HLA-matched to the solid organ, and HLA-matched to the organ recipient.

Where the donor is deceased, hematopoietic cells may be obtained from bone marrow (e.g. vertebrae, pelvic bone, etc). Where the donor is a living donor, hematopoietic cells may be mobilized (e.g. with G-CSF), and collected by apheresis or similar methods. Alternatively, cells may be obtained from bone marrow (e.g. pelvic bone, etc).

Hematopoietic cells can be frozen (e.g., cryopreserved) for prolonged periods without damaging a significant number of cells. To cryopreserve HSC, a preservative, DMSO, must be added, and the cells must be cooled very slowly in a controlled-rate freezer to prevent osmotic cellular injury during ice crystal formation. HSC may be stored for years in a cryofreezer, which typically uses liquid nitrogen.

The recipient's immune system is conditioned with a non-myeloablative procedure prior to infusion of the hematopoietic cells. Non-myeloablative transplants use doses of antibody and radiation that are too low to eradicate all the bone marrow cells of a recipient, thus enabling the desired goal of stable mixed chimerism where both recipient and donor HSC coexist in the bone marrow space. The conditioning regimen includes treatment with anti-thymocyte globulin (ATG); total lymphoid irradiation, and corticosteroids (e.g. prednisone) usually for a period of from about 10 to 12 days (e.g. for about 11 days).

"Immunosuppression", as used herein, refers to the treatment of a graft recipient with agents, primarily to diminish the immune responses of the host immune system against the graft, although the agents may also diminish GVHD of the donor hematopoietic cells. Exemplary immunosuppression regimens are described in more detail herein, but will generally be conventional for a period of about 6 to 12 months. The recipient is tested for mixed chimerism of the hematopoietic system, and if found to have maintained mixed chimerism after at least 6 months, will be tapered off immunosuppression.

Immunosuppressive treatment of the transplantation patient begins with the induction phase, perioperatively and immediately after transplantation. Maintenance therapy then continues until withdrawal for individuals showing stable mixed chimerism. Induction and maintenance strategies use different medicines at specific doses or at doses adjusted to achieve target therapeutic levels to give the transplantation patient the best hope for long-term graft survival.

Primary immunosuppressive agents include calcineurin inhibitors, which combine with binding proteins to inhibit calcineurin activity, and which include, for example, tacrolimus, cyclosporine A, etc. Levels of both cyclosporine and tacrolimus must be carefully monitored. Initially, levels can be kept in the range of 10-20 ng/mL, but, after 3 months, levels may be kept lower (5-10 ng/mL) to reduce the risk of nephrotoxicity.

Adjuvant agents are usually combined with a calcineurin inhibitor and include steroids, azathioprine, mycophenolate mofetil, and sirolimus. Protocols of interest include a calcineurin inhibitor with mycophenolate mofetil. The use of adjuvant agents allows clinicians to achieve adequate immunosuppression while decreasing the dose and toxicity of individual agents. Mycophenolate mofetil in kidney transplant recipients has assumed an important role in immunosuppression after several clinical trials have shown a markedly decreased prevalence of acute cellular rejection compared with azathioprine and a reduction in 1-year treatment failures.

Antibody-based therapy uses monoclonal (e.g., muromonab-CD3) or polyclonal antibodies or anti-CD25 antibodies (e.g., basiliximab, daclizumab) and is administered in the early posttransplant period (up to 8 wk). Antibody-based therapy allows for avoidance or dose reduction of calcineurin inhibitors, possibly reducing the risk of nephrotoxicity. The adverse effect profile of the polyclonal and monoclonal antibodies limits their use in some patients.

Graft-versus-host disease (GVHD) is an inflammatory disease that is peculiar to transplantation of hematopoietic cells. It is an attack of the donor bone marrow's immune cells against the recipient's tissues. GVHD is a risk for both HLA-matched and -mismatched transplantations. GVHD can occur even if the donor and recipient are HLA-matched because the immune system can still recognize other differences between their tissues. GVHD is usually mediated by T cells, which react to foreign peptides presented on the MHC of the host. The risk of GVHD is markedly reduced in patients with mixed instead of complete chimerism and achieving mixed chimerism is desirable for this reason. In addition, immunodeficiency and infection are more frequently observed in complete versus mixed chimerism.

There are two types of GVHD, acute and chronic. Acute GVHD typically occurs in the first 3 months after transplantation and may involve the skin, intestine, or the liver. High-dose corticosteroids such as prednisone are a standard treatment.

Chronic GVHD may also develop after haplotype matched transplant and typically occurs after the first 3 months following transplant. It is the major source of late treatment-related complications, although it less often results in death. In addition to inflammation, chronic GVHD may lead to the development of fibrosis, or scar tissue, similar to scleroderma; it may cause functional disability and require prolonged immunosuppressive therapy.

"Acute transplant rejection" is the rejection by the immune system of a transplanted organ. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery.

Generally, acute rejection is inhibited or suppressed with immunosuppressive drugs. Steroids are the mainstay of therapy for acute rejection episodes. The typical dosage is 3-5 mg/kg/d for 3-5 days, which is then tapered to a maintenance dose. ATG and muromonab-CD3 also find use.

"Chronic transplant rejection" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome.

Chronic rejection can also be characterized by ischemic insult, denervation of the transplanted tissue, hyperlipidemia and hypertension associated with immunosuppressive drugs. Unless inadequate immunosuppression is the cause of rejection, changes in immunosuppressive therapy are generally not effective in reversing chronic rejection. Control of blood pressure, treatment of hyperlipidemia, and management of diabetes are the current mainstays of treatment for graft preservation.

The term "transplant rejection" encompasses both acute and chronic transplant rejection. In transplant rejection, the transplanted tissue is rejected and destroyed by the recipient's immune system. Acute rejection may occur to some degree in all transplants, except in the cases of identical twins or during immunosuppression. Acute rejection may begin as soon as one week after transplant and greatest risk for development of acute rejection occurs in the first three months following transplant. Chronic rejection is the long-term loss of function of a transplanted organ.

Hematopoietic cell transplant loss is the absence of hematopoietic reconstitution of donor origin on day +45 after the allograft (primary graft rejection) or as confirmed loss of donor cells after transient engraftment of donor-origin hematopoiesis. Kidney graft failure is creatinine clearance declining to less than 10 ml/min or the return of the patient to dialysis, or the return of the patient to the transplant list for re-transplantation.

Chimerism, as used herein, generally refers to chimerism of the hematopoietic system, unless otherwise noted. A determination of whether an individual is a full chimera, mixed chimera, or non-chimeric made be made by an analysis of a hematopoietic cell sample from the graft recipient, e.g. peripheral blood, bone marrow, etc. as known in the art. Analysis may be done by any convenient method of typing. In some embodiments the degree of chimerism amongst all mononuclear cells, T cells, B cells, CD56+NK cells, and CD15+ neutrophils is regularly monitored, using PCR with probes for microsatellite analysis. For example, commercial kits that distinguish polymorphisms in short terminal repeat lengths of donor and host origin are available. Automated readers provide the percentage of donor type cells based on standard curves from artificial donor and host cell mixtures.

Individuals who exhibited more than a 95% donor cells in a given blood cell lineage by such analysis at any time post-transplantation are referred to as having full donor chimerism in this transplant patient group. Mixed chimerism is defined as greater than 1% donor but less than 95% donor DNA in such analysis. Individuals who exhibit mixed chimerism may be further classified according to the evolution of chimerism, where improving mixed chimerism is defined as a continuous increase in the proportion of donor cells over at least a 6-month period. Stable mixed chimerism is defined as fluctuations in the percentage of recipient cells over time, without complete loss of donor cells. Candidates for withdrawal of immunosuppression have mixed chimerism until at least 6 months post-transplantation.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease.

"Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans.

The term "graft management" refers to therapeutic methods that induce and/or promote repair engraftment of a solid organ, but not limited to, kidney transplantation.

The term "pharmaceutically acceptable" as used herein refers to a compound or combination of compounds that will not impair the physiology of the recipient human or animal to the extent that the viability of the recipient is compromised. Preferably, the administered compound or combination of compounds will elicit, at most, a temporary detrimental effect on the health of the recipient human or animal.

The term "carrier" as used herein refers to any pharmaceutically acceptable solvent of agents that will allow a therapeutic composition to be administered directly to a wound of the skin. The carrier will allow a composition to be topically applied to an exposed surface of an organ for transplantation and the site of the recipient where the organ is to be placed. A "carrier" as used herein, therefore, refers to such solvent as, but not limited to, water, saline, oil-water emulsions, or any other solvent or combination of solvents and compounds known to one of skill in the art that is pharmaceutically and physiologically acceptable to the recipient human or animal.

The term "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

Methods

The methods of the disclosure are discussed in detail below. In some cases, the methods described herein may comprise the steps of: HLA typing a donor and recipient to determine an HLA-matched or HLA-mismatched pair. "HLA-matched" indicates all of the 6 HLA antigens (e.g., HLA-A, B, DR) are matched between a donor and a recipient. "HLA-mismatched" indicates that at least 1, at least 2, at least 3 of 6 HLA antigens (e.g., HLA-A, B, DR) are mismatched. Generally at least a portion of the 6 HLA antigens (e.g., HLA-A, B, DR) are matched, for example at least 1, at least 2, at least 3, at least 4, at least 6 matches.

In some cases, the methods may include at least the following steps; obtaining the solid organ and hematopoietic cells from the donor; isolating hematopoietic cells of the appropriate type and dose; transplanting the solid organ; performing a conditioning regimen on the recipient following transplantation of the solid organ and prior to infusion of the engineered hematopoietic cells; maintaining the recipient on an immunosuppressive regimen for at least six months; monitoring the recipient for mixed chimerism of the hematopoietic system; and withdrawing immunosuppression if the recipient shows stable mixed chimerism. The methods described herein apply to both HLA-matched and HLA-mismatched transplantation conditions.

Individuals selected for the methods described herein may meet the criteria of (i) requiring a solid organ graft; and (ii) having either an HLA-matched or HLA-mismatched donor from which the solid organ and hematopoietic cells can be obtained. By performing a combined transplant of solid organ and an engineered hematopoietic cell infusion appropriate for the individual, in combination with non-myeloablative conditioning, the patient may have a high probability of developing persistent mixed chimerism for at least 6 months. Mixed chimerism which persists for at least 6 months may allow for withdrawal of immunosuppression over time.

Typing Human Leukocyte Antigens

Any method known in the art may be used to type donor-derived cells and a sample from the recipient. For example, three main procedures may be used to perform HLA typing. The first is conventional serological cytotoxicity method, where samples of lymphocytes (e.g., taken from blood or spleen) are added to Terasaki plates. In some cases, B lymphocytes may be used for class II typing. In other cases, class I typing may be performed with the remaining leucocytes. Magnetic beads may be used to purify cells from blood or spleen.

In some cases, each of the wells of the Terasaki plates may contain a plurality of antibodies (e.g., from either maternal sera or manufactured monoclonal antibodies). In some cases, the HLA antigen expressed by a cell binds to an antibody in the well. After the addition of complement, cells located in a well where the HLA antigen and antibody were bound may be killed. In some cases, a pattern of cell death may be determined from the wells. The pattern may allow for deduction of the combination of HLA antigens that were present on the original tissue. In some cases, the deduction of the combination of HLA antigens may result in typing of HLA antigens.

Another method that may be used for HLA typing is flow cytometry. Unlike the conventional serological cytotoxicity method, flow cytometry may be used to identify one or more HLA alleles. In this method, leukocytes may be combined with antibodies that bind to the HLA types of interest. In some cases the antibodies may be monoclonal or polyclonal. In some cases, the antibodies may contain a detectable label. In some cases, the antibodies may be directly conjugated to a detectable label. In other cases, a different antibody with a detectable label binds to the HLA antibody and the complex is then detected. The types of detectable labels that may be used for HLA typing by flow cytometry are readily available and known to those of skill in the art. The sample may be analyzed to determine which HLA antibodies have bound to the cells.

Yet another method that may be used for HLA typing is DNA typing. In some cases, DNA typing involves extracting DNA from cells and amplifying the genes that encode for the HLA peptides using polymerase chain reaction techniques which generate sequence data. The polymerase chain reaction techniques may include any polymerase chain reaction technique which generates sequence data that is known to one of skill in the art.

In some cases, the sequence of the genes may be matched with the known nucleotide sequences of HLA alleles located in at least one of several genetic (e.g., gene bank) databases. In some cases, the gene bank data base may be the IMGT/HLA (International Immunogenetics Project) database.

Solid Organ Transplant

Solid organs may be transplanted from a donor to a recipient such that the organ is placed into the appropriate position in the recipient body. In some cases, the cardiovascular connections between the solid organ may be physiologically integrated into the recipient body. In some cases, the organ may be from a living donor. In other cases, the organ may be from a deceased donor. In some cases, the solid organ may be HLA-matched between the donor and the recipient. In other cases, the solid organ may be HLA-mismatched between the donor and the recipient.

Any solid organ that may be used for organ transplantation may be used with the methods described herein. In some cases, the organ may be a kidney, lung, pancreas, pancreatic islet cells, heart, intestine, colon, liver, skin, muscle, gum, eye, tooth and the like as known to those of skill in the art. In some cases, the organ may be a complete organ. In other cases, the organ may be a portion of an organ. In other cases, the organ may be cells from a tissue of an organ.

Using the methods described herein, the solid organ is harvested and transplanted in accordance with conventional practice. In some cases, the solid organ may be transplanted at least one, two, three, four, five, six, seven, eight, nine, ten, eleven, twelve, thirteen, fourteen, fifteen, sixteen, seventeen, eighteen, nineteen or at least twenty days prior to the infusion of the engineered hematopoietic cells.

Obtaining Hematopoietic Stem Cells for Transplantation

Hematopoietic stem cell transplantation (HCT) includes the transplantation of multipotent hematopoietic stem cells from a donor to a recipient. For the methods described herein, HCT may be combined with solid organ transplant. In some cases, the hematopoietic stem cells may be HLA-matched between the donor and the recipient. In other cases, the hematopoietic stem cells may be HLA-mismatched between the donor and the recipient.

In some cases, the hematopoietic stem cells are isolated and purified from the solid organ donor. The solid organ donor may be living or deceased. In cases of a living donor, hematopoietic cells may be obtained from the solid organ donor using any of the various methods known to one of skill in the art, including apheresis of mobilized peripheral blood from living donors; harvesting hematopoietic cells from bone marrow of deceased donors, and the like. In cases of a deceased donor, hematopoietic cells may be obtained from bone marrow. For example, the cells may be obtained from the bone marrow in vertebrae, pelvic bone, femur or any other bone which contains sufficient bone marrow from which to extract hematopoietic cells.

In some cases, hematopoietic cells may be mobilized prior to isolation and purification. In some cases hematopoietic cells may be mobilized by treating the donor with granulocyte colony stimulating factor (G-CSF). For example, the donor may be treated with one, two, three, four, five, six, seven, eight, nine, ten or more than ten doses of G-CSF prior to isolating and purifying hematopoietic cells.

In some cases, the doses of G-CSF may be delivered to the donor on a single day (e.g., a 24 hour day) or over the course of multiple days. For example, multiple days may include two, three, four, five, six, seven, eight, nine, ten or more than ten days. In a preferred case, the donor receives two doses per day.

In some cases, each dose of G-CSF delivered to the donor is 16 micrograms/kg of donor body weight. In other cases, each dose of G-CSF delivered to the donor is 8 micrograms/kg of donor body weight. For example, each dose of G-CSF may be more than 1 micrograms/kg of donor body weight, 2 micrograms/kg of donor body weight, 3 micrograms/kg of donor body weight, 4 micrograms/kg of donor body weight, 5 micrograms/kg of donor body weight, 6 micrograms/kg of donor body weight, 7 micrograms/kg of donor body weight, 8 micrograms/kg of donor body weight, 9 micrograms/kg of donor body weight, 10 micrograms/kg of donor body weight, 11 micrograms/kg of donor body weight, 12 micrograms/kg of donor body weight, 13 micrograms/kg of donor body weight, 14 micrograms/kg of donor body weight, 15 micrograms/kg of donor body weight, 16 micrograms/kg of donor body weight, 17 micrograms/kg of donor body weight, 18 micrograms/kg of donor body weight, 19 micrograms/kg of donor body weight, 20 micrograms/kg of donor body weight, or more than 20 micrograms/kg of donor body weight. In a preferred case, each dose of G-CSF delivered to the donor is 8 micrograms/kg of donor body weight.

In some cases, apheresis may be performed after the donor receives a single dose of G-CSF. For example, apheresis may be performed one hour, two hours, three hours, four hours, five hours, six hours, seven hours, eight hours, nine hours, ten hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, or more than 48 hours after the donor receives the single dose of G-CSF.

In some cases, apheresis may be performed after the donor receives the final dose of multiple doses of G-CSF. For example, apheresis may be performed one hour, two hours, three hours, four hours, five hours, six hours, seven hours, eight hours, nine hours, ten hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, or more than 48 hours after the donor receives the final dose of multiple doses of G-CSF.

In some cases, apheresis may be performed to obtain an apheresis product from a donor. For example, at least one apheresis product, two apheresis products, three apheresis products, four apheresis products or five apheresis products may be obtained from a donor. In some cases, at least two apheresis products, three apheresis products, four apheresis products, five apheresis products, six apheresis products, seven apheresis products, eight apheresis products, nine apheresis products, ten apheresis products, 11 apheresis products, 12 apheresis products, 13 apheresis products, 14 apheresis products or at least 15 apheresis products may be obtained from a donor.

In some cases, the hematopoietic cells may be obtained from a solid organ donor HLA-matched to the recipient. In this case, the hematopoietic cells are HLA-matched to the solid organ and the solid organ recipient. In some cases, the hematopoietic cells may be obtained from a solid organ donor HLA-mismatched to the recipient. In this case, the hematopoietic cells are HLA-matched to the solid organ and HLA-mismatched to the solid organ recipient.

For the methods described herein, hematopoietic cells may be frozen (e.g., cryopreserved) after isolation or after isolation and purification from the solid organ donor. In some cases, hematopoietic cells may be cryopreserved using a cryopreservation medium and a method of cryopreservation known to those of skill in the art. In some cases, the hematopoietic cells may be cryopreserved using a cryopreservation medium containing dimethylsulfoxide (DMSO), Normosol, Hetastarch and human serum albumin (HSA).

In some cases, the concentration of DMSO in the cryopreservation medium may be less than 0.1% DMSO, 0.2% DMSO, 0.3% DMSO, 0.4% DMSO, 0.5% DMSO, 0.6% DMSO, 0.7% DMSO, 0.8% DMSO, 0.9% DMSO, 1.0% DMSO, 1.1% DMSO, 1.2% DMSO, 1.3% DMSO, 1.4% DMSO, 1.5% DMSO, 1.6% DMSO, 1.7% DMSO, 1.8% DMSO, 1.9% DMSO, 2.0% DMSO, 2.1% DMSO, 2.2% DMSO, 2.3% DMSO, 2.4% DMSO, 2.5% DMSO, 2.6% DMSO, 2.7% DMSO, 2.8% DMSO, 2.9% DMSO, 3.0% DMSO, 3.1% DMSO, 3.2% DMSO, 3.3% DMSO, 3.4% DMSO, 3.5% DMSO, 3.6% DMSO, 3.7% DMSO, 3.8% DMSO, 3.9% DMSO, 4.0% DMSO, 4.1% DMSO, 4.2% DMSO, 4.3% DMSO, 4.4% DMSO, 4.5% DMSO, 4.6% DMSO, 4.7% DMSO, 4.8% DMSO, 4.9% DMSO, 5.0% DMSO, 5.1% DMSO, 5.2% DMSO, 5.3% DMSO, 5.4% DMSO, 5.5% DMSO, 5.6% DMSO, 5.7% DMSO, 5.8% DMSO, 5.9% DMSO, 6.0% DMSO, 6.1% DMSO, 6.2% DMSO, 6.3% DMSO, 6.4% DMSO, 6.5% DMSO, 6.6% DMSO, 6.7% DMSO, 6.8% DMSO, 6.9% DMSO, 7.0% DMSO, 7.1% DMSO, 7.2% DMSO, 7.3% DMSO, 7.4% DMSO, 7.5% DMSO, 7.6% DMSO, 7.7% DMSO, 7.8% DMSO, 7.9% DMSO, 8.0% DMSO, 8.1% DMSO, 8.2% DMSO, 8.3% DMSO, 8.4% DMSO, 8.5% DMSO, 8.6% DMSO, 8.7% DMSO, 8.8% DMSO, 8.9% DMSO, 9.0% DMSO, 9.1% DMSO, 9.2% DMSO, 9.3% DMSO, 9.4% DMSO, 9.5% DMSO, 9.6% DMSO, 9.7% DMSO, 9.8% DMSO, 9.9% DMSO, 10% DMSO, 10.5% DMSO, 11% DMSO, 11.5% DMSO, 12% DMSO, 12.5% DMSO, 13% DMSO, 13.5% DMSO, 14% DMSO, 14.5% DMSO, 15% DMSO, 15.5% DMSO, 16% DMSO, 16.5% DMSO, 17% DMSO, 17.5% DMSO, 18% DMSO, 18.5% DMSO, 19% DMSO, 20% DMSO, 20.5% DMSO, 21% DMSO, 21.5% DMSO, 22% DMSO, 22.5% DMSO, 23% DMSO, 23.5% DMSO, 24% DMSO, 24.5% DMSO, 25% DMSO, 25.5% DMSO, 26% DMSO, 26.5% DMSO, 27% DMSO, 27.5% DMSO, 28% DMSO, 28.5% DMSO, 29% DMSO, 29.5% DMSO, 30% DMSO, 40% DMSO or less than 50% DMSO.

In some cases, the concentration of normosol in the cryopreservation medium may be less than 0.1% normosol, 0.2% normosol, 0.3% normosol, 0.4% normosol, 0.5% normosol, 0.6% normosol, 0.7% normosol, 0.8% normosol, 0.9% normosol, 1.0% normosol, 1.1% normosol, 1.2% normosol, 1.3% normosol, 1.4% normosol, 1.5% normosol, 1.6% normosol, 1.7% normosol, 1.8% normosol, 1.9% normosol, 2.0% normosol, 2.1% normosol, 2.2% normosol, 2.3% normosol, 2.4% normosol, 2.5% normosol, 2.6% normosol, 2.7% normosol, 2.8% normosol, 2.9% normosol, 3.0% normosol, 3.1% normosol, 3.2% normosol, 3.3% normosol, 3.4% normosol, 3.5% normosol, 3.6% normosol, 3.7% normosol, 3.8% normosol, 3.9% normosol, 4.0% normosol, 4.1% normosol, 4.2% normosol, 4.3% normosol, 4.4% normosol, 4.5% normosol, 4.6% normosol, 4.7% normosol, 4.8% normosol, 4.9% normosol, 5.0% normosol, 5.1% normosol, 5.2% normosol, 5.3% normosol, 5.4% normosol, 5.5% normosol, 5.6% normosol, 5.7% normosol, 5.8% normosol, 5.9% normosol, 6.0% normosol, 6.1% normosol, 6.2% normosol, 6.3% normosol, 6.4% normosol, 6.5% normosol, 6.6% normosol, 6.7% normosol, 6.8% normosol, 6.9% normosol, 7.0% normosol, 7.1% normosol, 7.2% normosol, 7.3% normosol, 7.4% normosol, 7.5% normosol, 7.6% normosol, 7.7% normosol, 7.8% normosol, 7.9% normosol, 8.0% normosol, 8.1% normosol, 8.2% normosol, 8.3% normosol, 8.4% normosol, 8.5% normosol, 8.6% normosol, 8.7% normosol, 8.8% normosol, 8.9% normosol, 9.0% normosol, 9.1% normosol, 9.2% normosol, 9.3% normosol, 9.4% normosol, 9.5% normosol, 9.6% normosol, 9.7% normosol, 9.8% normosol, 9.9% normosol, 10% normosol, 10.5% normosol, 11% normosol, 11.5% normosol, 12% normosol, 12.5% normosol, 13% normosol, 13.5% normosol, 14% normosol, 14.5% normosol, 15% normosol, 15.5% normosol, 16% normosol, 16.5% normosol, 17% normosol, 17.5% normosol, 18% normosol, 18.5% normosol, 19% normosol, 20% normosol, 20.5% normosol, 21% normosol, 21.5% normosol, 22% normosol, 22.5% normosol, 23% normosol, 23.5% normosol, 24% normosol, 24.5% normosol, 25% normosol, 25.5% normosol, 26% normosol, 26.5% normosol, 27% normosol, 27.5% normosol, 28% normosol, 28.5% normosol, 29% normosol, 29.5% normosol, 30% normosol, 40% normosol or less than 50% normosol.

In some cases, the concentration of Hetastarch in the cryopreservation medium may be less than 0.1% Hetastarch, 0.2% Hetastarch, 0.3% Hetastarch, 0.4% Hetastarch, 0.5% Hetastarch, 0.6% Hetastarch, 0.7% Hetastarch, 0.8% Hetastarch, 0.9% Hetastarch, 1.0% Hetastarch, 1.1% Hetastarch, 1.2% Hetastarch, 1.3% Hetastarch, 1.4% Hetastarch, 1.5% Hetastarch, 1.6% Hetastarch, 1.7% Hetastarch, 1.8% Hetastarch, 1.9% Hetastarch, 2.0% Hetastarch, 2.1% Hetastarch, 2.2% Hetastarch, 2.3% Hetastarch, 2.4% Hetastarch, 2.5% Hetastarch, 2.6% Hetastarch, 2.7% Hetastarch, 2.8% Hetastarch, 2.9% Hetastarch, 3.0% Hetastarch, 3.1% Hetastarch, 3.2% Hetastarch, 3.3% Hetastarch, 3.4% Hetastarch, 3.5% Hetastarch, 3.6% Hetastarch, 3.7% Hetastarch, 3.8% Hetastarch, 3.9% Hetastarch, 4.0% Hetastarch, 4.1% Hetastarch, 4.2% Hetastarch, 4.3% Hetastarch, 4.4% Hetastarch, 4.5% Hetastarch, 4.6% Hetastarch, 4.7% Hetastarch, 4.8% Hetastarch, 4.9% Hetastarch, 5.0% Hetastarch, 5.1% Hetastarch, 5.2% Hetastarch, 5.3% Hetastarch, 5.4% Hetastarch, 5.5% Hetastarch, 5.6% Hetastarch, 5.7% Hetastarch, 5.8% Hetastarch, 5.9% Hetastarch, 6.0% Hetastarch, 6.1% Hetastarch, 6.2% Hetastarch, 6.3% Hetastarch, 6.4% Hetastarch, 6.5% Hetastarch, 6.6% Hetastarch, 6.7% Hetastarch, 6.8% Hetastarch, 6.9% Hetastarch, 7.0% Hetastarch, 7.1% Hetastarch, 7.2% Hetastarch, 7.3% Hetastarch, 7.4% Hetastarch, 7.5% Hetastarch, 7.6% Hetastarch, 7.7% Hetastarch, 7.8% Hetastarch, 7.9% Hetastarch, 8.0% Hetastarch, 8.1% Hetastarch, 8.2% Hetastarch, 8.3% Hetastarch, 8.4% Hetastarch, 8.5% Hetastarch, 8.6% Hetastarch, 8.7% Hetastarch, 8.8% Hetastarch, 8.9% Hetastarch, 9.0% Hetastarch, 9.1% Hetastarch, 9.2% Hetastarch, 9.3% Hetastarch, 9.4% Hetastarch, 9.5% Hetastarch, 9.6% Hetastarch, 9.7% Hetastarch, 9.8% Hetastarch, 9.9% Hetastarch, 10% Hetastarch, 10.5% Hetastarch, 11% Hetastarch, 11.5% Hetastarch, 12% Hetastarch, 12.5% Hetastarch, 13% Hetastarch, 13.5% Hetastarch, 14% Hetastarch, 14.5% Hetastarch, 15% Hetastarch, 15.5% Hetastarch, 16% Hetastarch, 16.5% Hetastarch, 17% Hetastarch, 17.5% Hetastarch, 18% Hetastarch, 18.5% Hetastarch, 19% Hetastarch, 20% Hetastarch, 20.5% Hetastarch, 21% Hetastarch, 21.5% Hetastarch, 22% Hetastarch, 22.5% Hetastarch, 23% Hetastarch, 23.5% Hetastarch, 24% Hetastarch, 24.5% Hetastarch, 25% Hetastarch, 25.5% Hetastarch, 26% Hetastarch, 26.5% Hetastarch, 27% Hetastarch, 27.5% Hetastarch, 28% Hetastarch, 28.5% Hetastarch, 29% Hetastarch, 29.5% Hetastarch, 30% Hetastarch, 40% Hetastarch or less than 50% Hetastarch.

In some cases, the concentration of HSA in the cryopreservation medium may be less than 0.1% HSA, 0.2% HSA, 0.3% HSA, 0.4% HSA, 0.5% HSA, 0.6% HSA, 0.7% HSA, 0.8% HSA, 0.9% HSA, 1.0% HSA, 1.1% HSA, 1.2% HSA, 1.3% HSA, 1.4% HSA, 1.5% HSA, 1.6% HSA, 1.7% HSA, 1.8% HSA, 1.9% HSA, 2.0% HSA, 2.1% HSA, 2.2% HSA, 2.3% HSA, 2.4% HSA, 2.5% HSA, 2.6% HSA, 2.7% HSA, 2.8% HSA, 2.9% HSA, 3.0% HSA, 3.1% HSA, 3.2% HSA, 3.3% HSA, 3.4% HSA, 3.5% HSA, 3.6% HSA, 3.7% HSA, 3.8% HSA, 3.9% HSA, 4.0% HSA, 4.1% HSA, 4.2% HSA, 4.3% HSA, 4.4% HSA, 4.5% HSA, 4.6% HSA, 4.7% HSA, 4.8% HSA, 4.9% HSA, 5.0% HSA, 5.1% HSA, 5.2% HSA, 5.3% HSA, 5.4% HSA, 5.5% HSA, 5.6% HSA, 5.7% HSA, 5.8% HSA, 5.9% HSA, 6.0% HSA, 6.1% HSA, 6.2% HSA, 6.3% HSA, 6.4% HSA, 6.5% HSA, 6.6% HSA, 6.7% HSA, 6.8% HSA, 6.9% HSA, 7.0% HSA, 7.1% HSA, 7.2% HSA, 7.3% HSA, 7.4% HSA, 7.5% HSA, 7.6% HSA, 7.7% HSA, 7.8% HSA, 7.9% HSA, 8.0% HSA, 8.1% HSA, 8.2% HSA, 8.3% HSA, 8.4% HSA, 8.5% HSA, 8.6% HSA, 8.7% HSA, 8.8% HSA, 8.9% HSA, 9.0% HSA, 9.1% HSA, 9.2% HSA, 9.3% HSA, 9.4% HSA, 9.5% HSA, 9.6% HSA, 9.7% HSA, 9.8% HSA, 9.9% HSA, 10% HSA, 10.5% HSA, 11% HSA, 11.5% HSA, 12% HSA, 12.5% HSA, 13% HSA, 13.5% HSA, 14% HSA, 14.5% HSA, 15% HSA, 15.5% HSA, 16% HSA, 16.5% HSA, 17% HSA, 17.5% HSA, 18% HSA, 18.5% HSA, 19% HSA, 20% HSA, 20.5% HSA, 21% HSA, 21.5% HSA, 22% HSA, 22.5% HSA, 23% HSA, 23.5% HSA, 24% HSA, 24.5% HSA, 25% HSA, 25.5% HSA, 26% HSA, 26.5% HSA, 27% HSA, 27.5% HSA, 28% HSA, 28.5% HSA, 29% HSA, 29.5% HSA, 30% HSA, 40% HSA or less than 50% HSA.

In some cases, the cryopreservation medium may contain other components in order to cryopreserve the hematopoietic cells in accordance with and for use with the methods described herein.

For the methods described herein, hematopoietic cells can be frozen (e.g., cryopreserved) after isolation or after isolation and purification from the solid organ donor. In some cases, hematopoietic cells may be cryopreserved using a cryopreservation medium and method of cryopreservation known to those of skill in the art. In some cases, the hematopoietic cells may be cryopreserved using a cryopreservation medium containing dimethylsulfoxide (DMSO), fetal calf serum (FCS) and RPMI medium.

In some cases, the concentration of DMSO in the cryopreservation medium may be less than 0.1% DMSO, 0.2% DMSO, 0.3% DMSO, 0.4% DMSO, 0.5% DMSO, 0.6% DMSO, 0.7% DMSO, 0.8% DMSO, 0.9% DMSO, 1.0% DMSO, 1.1% DMSO, 1.2% DMSO, 1.3% DMSO, 1.4% DMSO, 1.5% DMSO, 1.6% DMSO, 1.7% DMSO, 1.8% DMSO, 1.9% DMSO, 2.0% DMSO, 2.1% DMSO, 2.2% DMSO, 2.3% DMSO, 2.4% DMSO, 2.5% DMSO, 2.6% DMSO, 2.7% DMSO, 2.8% DMSO, 2.9% DMSO, 3.0% DMSO, 3.1% DMSO, 3.2% DMSO, 3.3% DMSO, 3.4% DMSO, 3.5% DMSO, 3.5% DMSO, 3.6% DMSO, 3.7% DMSO, 3.8% DMSO, 3.9% DMSO, 4.0% DMSO, 4.1% DMSO, 4.2% DMSO, 4.3% DMSO, 4.4% DMSO, 4.5% DMSO, 4.6% DMSO, 4.7% DMSO, 4.8% DMSO, 4.9% DMSO, 5.0% DMSO, 5.1% DMSO, 5.2% DMSO, 5.3% DMSO, 5.4% DMSO, 5.5% DMSO, 5.6% DMSO, 5.7% DMSO, 5.8% DMSO, 5.9% DMSO, 6.0% DMSO, 6.1% DMSO, 6.2% DMSO, 6.3% DMSO, 6.4% DMSO, 6.5% DMSO, 6.6% DMSO, 6.7% DMSO, 6.8% DMSO, 6.9% DMSO, 7.0% DMSO, 7.1% DMSO, 7.2% DMSO, 7.3% DMSO, 7.4% DMSO, 7.5% DMSO, 7.6% DMSO, 7.7% DMSO, 7.8% DMSO, 7.9% DMSO, 8.0% DMSO, 8.1% DMSO, 8.2% DMSO, 8.3% DMSO, 8.4% DMSO, 8.5% DMSO, 8.6% DMSO, 8.7% DMSO, 8.8% DMSO, 8.9% DMSO, 9.0% DMSO, 9.1% DMSO, 9.2% DMSO, 9.3% DMSO, 9.4% DMSO, 9.5% DMSO, 9.6% DMSO, 9.7% DMSO, 9.8% DMSO, 9.9% DMSO, 10% DMSO, 10.5% DMSO, 11% DMSO, 11.5% DMSO, 12% DMSO, 12.5% DMSO, 13% DMSO, 13.5% DMSO, 14% DMSO, 14.5% DMSO, 15% DMSO, 15.5% DMSO, 16% DMSO, 16.5% DMSO, 17% DMSO, 17.5% DMSO, 18% DMSO, 18.5% DMSO, 19% DMSO, 20% DMSO, 20.5% DMSO, 21% DMSO, 21.5% DMSO, 22% DMSO, 22.5% DMSO, 23% DMSO, 23.5% DMSO, 24% DMSO, 24.5% DMSO, 25% DMSO, 25.5% DMSO, 26% DMSO, 26.5% DMSO, 27% DMSO, 27.5% DMSO, 28% DMSO, 28.5% DMSO, 29% DMSO, 29.5% DMSO, 30% DMSO, 40% DMSO or less than 50% DMSO.

In some cases, the concentration of FCS in the cryopreservation medium may be greater than 1.0% FCS, 2.0% FCS, 3.0% FCS, 4.0% FCS, 5.0% FCS, 6.0% FCS, 7.0% FCS, 8.0% FCS, 9.0% FCS, 10% FCS, 10.5% FCS, 11% FCS, 11.5% FCS, 12% FCS, 12.5% FCS, 13% FCS, 13.5% FCS, 14% FCS, 14.5% FCS, 15% FCS, 15.5% FCS, 16% FCS, 16.5% FCS, 17% FCS, 17.5% FCS, 18% FCS, 18.5% FCS, 19% FCS, 20% FCS, 20.5% FCS, 21% FCS, 21.5% FCS, 22% FCS, 22.5% FCS, 23% FCS, 23.5% FCS, 24% FCS, 24.5% FCS, 25% FCS, 25.5% FCS, 26% FCS, 26.5% FCS, 27% FCS, 27.5% FCS, 28% FCS, 28.5% FCS, 29% FCS, 29.5% FCS, 30% FCS, 30.5% FCS, 31% FCS, 31.5% FCS, 32% FCS, 32.5% FCS, 33% FCS, 33.5% FCS, 34% FCS, 34.5% FCS, 35% FCS, 35.5% FCS, 36% FCS, 36.5% FCS, 37% FCS, 37.5% FCS, 38% FCS, 38.5% FCS, 39% FCS, 40% FCS, 40.5% FCS, 41% FCS, 41.5% FCS, 42% FCS, 42.5% FCS, 43% FCS, 43.5% FCS, 44% FCS, 44.5% FCS, 45% FCS, 45.5% FCS, 46% FCS, 46.5% FCS, 47% FCS, 47.5% FCS, 48% FCS, 48.5% FCS, 49% FCS, 50% FCS, 50.5% FCS, 51% FCS, 51.5% FCS, 52% FCS, 52.5% FCS, 53% FCS, 53.5% FCS, 54% FCS, 54.5% FCS, 55% FCS, 55.5% FCS, 56% FCS, 56.5% FCS, 57% FCS, 57.5% FCS, 58% FCS, 58.5% FCS, 59% FCS, 60% FCS, 60.5% FCS, 61% FCS, 61.5% FCS, 62% FCS, 62.5% FCS, 63% FCS, 63.5% FCS, 64% FCS, 64.5% FCS, 65% FCS, 65.5% FCS, 66% FCS, 66.5% FCS, 67% FCS, 67.5% FCS, 68% FCS, 68.5% FCS, 69% FCS, 70% FCS, 70.5% FCS, 71% FCS, 71.5% FCS, 72% FCS, 72.5% FCS, 73% FCS, 73.5% FCS, 74% FCS, 74.5% FCS, 75% FCS, 75.5% FCS, 76% FCS, 76.5% FCS, 77% FCS, 77.5% FCS, 78% FCS, 78.5% FCS, 79% FCS or greater than 80% FCS.

In some cases, the concentration of RPMI in the cryopreservation medium may be greater than 1.0% RPMI, 2.0% RPMI, 3.0% RPMI, 4.0% RPMI, 5.0% RPMI, 6.0% RPMI, 7.0% RPMI, 8.0% RPMI, 9.0% RPMI, 10% RPMI, 10.5% RPMI, 11% RPMI, 11.5% RPMI, 12% RPMI, 12.5% RPMI, 13% RPMI, 13.5% RPMI, 14% RPMI, 14.5% RPMI, 15% RPMI, 15.5% RPMI, 16% RPMI, 16.5% RPMI, 17% RPMI, 17.5% RPMI, 18% RPMI, 18.5% RPMI, 19% RPMI, 20% RPMI, 20.5% RPMI, 21% RPMI, 21.5% RPMI, 22% RPMI, 22.5% RPMI, 23% RPMI, 23.5% RPMI, 24% RPMI, 24.5% RPMI, 25% RPMI, 25.5% RPMI, 26% RPMI, 26.5% RPMI, 27% RPMI, 27.5% RPMI, 28% RPMI, 28.5% RPMI, 29% RPMI, 29.5% RPMI, 30% RPMI, 30.5% RPMI, 31% RPMI, 31.5% RPMI, 32% RPMI, 32.5% RPMI, 33% RPMI, 33.5% RPMI, 34% RPMI, 34.5% RPMI, 35% RPMI, 35.5% RPMI, 36% RPMI, 36.5% RPMI, 37% RPMI, 37.5% RPMI, 38% RPMI, 38.5% RPMI, 39% RPMI, 40% RPMI, 40.5% RPMI, 41% RPMI, 41.5% RPMI, 42% RPMI, 42.5% RPMI, 43% RPMI, 43.5% RPMI, 44% RPMI, 44.5% RPMI, 45% RPMI, 45.5% RPMI, 46% RPMI, 46.5% RPMI, 47% RPMI, 47.5% RPMI, 48% RPMI, 48.5% RPMI, 49% RPMI, 50% RPMI, 50.5% RPMI, 51% RPMI, 51.5% RPMI, 52% RPMI, 52.5% RPMI, 53% RPMI, 53.5% RPMI, 54% RPMI, 54.5% RPMI, 55% RPMI, 55.5% RPMI, 56% RPMI, 56.5% RPMI, 57% RPMI, 57.5% RPMI, 58% RPMI, 58.5% RPMI, 59% RPMI, 60% RPMI, 60.5% RPMI, 61% RPMI, 61.5% RPMI, 62% RPMI, 62.5% RPMI, 63% RPMI, 63.5% RPMI, 64% RPMI, 64.5% RPMI, 65% RPMI, 65.5% RPMI, 66% RPMI, 66.5% RPMI, 67% RPMI, 67.5% RPMI, 68% RPMI, 68.5% RPMI, 69% RPMI, 70% RPMI, 70.5% RPMI, 71% RPMI, 71.5% RPMI, 72% RPMI, 72.5% RPMI, 73% RPMI, 73.5% RPMI, 74% RPMI, 74.5% RPMI, 75% RPMI, 75.5% RPMI, 76% RPMI, 76.5% RPMI, 77% RPMI, 77.5% RPMI, 78% RPMI, 78.5% RPMI, 79% RPMI or greater than 80% RPMI.

In some cases, the cryopreservation medium may contain other components in order to cryopreserve the hematopoietic cells in accordance with and for use with the methods described herein.

Cryopreservation of hematopoietic cells includes a process of controlled rate freezing the cells once contained within cryopreservation medium. In some cases, a cryofreezer equipped with a computer to control the rate and temperatures of controlled rate freezing can be used to perform cryopreservation of the hematopoietic cells. For example, the hematopoietic cells may be placed in a cryofreezer with a chamber temperature at or below 6.5° C. The computer may control the rate and temperatures of controlled rate freezing such that the cryofreezer reaches a temperature of at least or below −130° C. such that the hematopoietic cells are preserved in manner in accordance with the methods described herein. In some cases, the cryofreezer uses liquid nitrogen to control the temperature of the freezer at which the hematopoietic cells are stored.

In some cases, the hematopoietic cells may be cryopreserved and stored in a cryofreezer prior to delivery to the recipient. In some cases, the hematopoietic cells may be cryopreserved for less than one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days or less than 60 days.

In some cases, the hematopoietic cells may be cryopreserved for less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months, 51 months, 52 months, 53 months, 54 months, 55 months, 56 months, 57 months, 58 months, 59 months or less than 60 months.

In some cases, the hematopoietic cells may be cryopreserved for less than one year, two years, three years, four years, five years, six years, seven years, eight years, nine years, ten years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 51 years, 52 years, 53 years, 54 years, 55 years, 56 years, 57 years, 58 years, 59 years or less than 60 years.

In some cases, the hematopoietic cells may be cryopreserved for more than one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days or more 60 days.

In some cases, the hematopoietic cells may be cryopreserved for more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months, 51 months, 52 months, 53 months, 54 months, 55 months, 56 months, 57 months, 58 months, 59 months or for more than 60 months.

In some cases, the hematopoietic cells may be cryopreserved for more than one year, two years, three years, four years, five years, six years, seven years, eight years, nine years, ten years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 51 years, 52 years, 53 years, 54 years, 55 years, 56 years, 57 years, 58 years, 59 years or more than 60 years.

In some cases, cryopreservation may result in hematopoietic cell death which is determined upon thawing of the cells prior to infusion into the recipient. Using conventional methods of determining cell death (e.g., trypan blue staining, flow cytometry, etc.) known to those of skill in the art, the percent of dead cells in batch of cryopreserved hematopoietic cells may be determined. In some cases, after thawing cryopreserved cells, there may be less than 0.1% dead cells, 0.2% dead cells, 0.3% dead cells, 0.4% dead cells, 0.5% dead cells, 0.6% dead cells, 0.7% dead cells, 0.8% dead cells, 0.9% dead cells, 1.0% dead cells, 1.1% dead cells, 1.2% dead cells, 1.3% dead cells, 1.4% dead cells, 1.5% dead cells, 1.6% dead cells, 1.7% dead cells, 1.8% dead cells, 1.9% dead cells, 2.0% dead cells, 2.1% dead cells, 2.2% dead cells, 2.3% dead cells, 2.4% dead cells, 2.5% dead cells, 2.6% dead cells, 2.7% dead cells, 2.8% dead cells, 2.9% dead cells, 3.0% dead cells, 3.1% dead cells, 3.2% dead cells, 3.3% dead cells, 3.4% dead cells, 3.5% dead cells, 3.6% dead cells, 3.7% dead cells, 3.8% dead cells, 3.9% dead cells, 4.0% dead cells, 4.1% dead cells, 4.2% dead cells, 4.3% dead cells, 4.4% dead cells, 4.5% dead cells, 4.6% dead cells, 4.7% dead cells, 4.8% dead cells, 4.9% dead cells, 5.0% dead cells, 5.1% dead cells, 5.2% dead cells, 5.3% dead cells, 5.4% dead cells, 5.5% dead cells, 5.6% dead cells, 5.7% dead cells, 5.8% dead cells, 5.9% dead cells, 6.0% dead cells, 6.1% dead cells, 6.2% dead cells, 6.3% dead cells, 6.4% dead cells, 6.5% dead cells, 6.6% dead cells, 6.7% dead cells, 6.8% dead cells, 6.9% dead cells, 7.0% dead cells, 7.1% dead cells, 7.2% dead cells, 7.3% dead cells, 7.4% dead cells, 7.5% dead cells, 7.6% dead cells, 7.7% dead cells, 7.8% dead cells, 7.9% dead cells, 8.0% dead cells, 8.1% dead cells, 8.2% dead cells, 8.3% dead cells, 8.4% dead cells, 8.5% dead cells, 8.6% dead cells, 8.7% dead cells, 8.8% dead cells, 8.9% dead cells, 9.0% dead cells, 9.1% dead cells, 9.2% dead cells, 9.3% dead cells, 9.4% dead cells, 9.5% dead cells, 9.6% dead cells, 9.7% dead cells, 9.8% dead cells, 9.9% dead cells, 10% dead cells, 10.5% dead cells, 11% dead cells, 11.5% dead cells, 12% dead cells, 12.5% dead cells, 13% dead cells, 13.5% dead cells, 14% dead cells, 14.5% dead cells, 15% dead cells, 15.5% dead cells, 16% dead cells, 16.5% dead cells, 17% dead cells, 17.5% dead cells, 18% dead cells, 18.5% dead cells, 19% dead cells, 20% dead cells, 20.5% dead cells, 21% dead cells, 21.5% dead cells, 22% dead cells, 22.5% dead cells, 23% dead cells, 23.5% dead cells, 24% dead cells, 24.5% dead cells, 25% dead cells, 25.5% dead cells, 26% dead cells, 26.5% dead cells, 27% dead cells, 27.5% dead cells, 28% dead cells, 28.5% dead cells, 29% dead cells, 29.5% dead cells, 30% dead cells, 40% dead cells or less than 50% dead cells.

Isolation and Purification of Hematopoietic Stem Cells

For the methods described herein, hematopoietic stem cells may be derived from bone marrow, peripheral blood, or umbilical cord blood. In some cases, the hematopoietic stem cells may be HLA-matched between the donor and the recipient. In other cases, the hematopoietic stem cells may be HLA-mismatched between the donor and the recipient.

In some cases, specific types of cells may be isolated and purified from the hematopoietic stem cells. In some cases, the cells that may be isolated and purified from the hematopoietic stem cells are CD34+ cells and CD3+ cells. In some cases, the CD34+ and CD3+ cells are isolated from the same fraction of hematopoietic stem cells. In some cases, the CD34+ and CD3+ cells are isolated from a different fraction of hematopoietic stem cells. In some cases, the CD34+ cells are progenitor cells. In some cases, the CD3+ cells are T cells.

In some cases, CD34+ cells are isolated and purified from the donor hematopoietic cells. For example, CD34+ cells may be isolated and purified from the donor hematopoietic cells by selectively binding a suitable CD34 affinity reagent. In some cases, a CD34 affinity reagent may be an antibody, a full-length antibody, a fragment of an antibody, a naturally occurring antibody, a synthetic antibody, an engineered antibody, a full-length affibody, a fragment of an affibody, a full-length affilin, a fragment of an affilin, a full-length anticalin, a fragment of an anticalin, a full-length avimer, a fragment of an avimer, a full-length DARPin, a fragment of a DARPin, a full-length fynomer, a fragment of a fynomer, a full-length kunitz domain peptide, a fragment of a kunitz domain peptide, a full-length monobody, a fragment of a monobody, a peptide, a polyaminoacid, or the like.

In some cases, the affinity reagent is directly conjugated to a detection reagent and/or purification reagent. In some cases, the detection reagent and purification reagent are the same. In other cases, the detection reagent and purification reagent are different. For example, the detection reagent and/or purification reagent is fluorescent, magnetic, or the like. In some cases, the detection reagent and/or purification reagent is a magnetic particle for column purification. For example, magnetic column purification may be performed using the Miltenyi system of columns, antibodies, buffers, preparation materials and reagents, etc. known to those of skill in the art.

In some cases, CD34+ cells isolated and purified using a magnetic particle may contain iron. The iron content of isolated and purified CD34+ cells may be greater after isolation and purification using magnetic particles than the iron content in the CD34+ cells prior to isolation and purification. For example, isolated and purified CD34+ cells may contain less than 500 pg of iron/cell, 450 pg of iron/cell, 400 pg of iron/cell, 350 pg of iron/cell, 300 pg of iron/cell, 250 pg of iron/cell, 225 pg of iron/cell, 200 pg of iron/cell, 190 pg of iron/cell, 180 pg of iron/cell, 170 pg of iron/cell, 160 pg of iron/cell, 150 pg of iron/cell, 140 pg of iron/cell, 130 pg of iron/cell, 120 pg of iron/cell, 110 pg of iron/cell, 109 pg of iron/cell, 108 pg of iron/cell, 107 pg of iron/cell, 106 pg of iron/cell, 105 pg of iron/cell, 104 pg of iron/cell, 103 pg of iron/cell, 102 pg of iron/cell, 101 pg of iron/cell, 100 pg of iron/cell, 99 pg of iron/cell, 98 pg of iron/cell, 97 pg of iron/cell, 96 pg of iron/cell, 95 pg of iron/cell, 94 pg of iron/cell, 93 pg of iron/cell, 92 pg of iron/cell, 91 pg of iron/cell, 90 pg of iron/cell, 89 pg of iron/cell, 88 pg of iron/cell, 87 pg of iron/cell, 86 pg of iron/cell, 85 pg of iron/cell, 84 pg of iron/cell, 83 pg of iron/cell, 82 pg of iron/cell, 81 pg of iron/cell, 80 pg of iron/cell, 79 pg of iron/cell, 78 pg of iron/cell, 77 pg of iron/cell, 76 pg of iron/cell, 75 pg of iron/cell, 74 pg of iron/cell, 73 pg of iron/cell, 72 pg of iron/cell, 71 pg of iron/cell, 70 pg of iron/cell, 69 pg of iron/cell, 68 pg of iron/cell, 67 pg of iron/cell, 66 pg of iron/cell, 65 pg of iron/cell, 64 pg of iron/cell, 63 pg of iron/cell, 62 pg of iron/cell, 61 pg of iron/cell, 60 pg of iron/cell, 59 pg of iron/cell, 58 pg of iron/cell, 57 pg of iron/cell, 56 pg of iron/cell, 55 pg of iron/cell, 54 pg of iron/cell, 53 pg of iron/cell, 52 pg of iron/cell, 51 pg of iron/cell, 50 pg of iron/cell, 49 pg of iron/cell, 48 pg of iron/cell, 47 pg of iron/cell, 46 pg of iron/cell, 45 pg of iron/cell, 44 pg of iron/cell, 43 pg of iron/cell, 42 pg of iron/cell, 41 pg of iron/cell, 40 pg of iron/cell, 39 pg of iron/cell, 38 pg of iron/cell, 37 pg of iron/cell, 36 pg of iron/cell, 35 pg of iron/cell, 34 pg of iron/cell, 33 pg of iron/cell, 32 pg of iron/cell, 31 pg of iron/cell, 30 pg of iron/cell, 29 pg of iron/cell, 28 pg of iron/cell, 27 pg of iron/cell, 26 pg of iron/cell, 25 pg of iron/cell, 24 pg of iron/cell, 23 pg of iron/cell, 22 pg of iron/cell, 21 pg of iron/cell, 20 pg of iron/cell, 19 pg of iron/cell, 18 pg of iron/cell, 17 pg of iron/cell, 16 pg of iron/cell, 15 pg of iron/cell, 14 pg of iron/cell, 13 pg of iron/cell, 12 pg of iron/cell, 11 pg of iron/cell, 10 pg of iron/cell, 9 pg of iron/cell, 8 pg of iron/cell, 7 pg of iron/cell, 6 pg of iron/cell, 5 pg of iron/cell, 4 pg of iron/cell, 3 pg of iron/cell, 2 pg of iron/cell, or less than 1 pg of iron/cell.

In some cases, CD3+ cells are isolated and purified from the donor hematopoietic cells. For example, CD3+ cells may be isolated and purified from the donor hematopoietic cells by selectively binding a suitable CD3 affinity reagent. In some cases, a CD3 affinity reagent may be an antibody, a full-length antibody, a fragment of an antibody, a naturally occurring antibody, a synthetic antibody, an engineered antibody, a full-length affibody, a fragment of an affibody, a full-length affilin, a fragment of an affilin, a full-length anticalin, a fragment of an anticalin, a full-length avimer, a fragment of an avimer, a full-length DARPin, a fragment of a DARPin, a full-length fynomer, a fragment of a fynomer, a full-length kunitz domain peptide, a fragment of a kunitz domain peptide, a full-length monobody, a fragment of a monobody, a peptide, a polyaminoacid, or the like.

In some cases, the affinity reagent is directly conjugated to a detection reagent and/or purification reagent. In some cases, the detection reagent and purification reagent are the same. In other cases, the detection reagent and purification reagent are different. For example, the detection reagent and/or purification reagent is fluorescent, magnetic, or the like. In some cases, the detection reagent and/or purification reagent is a magnetic particle for column purification. For example, magnetic column purification may be performed using the Miltenyi system of columns, antibodies, buffers, preparation materials and reagents, etc. known to those of skill in the art.

The CD3+ cells may be selected from one of two cell populations. In some cases, the apheresis product may be split into two portions, one portion used to isolate and purify CD3+ cells and the other portion to isolate and purify CD34+ cells. In some cases, CD34+ cells are isolated and purified from the apheresis product creating a CD34-negative cell fraction. In some cases, the number of CD3+ cells in the CD34-negative fraction can be determined and a volume of the CD34-negative fraction containing an appropriate dose of CD3 cells combined with a volume of isolated and purified CD34+ cells. For example, CD34+ cells and the CD3+ cells are isolated from the at least one apheresis product using at least an affinity agent and a column, the CD34+ cells located in an eluate from the column and the CD3+ cells located in a CD34-depleted flow-through fraction from the column. In another example, the CD34-depleted fraction of the apheresis product is the CD34-depleted flow-through fraction from an affinity column.

In some cases, the number of CD3+ cells in the negative fraction can be determined using an affinity reagent for CD3+. For example, an affinity reagent may be an antibody, a peptide or the like previously described in the disclosure. In some cases, the affinity reagent may include a detection moiety. For example, a detection moiety may be fluorescent, magnetic or the like previously described in the disclosure.

In some cases, CD3+ cells isolated and purified using a magnetic particle may contain iron. The iron content of isolated and purified CD3+ cells may be greater after isolation and purification using magnetic particles than the iron content in the CD3+ cells prior to isolation and purification. For example, isolated and purified CD3+ cells may contain less than 500 pg of iron/cell, 450 pg of iron/cell, 400 pg of iron/cell, 350 pg of iron/cell, 300 pg of iron/cell, 250 pg of iron/cell, 225 pg of iron/cell, 200 pg of iron/cell, 190 pg of iron/cell, 180 pg of iron/cell, 170 pg of iron/cell, 160 pg of iron/cell, 150 pg of iron/cell, 140 pg of iron/cell, 130 pg of iron/cell, 120 pg of iron/cell, 110 pg of iron/cell, 109 pg of iron/cell, 108 pg of iron/cell, 107 pg of iron/cell, 106 pg of iron/cell, 105 pg of iron/cell, 104 pg of iron/cell, 103 pg of iron/cell, 102 pg of iron/cell, 101 pg of iron/cell, 100 pg of iron/cell, 99 pg of iron/cell, 98 pg of iron/cell, 97 pg of iron/cell, 96 pg of iron/cell, 95 pg of iron/cell, 94 pg of iron/cell, 93 pg of iron/cell, 92 pg of iron/cell, 91 pg of iron/cell, 90 pg of iron/cell, 89 pg of iron/cell, 88 pg of iron/cell, 87 pg of iron/cell, 86 pg of iron/cell, 85 pg of iron/cell, 84 pg of iron/cell, 83 pg of iron/cell, 82 pg of iron/cell, 81 pg of iron/cell, 80 pg of iron/cell, 79 pg of iron/cell, 78 pg of iron/cell, 77 pg of iron/cell, 76 pg of iron/cell, 75 pg of iron/cell, 74 pg of iron/cell, 73 pg of iron/cell, 72 pg of iron/cell, 71 pg of iron/cell, 70 pg of iron/cell, 69 pg of iron/cell, 68 pg of iron/cell, 67 pg of iron/cell, 66 pg of iron/cell, 65 pg of iron/cell, 64 pg of iron/cell, 63 pg of iron/cell, 62 pg of iron/cell, 61 pg of iron/cell, 60 pg of iron/cell, 59 pg of iron/cell, 58 pg of iron/cell, 57 pg of iron/cell, 56 pg of iron/cell, 55 pg of iron/cell, 54 pg of iron/cell, 53 pg of iron/cell, 52 pg of iron/cell, 51 pg of iron/cell, 50 pg of iron/cell, 49 pg of iron/cell, 48 pg of iron/cell, 47 pg of iron/cell, 46 pg of iron/cell, 45 pg of iron/cell, 44 pg of iron/cell, 43 pg of iron/cell, 42 pg of iron/cell, 41 pg of iron/cell, 40 pg of iron/cell, 39 pg of iron/cell, 38 pg of iron/cell, 37 pg of iron/cell, 36 pg of iron/cell, 35 pg of iron/cell, 34 pg of iron/cell, 33 pg of iron/cell, 32 pg of iron/cell, 31 pg of iron/cell, 30 pg of iron/cell, 29 pg of iron/cell, 28 pg of iron/cell, 27 pg of iron/cell, 26 pg of iron/cell, 25 pg of iron/cell, 24 pg of iron/cell, 23 pg of iron/cell, 22 pg of iron/cell, 21 pg of iron/cell, 20 pg of iron/cell, 19 pg of iron/cell, 18 pg of iron/cell, 17 pg of iron/cell, 16 pg of iron/cell, 15 pg of iron/cell, 14 pg of iron/cell, 13 pg of iron/cell, 12 pg of iron/cell, 11 pg of iron/cell, 10 pg of iron/cell, 9 pg of iron/cell, 8 pg of iron/cell, 7 pg of iron/cell, 6 pg of iron/cell, 5 pg of iron/cell, 4 pg of iron/cell, 3 pg of iron/cell, 2 pg of iron/cell, or less than 1 pg of iron/cell.

In some cases, both of the CD34+ and CD3+ cells isolated and purified using a magnetic particle may contain iron. The iron content of isolated and purified CD34+ and CD3+ cells may be greater after isolation and purification using magnetic particles than the iron content in the CD34+ and CD3+ cells prior to isolation and purification. For example, isolated and purified CD34+ and CD3+ cells may contain less than 500 pg of iron/cell, 450 pg of iron/cell, 400 pg of iron/cell, 350 pg of iron/cell, 300 pg of iron/cell, 250 pg of iron/cell, 225 pg of iron/cell, 200 pg of iron/cell, 190 pg of iron/cell, 180 pg of iron/cell, 170 pg of iron/cell, 160 pg of iron/cell, 150 pg of iron/cell, 140 pg of iron/cell, 130 pg of iron/cell, 120 pg of iron/cell, 110 pg of iron/cell, 109 pg of iron/cell, 108 pg of iron/cell, 107 pg of iron/cell, 106 pg of iron/cell, 105 pg of iron/cell, 104 pg of iron/cell, 103 pg of iron/cell, 102 pg of iron/cell, 101 pg of iron/cell, 100 pg of iron/cell, 99 pg of iron/cell, 98 pg of iron/cell, 97 pg of iron/cell, 96 pg of iron/cell, 95 pg of iron/cell, 94 pg of iron/cell, 93 pg of iron/cell, 92 pg of iron/cell, 91 pg of iron/cell, 90 pg of iron/cell, 89 pg of iron/cell, 88 pg of iron/cell, 87 pg of iron/cell, 86 pg of iron/cell, 85 pg of iron/cell, 84 pg of iron/cell, 83 pg of iron/cell, 82 pg of iron/cell, 81 pg of iron/cell, 80 pg of iron/cell, 79 pg of iron/cell, 78 pg of iron/cell, 77 pg of iron/cell, 76 pg of iron/cell, 75 pg of iron/cell, 74 pg of iron/cell, 73 pg of iron/cell, 72 pg of iron/cell, 71 pg of iron/cell, 70 pg of iron/cell, 69 pg of iron/cell, 68 pg of iron/cell, 67 pg of iron/cell, 66 pg of iron/cell, 65 pg of iron/cell, 64 pg of iron/cell, 63 pg of iron/cell, 62 pg of iron/cell, 61 pg of iron/cell, 60 pg of iron/cell, 59 pg of iron/cell, 58 pg of iron/cell, 57 pg of iron/cell, 56 pg of iron/cell, 55 pg of iron/cell, 54 pg of iron/cell, 53 pg of iron/cell, 52 pg of iron/cell, 51 pg of iron/cell, 50 pg of iron/cell, 49 pg of iron/cell, 48 pg of iron/cell, 47 pg of iron/cell, 46 pg of iron/cell, 45 pg of iron/cell, 44 pg of iron/cell, 43 pg of iron/cell, 42 pg of iron/cell, 41 pg of iron/cell, 40 pg of iron/cell, 39 pg of iron/cell, 38 pg of iron/cell, 37 pg of iron/cell, 36 pg of iron/cell, 35 pg of iron/cell, 34 pg of iron/cell, 33 pg of iron/cell, 32 pg of iron/cell, 31 pg of iron/cell, 30 pg of iron/cell, 29 pg of iron/cell, 28 pg of iron/cell, 27 pg of iron/cell, 26 pg of iron/cell, 25 pg of iron/cell, 24 pg of iron/cell, 23 pg of iron/cell, 22 pg of iron/cell, 21 pg of iron/cell, 20 pg of iron/cell, 19 pg of iron/cell, 18 pg of iron/cell, 17 pg of iron/cell, 16 pg of iron/cell, 15 pg of iron/cell, 14 pg of iron/cell, 13 pg of iron/cell, 12 pg of iron/cell, 11 pg of iron/cell, 10 pg of iron/cell, 9 pg of iron/cell, 8 pg of iron/cell, 7 pg of iron/cell, 6 pg of iron/cell, 5 pg of iron/cell, 4 pg of iron/cell, 3 pg of iron/cell, 2 pg of iron/cell, or less than 1 pg of iron/cell.

Engineering and Preparing Hematopoietic Stem Cells for Pharmaceutical Compositions A combination of CD34+ and CD3+ cells derived from the donor using the methods described herein may be engineered into a pharmaceutical composition for administration to the solid organ recipient. In some cases, the hematopoietic cells may be engineered into a single pharmaceutical composition for infusion into a recipient. In other cases, the hematopoietic cells may be engineered into multiple pharmaceutical compositions for infusion into a recipient. In some cases, the CD34+ and CD3+ cells may be HLA-matched between the donor and the recipient. In other cases, the CD34+ and CD3+ cells may be HLA-mismatched between the donor and the recipient.

In some cases, the hematopoietic cells may be engineered into a pharmaceutical composition having a pre-determined purity of CD34+ hematopoietic cells. For example, the purity of the CD34+ progenitor cells in the engineered hematopoietic cells may be ≥30% purity, ≥40% purity, ≥50% purity, ≥55% purity, ≥60% purity, ≥65% purity, ≥70% purity, ≥75% purity, ≥80% purity, ≥85% purity, ≥90% purity, ≥95% purity or ≥98% purity. In an another example, the purity of the CD34+ progenitor cells in the engineered hematopoietic cells may be between 10 and 30% purity, 15 and 35% purity, 20 and 40% purity, 25 and 45% purity, 30 and 50% purity, 35 and 55% purity, 40 and 60% purity, 45 and 65% purity, 50 and 70% purity, 55 and 75% purity, 60 and 80% purity, 65 and 85% purity, 70 and 90% purity, 75 and 95% purity, and 80 and 100% purity. In an exemplary case, the purity of the CD34+ progenitor cells in the engineered hematopoietic cells is ≥70% purity.

For example, the purity of the CD3+ cells in the engineered hematopoietic cells may be ≥30% purity, ≥40% purity, ≥50% purity, ≥55% purity, ≥60% purity, ≥65% purity, ≥70% purity, ≥75% purity, ≥80% purity, ≥85% purity, ≥90% purity, ≥95% purity or ≥98% purity. In an another example, the purity of the CD3+ cells in the engineered hematopoietic cells may be between 10 and 30% purity, 15 and 35% purity, 20 and 40% purity, 25 and 45% purity, 30 and 50% purity, 35 and 55% purity, 40 and 60% purity, 45 and 65% purity, 50 and 70% purity, 55 and 75% purity, 60 and 80% purity, 65 and 85% purity, 70 and 90% purity, 75 and 95% purity, and 80 and 100% purity. In an exemplary case, the purity of the CD3+ cells in the engineered hematopoietic cells is ≥70% purity prior to combining with the CD34+ cells.

In some cases, the hematopoietic cells may be engineered into a product having a pre-determined purity of CD34+ progenitor cells. For example, the purity of the CD34+ progenitor cells in the engineered hematopoietic cells may be ≥30% purity, ≥40% purity, ≥50% purity, ≥55% purity, ≥60% purity, ≥65% purity, ≥70% purity, ≥75% purity, ≥80% purity, ≥85% purity, ≥90% purity, ≥95% purity or ≥98% purity. In an another example, the purity of the CD34+ progenitor cells in the engineered hematopoietic cells may be between 10 and 30% purity, 15 and 35% purity, 20 and 40% purity, 25 and 45% purity, 30 and 50% purity, 35 and 55% purity, 40 and 60% purity, 45 and 65% purity, 50 and 70% purity, 55 and 75% purity, 60 and 80% purity, 65 and 85% purity, 70 and 90% purity, 75 and 95% purity, and 80 and 100% purity. In an exemplary case, the purity of the CD34+ progenitor cells in the engineered hematopoietic cells is ≥70% purity prior to combining with the CD3+ cells.

The engineered hematopoietic cells may contain a specific number of CD34+ cells for injection into a recipient. In some cases, the target dose of CD34+ cells to be injected into a recipient is ≥10×10$^3$ cells/kg of body weight, ≥15×10$^3$ cells/kg of body weight, ≥20×10$^3$ cells/kg of body weight, ≥25×10$^3$ cells/kg of body weight, ≥30×10$^3$ cells/kg of body weight, ≥35×10$^3$ cells/kg of body weight, ≥40×10$^3$ cells/kg of body weight, ≥45×10$^3$ cells/kg of body weight, ≥50×10$^3$ cells/kg of body weight, ≥55×10$^3$ cells/kg of body weight, ≥60×10$^3$ cells/kg of body weight, ≥65×10$^3$ cells/kg of body weight, ≥70×10$^3$ cells/kg of body weight, ≥75×10$^3$ cells/kg of body weight, ≥80×10$^3$ cells/kg of body weight, ≥85×10$^3$ cells/kg of body weight, 90×10$^3$ cells/kg of body weight, ≥95×10$^3$ cells/kg of body weight, ≥10×10$^4$ cells/kg of body weight, ≥15×10$^4$ cells/kg of body weight, ≥20×10$^4$ cells/kg of body weight, ≥25×10$^4$ cells/kg of body weight, ≥30×10$^4$ cells/kg of body weight, ≥35×10$^4$ cells/kg of body weight, ≥40×10$^4$ cells/kg of body weight, ≥45×10$^4$ cells/kg of body weight, ≥50×10$^4$ cells/kg of body weight, ≥55×10$^4$ cells/kg of body weight, ≥60×10$^4$ cells/kg of body weight, ≥65×10$^4$ cells/kg of body weight, ≥70×10$^4$ cells/kg of body weight, ≥75×10$^4$ cells/kg of body weight, ≥80×10$^4$ cells/kg of body weight, ≥85×10$^4$ cells/kg of body weight, 90×10$^4$ cells/kg of body weight, ≥95×10$^4$ cells/kg of body weight, ≥10×10$^5$ cells/kg of body weight, ≥15×10$^5$ cells/kg of body weight, ≥20×10$^5$ cells/kg of body weight, ≥25×10$^5$ cells/kg of body weight, ≥30×10$^5$ cells/kg of body weight, ≥35×10$^5$ cells/kg of body weight, ≥40×10$^5$ cells/kg of body weight, ≥45×10$^5$ cells/kg of body weight, ≥50×10$^5$ cells/kg of body weight, ≥55×10$^5$ cells/kg of body weight, ≥60×10$^5$ cells/kg of body weight, ≥65×10$^5$ cells/kg of body weight, ≥70×10$^5$ cells/kg of body weight, ≥75×10$^5$ cells/kg of body weight, ≥80×10$^5$ cells/kg of body weight, ≥85×10$^5$ cells/kg of body weight, 90×10$^5$ cells/kg of body weight, ≥95×10$^5$ cells/kg of body weight, ≥10×10$^6$ cells/kg of body weight, ≥15×10$^6$ cells/kg of body weight, ≥20×10$^6$ cells/kg of body weight, ≥25×10$^6$ cells/kg of body weight, ≥30×10⁶ cells/kg of body weight, ≥35×10⁶ cells/kg of body weight, ≥40×10⁶ cells/kg of body weight, ≥45×10⁶ cells/kg of body weight, ≥50×10⁶ cells/kg of body weight, ≥55×10⁶ cells/kg of body weight, ≥60×10⁶ cells/kg of body weight, ≥65×10⁶ cells/kg of body weight, ≥70×10⁶ cells/kg of body weight, ≥75×10⁶ cells/kg of body weight, ≥80×10⁶ cells/kg of body weight, ≥85×10⁶ cells/kg of body weight, 90×10⁶ cells/kg of body weight, ≥95×10⁶ cells/kg of body weight, ≥10×10⁷ cells/kg of body weight, ≥15×10⁷ cells/kg of body weight, ≥20×10⁷ cells/kg of body weight, ≥25×10⁷ cells/kg of body weight, ≥30×10⁷ cells/kg of body weight, ≥35×10⁷ cells/kg of body weight, ≥40×10⁷ cells/kg of body weight, ≥45×10⁷ cells/kg of body weight, ≥50×10⁷ cells/kg of body weight, ≥55×10⁷ cells/kg of body weight, ≥60×10⁷ cells/kg of body weight, ≥65×10⁷ cells/kg of body weight, ≥70×10⁷ cells/kg of body weight, ≥75×10⁷ cells/kg of body weight, ≥80×10⁷ cells/kg of body weight, ≥85×10⁷ cells/kg of body weight, 90×10⁷ cells/kg of body weight, ≥95×10⁷ cells/kg of body weight, ≥10×10⁸ cells/kg of body weight, ≥15×10⁸ cells/kg of body weight, ≥20×10⁸ cells/kg of body weight, ≥25×10⁸ cells/kg of body weight, ≥30×10⁸ cells/kg of body weight, ≥35×10⁸ cells/kg of body weight, ≥40×10⁸ cells/kg of body weight, ≥45×10⁸ cells/kg of body weight, ≥50×10⁸ cells/kg of body weight, ≥55×10⁸ cells/kg of body weight, ≥60×10⁸ cells/kg of body weight, ≥65×10⁸ cells/kg of body weight, ≥70×10⁸ cells/kg of body weight, ≥75×10⁸ cells/kg of body weight, ≥80×10⁸ cells/kg of body weight, ≥85×10⁸ cells/kg of body weight, 90×10⁸ cells/kg of body weight, ≥95×10⁸ cells/kg of body weight or ≥10×10⁹ cells/kg of body weight.

The engineered hematopoietic cells may contain a specific number of CD3+ cells for injection into a recipient. In some cases, the target dose of CD3+ cells to be injected into a recipient is ≥10×10³ cells/kg of body weight, ≥15×10³ cells/kg of body weight, ≥20×10³ cells/kg of body weight, ≥25×10³ cells/kg of body weight, ≥30×10³ cells/kg of body weight, ≥35×10³ cells/kg of body weight, ≥40×10³ cells/kg of body weight, ≥45×10³ cells/kg of body weight, ≥50×10³ cells/kg of body weight, ≥55×10³ cells/kg of body weight, ≥60×10³ cells/kg of body weight, ≥65×10³ cells/kg of body weight, ≥70×10³ cells/kg of body weight, ≥75×10³ cells/kg of body weight, ≥80×10³ cells/kg of body weight, ≥85×10³ cells/kg of body weight, 90×10³ cells/kg of body weight, ≥95×10³ cells/kg of body weight, ≥10×10⁴ cells/kg of body weight, ≥15×10⁴ cells/kg of body weight, ≥20×10⁴ cells/kg of body weight, ≥25×10⁴ cells/kg of body weight, ≥30×10⁴ cells/kg of body weight, ≥35×10⁴ cells/kg of body weight, ≥40×10⁴ cells/kg of body weight, ≥45×10⁴ cells/kg of body weight, ≥50×10⁴ cells/kg of body weight, ≥55×10⁴ cells/kg of body weight, ≥60×10⁴ cells/kg of body weight, ≥65×10⁴ cells/kg of body weight, ≥70×10⁴ cells/kg of body weight, ≥75×10⁴ cells/kg of body weight, ≥80×10⁴ cells/kg of body weight, ≥85×10⁴ cells/kg of body weight, 90×10⁴ cells/kg of body weight, ≥95×10⁴ cells/kg of body weight, ≥10×10⁵ cells/kg of body weight, ≥15×10⁵ cells/kg of body weight, ≥20×10⁵ cells/kg of body weight, ≥25×10⁵ cells/kg of body weight, ≥30×10⁵ cells/kg of body weight, ≥35×10⁵ cells/kg of body weight, ≥40×10⁵ cells/kg of body weight, ≥45×10⁵ cells/kg of body weight, ≥50×10⁵ cells/kg of body weight, ≥55×10⁵ cells/kg of body weight, ≥60×10⁵ cells/kg of body weight, ≥65×10⁵ cells/kg of body weight, ≥70×10⁵ cells/kg of body weight, ≥75×10⁵ cells/kg of body weight, ≥80×10⁵ cells/kg of body weight, ≥85×10⁵ cells/kg of body weight, 90×10⁵ cells/kg of body weight, ≥95×10⁵ cells/kg of body weight, ≥10×10⁶ cells/kg of body weight, ≥15×10⁶ cells/kg of body weight, ≥20×10⁶ cells/kg of body weight, ≥25×10⁶ cells/kg of body weight, ≥30×10⁶ cells/kg of body weight, ≥35×10⁶ cells/kg of body weight, ≥40×10⁶ cells/kg of body weight, ≥45×10⁶ cells/kg of body weight, ≥50×10⁶ cells/kg of body weight, ≥55×10⁶ cells/kg of body weight, ≥60×10⁶ cells/kg of body weight, ≥65×10⁶ cells/kg of body weight, ≥70×10⁶ cells/kg of body weight, ≥75×10⁶ cells/kg of body weight, ≥80×10⁶ cells/kg of body weight, ≥85×10⁶ cells/kg of body weight, 90×10⁶ cells/kg of body weight, ≥95×10⁶ cells/kg of body weight, ≥10×10⁷ cells/kg of body weight, ≥15×10⁷ cells/kg of body weight, ≥20×10⁷ cells/kg of body weight, ≥25×10⁷ cells/kg of body weight, ≥30×10⁷ cells/kg of body weight, ≥35×10⁷ cells/kg of body weight, ≥40×10⁷ cells/kg of body weight, ≥45×10⁷ cells/kg of body weight, ≥50×10⁷ cells/kg of body weight, ≥55×10⁷ cells/kg of body weight, ≥60×10⁷ cells/kg of body weight, ≥65×10⁷ cells/kg of body weight, ≥70×10⁷ cells/kg of body weight, ≥75×10⁷ cells/kg of body weight, ≥80×10⁷ cells/kg of body weight, ≥85×10⁷ cells/kg of body weight, 90×10⁷ cells/kg of body weight, ≥95×10⁷ cells/kg of body weight, ≥10×10⁸ cells/kg of body weight, ≥15×10⁸ cells/kg of body weight, ≥20×10⁸ cells/kg of body weight, ≥25×10⁸ cells/kg of body weight, ≥30×10⁸ cells/kg of body weight, ≥35×10⁸ cells/kg of body weight, ≥40×10⁸ cells/kg of body weight, ≥45×10⁸ cells/kg of body weight, ≥50×10⁸ cells/kg of body weight, ≥55×10⁸ cells/kg of body weight, ≥60×10⁸ cells/kg of body weight, ≥65×10⁸ cells/kg of body weight, ≥70×10⁸ cells/kg of body weight, ≥75×10⁸ cells/kg of body weight, ≥80×10⁸ cells/kg of body weight, ≥85×10⁸ cells/kg of body weight, 90×10⁸ cells/kg of body weight, ≥95×10⁸ cells/kg of body weight or ≥10×10⁹ cells/kg of body weight.

In some cases, the engineered hematopoietic cells may contain a combination of $CD34^+$ and $CD3^+$ cells for infusion into HLA-matched or HLA-mismatched recipients. In one case, at least 10×10⁶ $CD34^+$ cells/kg recipient weight and at least 1.0×10⁶ $CD3^+$ cells/kg are infused into the recipient. In another case, at least 10×10⁶ $CD34^+$ cells/kg recipient weight and at least 1.0×10⁷ $CD3^+$ cells/kg are infused into the recipient. In another case, at least 10×10⁶ $CD34^+$ cells/kg recipient weight and between 1.0-5.0×10⁶ $CD3^+$ cells/kg are infused into the recipient. In another case, less than 15×10⁶ $CD34^+$ cells/kg recipient weight and at least 50×10⁶ $CD3^+$ cells/kg are infused into the recipient.

Isolated and purified CD34+ cells and CD3+ cells may be freshly isolated or frozen (e.g., cryopreserved) prior to use in an engineered hematopoietic cell composition. In some cases, the CD34+ cells may be combined with the CD3+ cells prior to use as freshly isolated or frozen cells for preparing an engineered hematopoietic cell composition.

In some cases, the CD34+ and CD3+ cells are maintained independently either as freshly isolated cells or as cryopreserved cells. For example, CD34+ cells and CD3+ cells freshly maintained may be combined such that the target doses of CD34+ and CD3+ cells are achieved in the engineered composition for infusion. In other cases, CD34+ and CD3+ cells cryopreserved independently may be thawed and the target doses of each cell type determined after thawing. The thawed CD34+ and CD3+ cells may be combined such that the target doses of CD34+ and CD3+ cells are achieved in the engineered composition for infusion.

Processing Engineered Hematopoietic Cells for Pharmaceutical Compositions

Engineered hematopoietic cells (e.g., CD34+ and CD3+ cells) may be freshly prepared or previously frozen (e.g., cryopreserved) prior to generating a pharmaceutical composition for administration to a recipient. In some cases, the CD34+ and CD3+ cells may be HLA-matched between the donor and the recipient. In other cases, the CD34+ and CD3+ cells may be HLA-mismatched between the donor and the recipient.

Methods of cryopreservation are described elsewhere herein. In some cases, one aliquot of CD34+ cells is thawed. In other cases, more than one aliquot of CD34+ cells is thawed. For example, at least one aliquot, two aliquots, three aliquots, four aliquots, five aliquots, six aliquots, seven aliquots, eight aliquots, nine aliquots, 10 aliquots, 11 aliquots, 12 aliquots, 13 aliquots, 14 aliquots, 15 aliquots, 16 aliquots, 17 aliquots, 18 aliquots, 19 aliquots, 20 aliquots, 21 aliquots, 22 aliquots, 23 aliquots, 24 aliquots, 25 aliquots, 26 aliquots, 27 aliquots, 28 aliquots, 29 aliquots, 30 aliquots, 31 aliquots, 32 aliquots, 33 aliquots, 34 aliquots, 35 aliquots, 36 aliquots, 37 aliquots, 38 aliquots, 39 aliquots, 40 aliquots, 41 aliquots, 42 aliquots, 43 aliquots, 44 aliquots, 45 aliquots, 46 aliquots, 47 aliquots, 48 aliquots, 49 aliquots, 50 aliquots or more than 50 aliquots are thawed.

In some cases, one aliquot of CD3+ cells is thawed. In other cases, more than one aliquot of CD3+ cells is thawed. For example, at least one aliquot, two aliquots, three aliquots, four aliquots, five aliquots, six aliquots, seven aliquots, eight aliquots, nine aliquots, 10 aliquots, 11 aliquots, 12 aliquots, 13 aliquots, 14 aliquots, 15 aliquots, 16 aliquots, 17 aliquots, 18 aliquots, 19 aliquots, 20 aliquots, 21 aliquots, 22 aliquots, 23 aliquots, 24 aliquots, 25 aliquots, 26 aliquots, 27 aliquots, 28 aliquots, 29 aliquots, 30 aliquots, 31 aliquots, 32 aliquots, 33 aliquots, 34 aliquots, 35 aliquots, 36 aliquots, 37 aliquots, 38 aliquots, 39 aliquots, 40 aliquots, 41 aliquots, 42 aliquots, 43 aliquots, 44 aliquots, 45 aliquots, 46 aliquots, 47 aliquots, 48 aliquots, 49 aliquots, 50 aliquots or more than 50 aliquots are thawed.

In some cases, one aliquot of the combination of CD34+ cells and CD3+ cells is thawed. In other cases, more than one aliquot of the combination of CD34+ cells and CD3+ cells is thawed. For example, at least one aliquot, two aliquots, three aliquots, four aliquots, five aliquots, six aliquots, seven aliquots, eight aliquots, nine aliquots, 10 aliquots, 11 aliquots, 12 aliquots, 13 aliquots, 14 aliquots, 15 aliquots, 16 aliquots, 17 aliquots, 18 aliquots, 19 aliquots, 20 aliquots, 21 aliquots, 22 aliquots, 23 aliquots, 24 aliquots, 25 aliquots, 26 aliquots, 27 aliquots, 28 aliquots, 29 aliquots, 30 aliquots, 31 aliquots, 32 aliquots, 33 aliquots, 34 aliquots, 35 aliquots, 36 aliquots, 37 aliquots, 38 aliquots, 39 aliquots, 40 aliquots, 41 aliquots, 42 aliquots, 43 aliquots, 44 aliquots, 45 aliquots, 46 aliquots, 47 aliquots, 48 aliquots, 49 aliquots, 50 aliquots or more than 50 aliquots are thawed.

In some cases, freshly prepared engineered hematopoietic cells may be expanded ex vivo using methods known to those of skill in the art. In other cases, previously frozen engineered hematopoietic cells may be expanded ex vivo using methods known to those of skill in the art. In some cases, either freshly prepared or previously frozen engineered hematopoietic cells may be expanded ex vivo by use of at least one growth factor. In some cases, more than one growth factor may be used to expand the cells. For example, a growth factor may be activin A, ADAM-10, Angiogenin, Angiopoietin-1, Angiopoietin-2, Angiopoietin-3, Angiopoietin-4, BIO, Bone Morphogenetic Protien-2, Bone Morphogenetic Protien-3, Bone Morphogenetic Protien-4, Bone Morphogenetic Protien-5, Bone Morphogenetic Protien-6, Bone Morphogenetic Protien-7, Brain-derived neurotrophic factor, E-cadherin, Fc chimera, cathepsin G, ch2 inhibitor II, epidermal growth factor, eotaxin, eotaxin-2, eotaxin-3, Fas, fibroblast growth factor-4, fibroblast growth factor-5, fibroblast growth factor-6, fibroblast growth factor-8b, fibroblast growth factor-8c, fibroblast growth factor-9, fibroblast growth factor-10, fibroblast growth factor-17, fibroblast growth factor-18, fibroblast growth factor, fibroblast growth factor acidic, fibroblast growth factor basic, fibroblast growth factor basic fragment 1-24 bovine, fibroblast growth factor receptor 1a, fibroblast growth factor receptor 1b, fibroblast growth factor receptor 2a, fibroblast growth factor receptor 2b fibroblast growth factor receptor 3a, fibroblast growth factor receptor 4, flt-3, flk-2 ligand, granulocyte colony stimulating factor, granulocyte-macrophage colony stimulating factor, GROa, GROb, heparin-binding EGF-like growth factor, heregulin-a1 EGF domain, heregulin-b1 EGF domain, heregulin B, insulin-like growth factor-1, insulin-like growth factor-II fragment 33-40, insulin-like growth factor binding protein-2, insulin-like growth factor-1, insulin-like growth factor II, interferon a, interferon aA, interferon aA/D, interferon b, interferon g, interferon, interferon g receptor 1, interleukin-1a, interleukin-1b, interleukin soluble receptor type II, interleukin-2, interleukin-2 soluble receptor a, interleukin-2 soluble receptor b, interleukin-2 soluble receptor g, interleukin-3, interleukin-5, interleukin-6, interleukin-6 soluble receptor, interleukin-7, interleukin-8, interleukin-11, interleukin-12, leukemia inhibitory factor, LONG EGF, LONG R2 IGF-1, LYN A, macrophage inflammatory protein-1a, macrophage inflammatory protein-1b, macrophage inflammatory protein-lg, matrix metalloproteinase-1, matrix metalloproteinase-2, matrix metalloproteinase-9, MIG, monocyte chemotactic protein-1, monocyte chemotactic protein-3, monocyte chemotactic protein-4, monocyte chemotactic protein-5, nerve growth factor receptor, neurotrophin-3, neurotrophin-4, noggin, notch-1, oncostatin M, oncostatin M receptor b, osteopontin, osteoprotegrin, phenylarsine oxide, platelet-derived growth factor, platelet-derived growth factor-AB, platelet-derived growth factor-BB, platelet-derived growth factor soluble receptor a, platelet derived growth factor receptor b, anti-POU5F1, oct4, RANTES, SCF soluble receptor, L-selectin, stem cell factor, stromal cell-derived factor 1a, stromal cell-derived factor 1b, thromopoietin, Tie-1, tissue inhibitor of metalloproteinase-2, transforming growth factor-a, transforming growth factor-b1, transforming growth factor-b2, transforming growth factor-b3, transforming growth factor-b1 receptor II soluble fragment, transforming growth factor-b soluble receptor III, TrkB, vascular endothelial growth factor 120, vascular endothelial growth factor 121, vascular endothelial growth factor 164, VEGF receptor-2/Flk1/KDR and/or VEGF Receptor-3/Flt-4. The amount of each growth factor used for ex vivo expansion is known to one of skill in the art and suitable for use with the methods described herein.

In some cases, either freshly prepared or previously frozen engineered hematopoietic cells may be expanded ex vivo by use of at least one type of feeder cell. Any type of feeder cell may be used such that the feeder cells maintain viability of engineered hematopoietic cells, and promote engineered hematopoietic cell proliferation and differentiation. In some cases, at least one growth factor combined with at least one feeder cell may be used such that the feeder cells maintain viability of engineered hematopoietic cells, and promote engineered hematopoietic cell proliferation and differentiation. In some cases, feeder cells may be mitotically inactive. In some cases, more than one type of feeder cell may be used to expand the cells. In some cases, a type of feeder cell may be derived from adult mouse endothelial cells, embryonic mouse endothelial cells, adult mouse fibroblasts, embryonic mouse fibroblasts, adult human endothelial cells, embryonic human endothelial cells, adult human fibroblasts, embryonic human fibroblasts, adult non-human primate endothelial cells, embryonic non-human primate endothelial cells, adult non-human primate fibroblasts, embryonic non-human primate fibroblasts, adult bovine endothelial cells, embryonic bovine endothelial cells, adult bovine fibroblasts, embryonic bovine fibroblasts, adult porcine endothelial cells, embryonic porcine endothelial cells, adult porcine fibroblasts, embryonic porcine fibroblasts and the like.

In some cases, feeder cells may be modified. For example, the modifications may be genetic. In some cases, feeder cells may express non-native genes, repress expression of native genes or overexpress native genes. For example, feeder cells may express LacZ, GFP, RFP or the like.

Compositions of Hematopoietic Stem Cells

The hematopoietic stem cells and compositions thereof of the methods provided herein can be supplied in the form of a pharmaceutical composition, comprising an isotonic excipient prepared under sufficiently sterile conditions for human administration. Choice of the cellular excipient and any accompanying elements of the composition is adapted in accordance with the route and device used for administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

In some cases, the hematopoietic stem cells may be HLA-matched between the donor and the recipient. In other cases, the hematopoietic stem cells may be HLA-mismatched between the donor and the recipient.

In some cases, the pharmaceutical composition may contain agents which enhance engraftment of the hematopoietic cells in the recipient. In other cases, the pharmaceutical composition may contain agents which do not affect engraftment of the hematopoietic cells in the recipient. In some cases, the pharmaceutical composition may contain agents which prevent a negative reaction of the recipient to the hematopoietic cells. For example, any agent as mentioned above may be a cytokine, a chemokine, a growth factor, an excipient, a carrier, an inert molecule, an antibody or a fragment thereof, a small molecule, a drug, an agonist, an antagonist, a chemical or the like. Any agent used in a pharmaceutical composition of hematopoietic cells in the recipient is physiologically acceptable.

A variety of methods may be used to deliver hematopoietic cells to the recipient and any method known to one of skill in the art may be applied to the hematopoietic cells described herein. For example, the hematopoietic cells may be delivered to the recipient by injection using a needle, catheter, central line or the like. In some cases, the hematopoietic cells may be delivered intravascularly, intravenously, intraarterially, intracranially, intraperitoneally, subcutaneously, intramuscularly, intraorbitally, or through any source which permits the hematopoietic cells to home to an appropriate site in the recipient such that the hematopoietic cells persist, regenerate and differentiate in the recipient.

The composition of engineered hematopoietic cells may also comprise or be accompanied with one or more other ingredients that facilitate the engraftment or functional mobilization of the cells. For example, ingredients may include matrix proteins that support the cells, promote adhesion of the cells, or complementary cell types (e.g., endothelial cells).

In some cases, the hematopoietic cells may home to an organ, a tissue or a cell type within the recipient. For example, an organ may the brain, thyroid, eyes, skin, lungs, pancreas, spleen, bladder, prostate, kidneys, stomach, liver, heart, adrenal glands, bronchi, large intestine, small intestine, spinal cord, bone, bone marrow, pituitary gland, salivary gland, gall bladder, larynx, lymph nodes, prostate, skeletal muscles, appendix, esophagus, parathyroid glands, trachea, urethra, ovaries, testicles, uterus, ureters, fallopian tubes, or any gland in the body. In some cases, a tissue or a cell type may be part of an organ. In some cases, a tissue or a cell type may be a derived from an organ. In some cases, a tissue or a cell type may be isolated from an organ.

In some cases, the recipient of the hematopoietic stem cells may not have received a solid organ transplant. In other cases, the recipient may have received a solid organ transplant. In some cases, the solid organ transplant may be performed at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days, 20 days, 20.5 days, 21 days, 21.5 days, 22 days, 22.5 days, 23 days, 23.5 days, 24 days, 24.5 days, 25 days, 25.5 days, 26 days, 26.5 days, 27 days, 27.5 days, 28 days, 28.5 days, 29 days, 30 days, 30.5 days, 31 days, 31.5 days, 32 days, 32.5 days, 33 days, 33.5 days, 34 days, 34.5 days, 35 days, 35.5 days, 36 days, 36.5 days, 37 days, 37.5 days, 38 days, 38.5 days, 39 days, 40 days, 40.5 days, 41 days, 41.5 days, 42 days, 42.5 days, 43 days, 43.5 days, 44 days, 44.5 days, 45 days, 45.5 days, 46 days, 46.5 days, 47 days, 47.5 days, 48 days, 48.5 days, 49 days or at least 50 days prior to administration of the engineered hematopoietic stem cells to the recipient.

In some cases, the solid organ transplant recipient may be administered one dose of engineered hematopoietic stem cells. In other cases, the solid organ transplant recipient may be administered more than one dose of engineered hematopoietic stem cells. In some cases, the time elapsed between each dose of engineered hematopoietic stem cells may be the same. In other cases, the time elapsed between each dose of engineered hematopoietic stem cells may be different.

For example, the solid organ transplant recipient may be administered a first dose of engineered hematopoietic stem cells at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days, 20 days, 20.5 days, 21 days, 21.5 days, 22 days, 22.5 days, 23 days, 23.5 days, 24 days, 24.5 days, 25 days, 25.5 days, 26 days, 26.5 days, 27 days, 27.5 days, 28 days, 28.5 days, 29 days, 30 days, 30.5 days, 31 days, 31.5 days, 32 days, 32.5 days, 33 days, 33.5 days, 34 days, 34.5 days, 35 days, 35.5 days, 36 days, 36.5 days, 37 days, 37.5 days, 38 days, 38.5 days, 39 days, 40 days, 40.5 days, 41 days, 41.5 days, 42 days, 42.5 days, 43 days, 43.5 days, 44 days, 44.5 days, 45 days, 45.5 days, 46 days, 46.5 days, 47 days, 47.5 days, 48 days, 48.5 days, 49 days or at least 50 days following solid organ transplantation.

In some cases, a second dose of engineered hematopoietic stem cells may be administered to the recipient at least In some cases, the solid organ transplant may be performed at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days, 20 days, 20.5 days, 21 days, 21.5 days, 22 days, 22.5 days, 23 days, 23.5 days, 24 days, 24.5 days, 25 days, 25.5 days, 26 days, 26.5 days, 27 days, 27.5 days, 28 days, 28.5 days, 29 days, 30 days, 30.5 days, 31 days, 31.5 days, 32 days, 32.5 days, 33 days, 33.5 days, 34 days, 34.5 days, 35 days, 35.5 days, 36 days, 36.5 days, 37 days, 37.5 days, 38 days, 38.5 days, 39 days, 40 days, 40.5 days, 41 days, 41.5 days, 42 days, 42.5 days, 43 days, 43.5 days, 44 days, 44.5 days, 45 days, 45.5 days, 46 days, 46.5 days, 47 days, 47.5 days, 48 days, 48.5 days, 49 days or at least 50 days after the first dose of engineered hematopoietic stem cells such that administration of engineered hematopoietic stem cells is recursive.

In some cases, more than two doses of engineered hematopoietic stem cells may be administered to the solid organ transplant recipient. For example, at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days, 20 days, 20.5 days, 21 days, 21.5 days, 22 days, 22.5 days, 23 days, 23.5 days, 24 days, 24.5 days, 25 days, 25.5 days, 26 days, 26.5 days, 27 days, 27.5 days, 28 days, 28.5 days, 29 days, 30 days, 30.5 days, 31 days, 31.5 days, 32 days, 32.5 days, 33 days, 33.5 days, 34 days, 34.5 days, 35 days, 35.5 days, 36 days, 36.5 days, 37 days, 37.5 days, 38 days, 38.5 days, 39 days, 40 days, 40.5 days, 41 days, 41.5 days, 42 days, 42.5 days, 43 days, 43.5 days, 44 days, 44.5 days, 45 days, 45.5 days, 46 days, 46.5 days, 47 days, 47.5 days, 48 days, 48.5 days, 49 days or at least 50 days may pass between administration of the second and the third doses of engineered hematopoietic stem cells such that administration of engineered hematopoietic stem cells is recursive.

Any of the above mentioned time frames may also pass between the third and fourth doses, the fourth and fifth doses, the fifth and sixth doses, the sixth and seventh doses, the seventh and eighth doses, the eighth and ninth doses, the ninth and tenth doses and so on.

Non-Myeloablative Conditioning

Following transplantation of the HLA-matched or HLA-mismatched solid organ, the recipient may be treated with non-myeloablative conditioning. In some cases, non-myeloablative conditioning may be performed using methods known to those of skill in the art. In other cases, recipients may receive non-myeloablative conditioning that includes a plurality of agents. In some cases, the agents may include thymoglobulin (ATG), a T cell depleting agent and/or radiation.

In some cases, ATG may be delivered intravenously. In some cases, a single dose of ATG may be delivered to the recipient. In other cases, the recipient may receive more than one dose of ATG. For example, a recipient may receive at least one dose of ATG, two doses of ATG, three doses of ATG, four doses of ATG, five doses of ATG, six doses of ATG, seven doses of ATG, eight doses of ATG, nine doses of ATG, 10 doses of ATG, 11 doses of ATG, 12 doses of ATG, 13 doses of ATG, 14 doses of ATG, 15 doses of ATG, 16 doses of ATG, 17 doses of ATG, 18 doses of ATG, 19 doses of ATG, or at least 20 doses of ATG.

In some cases, each dose of ATG may be at least 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 15.5 mg/kg, 16 mg/kg, 16.5 mg/kg, 17 mg/kg, 17.5 mg/kg, 18 mg/kg, 18.5 mg/kg, 19 mg/kg or at least 20 mg/kg.

ATG may be administered on the same day of solid-organ transplantation. In some cases, the plurality of ATG doses may be administered over a period of time after organ transplantation. In some cases, the plurality of ATG doses may be administered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

In some cases, the ATG is delivered intra-operatively before the transplanted organ is perfused with host blood. In other cases, the ATG is delivered intra-operatively after the transplanted organ is perfused with host blood. In some cases, the ATG is delivered intra-venously before the transplanted organ is perfused with host blood. In other cases, the ATG is delivered intra-venously after the transplanted organ is perfused with host blood. In some cases, the ATG is delivered intra-arterially before the transplanted organ is perfused with host blood. In other cases, the ATG is delivered intra-arterially after the transplanted organ is perfused with host blood. In some cases, the ATG is delivered subcutaneously before the transplanted organ is perfused with host blood. In other cases, the ATG is delivered subcutaneously after the transplanted organ is perfused with host blood. In some cases, the ATG is delivered intraperitoneally before the transplanted organ is perfused with host blood. In other cases, the ATG is delivered intraperitonially after the transplanted organ is perfused with host blood.

Corticosteroid therapy may be given as medication prior to administration of ATG. In some cases, solumedrol may be administered although any corticosteroid known to one of skill in the art sufficient to reduce side effects of ATG may be used at an effective dose. In some cases, the corticosteroid may be administered on the same day as ATG is administered. For example, solumedrol may be administered at a dose within the range of 0-40 mg, 5-50 mg, 10-60 mg, 15-65 mg, 20-70 mg, 25-75 mg, 30-80 mg, 35-85 mg, 40-90 mg, 45-95 mg, 50-100 mg, 55-105 mg, 60-110 mg, 65-115 mg, 70-120 mg, 75-125 mg, 80-130 mg, 85-135 mg, 90-140 mg, 95-145 mg, 100-150 mg, 105-155 mg, 110-160 mg, 115-165 mg, 120-170 mg, 125-175 mg, 130-180 mg, 135-185 mg, 140-190 mg, 145-195 mg or 150-200 mg.

Following the final dose of ATG administered to the recipient, prednisone may be administered. In some cases, a single dose of prednisone may be administered. In other cases, more than one dose of prednisone may be administered. For example, multiple doses of prednisone may be administered according to a tapering course or a constant course.

In some cases, for a tapering course, the first dose of prednisone may start at 100 mg/d and then the dose reduced by 5 mg/d until constant at 5 mg/d for at least 15 days, the first dose of prednisone may start at 90 mg/d and reduced by 5 mg/d until constant for at least 15 days, the first dose of prednisone may start at 80 mg/d and reduced by 5 mg/d until constant for at least 15 days, the first dose of prednisone may start at 70 mg/d and reduced by 5 mg/d until constant for at least 15 days, the first dose of prednisone may start at 60 mg/d and reduced by 5 mg/d until constant for at least 15 days, the first dose of prednisone may start at 50 mg/d and reduced by 5 mg/d until constant for at least 15 days, the first dose of prednisone may start at 40 mg/d and reduced by 5 mg/d until constant for at least 15 days, the first dose of prednisone may start at 30 mg/d and reduced by 5 mg/d until constant for at least 15 days, the first dose of prednisone may start at 20 mg/d and reduced by 5 mg/d until constant for at least 15 days or the first dose of prednisone may start at 10 mg/d and reduced by 5 mg/d until constant for at least 15 days. In some cases, for a constant course, the doses of prednisone may be 100 mg/d, 90 mg/d, 80 mg/d, 70 mg/d, 60 mg/d, 50 mg/d, 40 mg/d, 30 mg/d, 20 mg/d, 10 mg/d or 5 mg/d for at least 15 days.

In some cases, for a tapering course, the first dose of prednisone may start at 100 mg/d and reduced by 5 mg/d until constant for at least 30 days, the first dose of prednisone may start at 90 mg/d and reduced by 5 mg/d until constant for at least 30 days, the first dose of prednisone may start at 80 mg/d and reduced by 5 mg/d until constant for at least 30 days, the first dose of prednisone may start at 70 mg/d and reduced by 5 mg/d until constant for at least 30 days, the first dose of prednisone may start at 60 mg/d and reduced by 5 mg/d until constant for at least 30 days, the first dose of prednisone may start at 50 mg/d and reduced by 5 mg/d until constant for at least 30 days, the first dose of prednisone may start at 40 mg/d and reduced by 5 mg/d until constant for at least 30 days, the first dose of prednisone may start at 30 mg/d and reduced by 5 mg/d until constant for at least 30 days, the first dose of prednisone may start at 20 mg/d and reduced by 5 mg/d until constant for at least 30 days or the first dose of prednisone may start at 10 mg/d and reduced by 5 mg/d until constant for at least 30 days. In some cases, for a constant course, the doses of prednisone may be 100 mg/d, 90 mg/d, 80 mg/d, 70 mg/d, 60 mg/d, 50 mg/d, 40 mg/d, 30 mg/d, 20 mg/d, 10 mg/d or 5 mg/d for at least 30 days.

In some cases, for a tapering course, the first dose of prednisone may start at 100 mg/d and reduced by 5 mg/d until constant for at least 45 days, the first dose of prednisone may start at 90 mg/d and reduced by 5 mg/d until constant for at least 45 days, the first dose of prednisone may start at 80 mg/d and reduced by 5 mg/d until constant for at least 45 days, the first dose of prednisone may start at 70 mg/d and reduced by 5 mg/d until constant for at least 45 days, the first dose of prednisone may start at 60 mg/d and reduced by 5 mg/d until constant for at least 45 days, the first dose of prednisone may start at 50 mg/d and reduced by 5 mg/d until constant for at least 45 days, the first dose of prednisone may start at 40 mg/d and reduced by 5 mg/d until constant for at least 45 days, the first dose of prednisone may start at 30 mg/d and reduced by 5 mg/d until constant for at least 45 days, the first dose of prednisone may start at 20 mg/d and reduced by 5 mg/d until constant for at least 45 days or the first dose of prednisone may start at 10 mg/d and reduced by 5 mg/d until constant for at least 45 days. In some cases, for a constant course, the doses of prednisone may be 100 mg/d, 90 mg/d, 80 mg/d, 70 mg/d, 60 mg/d, 50 mg/d, 40 mg/d, 30 mg/d, 20 mg/d, 10 mg/d or 5 mg/d for at least 45 days.

In some cases, for a tapering course, the first dose of prednisone may start at 100 mg/d and reduced by 5 mg/d until constant for at least 60 days, the first dose of prednisone may start at 90 mg/d and reduced by 5 mg/d until constant for at least 60 days, the first dose of prednisone may start at 80 mg/d and reduced by 5 mg/d until constant for at least 60 days, the first dose of prednisone may start at 70 mg/d and reduced by 5 mg/d until constant for at least 60 days, the first dose of prednisone may start at 60 mg/d and reduced by 5 mg/d until constant for at least 60 days, the first dose of prednisone may start at 50 mg/d and reduced by 5 mg/d until constant for at least 60 days, the first dose of prednisone may start at 40 mg/d and reduced by 5 mg/d until constant for at least 60 days, the first dose of prednisone may start at 30 mg/d and reduced by 5 mg/d until constant for at least 60 days, the first dose of prednisone may start at 20 mg/d and reduced by 5 mg/d until constant for at least 60 days or the first dose of prednisone may start at 10 mg/d and reduced by 5 mg/d until constant for at least 60 days. In some cases, for a constant course, the doses of prednisone may be 100 mg/d, 90 mg/d, 80 mg/d, 70 mg/d, 60 mg/d, 50 mg/d, 40 mg/d, 30 mg/d, 20 mg/d, 10 mg/d or 5 mg/d for at least 60 days.

The corticosteroid and/or prednisone may be administered intravascularly, intravenously, intraarterially, intracranially, intraperitoneally, subcutaneously, intramuscularly, intraorbitally, orally, topically, or through any source which permits proper metabolism of the corticosteroid and/or prednisone by the recipient.

In some cases, any T cell depleting agent known to one of skill in the art can be used as a portion of a non-myeloablative conditioning regime for the recipient. In some cases, the T cell depleting agent may be an anti-T cell monoclonal antibody or a T cell depleting drug (e.g., fludarabine). In some cases, a single T cell depleting agent is administered to the recipient. In other cases, more than one T cell depleting agent is administered to the recipient.

In some cases, a T cell depleting agent may be delivered intravenously. In some cases, a single dose of a T cell depleting agent may be delivered to the recipient. In other cases, the recipient may receive more than one dose of a T cell depleting agent. For example, a recipient may receive at least one dose of a T cell depleting agent, two doses of a T cell depleting agent, three doses of a T cell depleting agent, four doses of a T cell depleting agent, five doses of a T cell depleting agent, six doses of a T cell depleting agent, seven doses of a T cell depleting agent, eight doses of a T cell depleting agent, nine doses of a T cell depleting agent, 10 doses of a T cell depleting agent, 11 doses of a T cell depleting agent, 12 doses of a T cell depleting agent, 13 doses of a T cell depleting agent, 14 doses of a T cell depleting agent, 15 doses of a T cell depleting agent, 16 doses of a T cell depleting agent, 17 doses of a T cell depleting agent, 18 doses of a T cell depleting agent, 19 doses of a T cell depleting agent, or 20 doses of a T cell depleting agent.

A T cell depleting agent may be administered on the same day of solid-organ transplantation. In some cases, the plurality of T cell depleting agent doses may be delivered over a period of time after organ transplantation. In some cases, the plurality of T cell depleting agent doses may be delivered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

In some cases, the T cell depleting agent is delivered intra-operatively before the transplanted organ is perfused with host blood. In other cases, the T cell depleting agent is delivered intra-operatively after the transplanted organ is perfused with host blood. In some cases, the T cell depleting agent is delivered intravenously before the transplanted organ is perfused with host blood. In other cases, the T cell depleting agent is delivered intravenously after the transplanted organ is perfused with host blood. In some cases, the T cell depleting agent is delivered intra-arterially before the transplanted organ is perfused with host blood. In other cases, the T cell depleting agent is delivered intra-arterially after the transplanted organ is perfused with host blood. In some cases, the T cell depleting agent is delivered subcutaneously before the transplanted organ is perfused with host blood. In other cases, the T cell depleting agent is delivered subcutaneously after the transplanted organ is perfused with host blood. In some cases, the T cell depleting agent is delivered intraperitoneally before the transplanted organ is perfused with host blood. In other cases, the T cell depleting agent is delivered intraperitoneally after the transplanted organ is perfused with host blood.

In some cases, fludarabine may be delivered intravenously. In some cases, a single dose of fludarabine may be delivered to the recipient. In other cases, the recipient may receive more than one dose of fludarabine. For example, a recipient may receive at least one dose of fludarabine, two doses of fludarabine, three doses of fludarabine, four doses of fludarabine, five doses of fludarabine, six doses of fludarabine, seven doses of fludarabine, eight doses of fludarabine, nine doses of fludarabine, 10 doses of fludarabine, 11 doses of fludarabine, 12 doses of fludarabine, 13 doses of fludarabine, 14 doses of fludarabine, 15 doses of fludarabine, 16 doses of fludarabine, 17 doses of fludarabine, 18 doses of fludarabine, 19 doses of fludarabine, or at least 20 doses of fludarabine.

In some cases, each dose of fludarabine may be at least 0.1 mg/m2/d, 0.2 mg/m2/d, 0.3 mg/m2/d, 0.4 mg/m2/d, 0.5 mg/m2/d, 0.6 mg/m2/d, 0.7 mg/m2/d, 0.8 mg/m2/d, 0.9 mg/m2/d, 1.0 mg/m2/d, 1.1 mg/m2/d, 1.2 mg/m2/d, 1.3 mg/m2/d, 1.4 mg/m2/d, 1.5 mg/m2/d, 1.6 mg/m2/d, 1.7 mg/m2/d, 1.8 mg/m2/d, 1.9 mg/m2/d, 2.0 mg/m2/d, 2.1 mg/m2/d, 2.2 mg/m2/d, 2.3 mg/m2/d, 2.4 mg/m2/d, 2.5 mg/m2/d, 2.6 mg/m2/d, 2.7 mg/m2/d, 2.8 mg/m2/d, 2.9 mg/m2/d, 3.0 mg/m2/d, 3.1 mg/m2/d, 3.2 mg/m2/d, 3.3 mg/m2/d, 3.4 mg/m2/d, 3.5 mg/m2/d, 3.6 mg/m2/d, 3.7 mg/m2/d, 3.8 mg/m2/d, 3.9 mg/m2/d, 4.0 mg/m2/d, 4.1 mg/m2/d, 4.2 mg/m2/d, 4.3 mg/m2/d, 4.4 mg/m2/d, 4.5 mg/m2/d, 4.6 mg/m2/d, 4.7 mg/m2/d, 4.8 mg/m2/d, 4.9 mg/m2/d, 5.0 mg/m2/d, 5.1 mg/m2/d, 5.2 mg/m2/d, 5.3 mg/m2/d, 5.4 mg/m2/d, 5.5 mg/m2/d, 5.6 mg/m2/d, 5.7 mg/m2/d, 5.8 mg/m2/d, 5.9 mg/m2/d, 6.0 mg/m2/d, 6.1 mg/m2/d, 6.2 mg/m2/d, 6.3 mg/m2/d, 6.4 mg/m2/d, 6.5 mg/m2/d, 6.6 mg/m2/d, 6.7 mg/m2/d, 6.8 mg/m2/d, 6.9 mg/m2/d, 7.0 mg/m2/d, 7.1 mg/m2/d, 7.2 mg/m2/d, 7.3 mg/m2/d, 7.4 mg/m2/d, 7.5 mg/m2/d, 7.6 mg/m2/d, 7.7 mg/m2/d, 7.8 mg/m2/d, 7.9 mg/m2/d, 8.0 mg/m2/d, 8.1 mg/m2/d, 8.2 mg/m2/d, 8.3 mg/m2/d, 8.4 mg/m2/d, 8.5 mg/m2/d, 8.6 mg/m2/d, 8.7 mg/m2/d, 8.8 mg/m2/d, 8.9 mg/m2/d, 9.0 mg/m2/d, 9.1 mg/m2/d, 9.2 mg/m2/d, 9.3 mg/m2/d, 9.4 mg/m2/d, 9.5 mg/m2/d, 9.6 mg/m2/d, 9.7 mg/m2/d, 9.8 mg/m2/d, 9.9 mg/m2/d, 10 mg/m2/d, 10.5 mg/m2/d, 11 mg/m2/d, 11.5 mg/m2/d, 12 mg/m2/d, 12.5 mg/m2/d, 13 mg/m2/d, 13.5 mg/m2/d, 14 mg/m2/d, 14.5 mg/m2/d, 15 mg/m2/d, 15.5 mg/m2/d, 16 mg/m2/d, 16.5 mg/m2/d, 17 mg/m2/d, 17.5 mg/m2/d, 18 mg/m2/d, 18.5 mg/m2/d, 19 mg/m2/d, 20 mg/m2/d, 20.5 mg/m2/d, 21 mg/m2/d, 21.5 mg/m2/d, 22 mg/m2/d, 22.5 mg/m2/d, 23 mg/m2/d, 23.5 mg/m2/d, 24 mg/m2/d, 24.5 mg/m2/d, 25 mg/m2/d, 25.5 mg/m2/d, 26 mg/m2/d, 26.5 mg/m2/d, 27 mg/m2/d, 27.5 mg/m2/d, 28 mg/m2/d, 28.5 mg/m2/d, 29 mg/m2/d, 30 mg/m2/d, 30.5 mg/m2/d, 31 mg/m2/d, 31.5 mg/m2/d, 32 mg/m2/d, 32.5 mg/m2/d, 33 mg/m2/d, 33.5 mg/m2/d, 34 mg/m2/d, 34.5 mg/m2/d, 35 mg/m2/d, 35.5 mg/m2/d, 36 mg/m2/d, 36.5 mg/m2/d, 37 mg/m2/d, 37.5 mg/m2/d, 38 mg/m2/d, 38.5 mg/m2/d, 39 mg/m2/d, 40 mg/m2/d, 40.5 mg/m2/d, 41 mg/m2/d, 41.5 mg/m2/d, 42 mg/m2/d, 42.5 mg/m2/d, 43 mg/m2/d, 43.5 mg/m2/d, 44 mg/m2/d, 44.5 mg/m2/d, 45 mg/m2/d, 45.5 mg/m2/d, 46 mg/m2/d, 46.5 mg/m2/d, 47 mg/m2/d, 47.5 mg/m2/d, 48 mg/m2/d, 48.5 mg/m2/d, 49 mg/m2/d, 50 mg/m2/d, 50.5 mg/m2/d, 51 mg/m2/d, 51.5 mg/m2/d, 52 mg/m2/d, 52.5 mg/m2/d, 53 mg/m2/d, 53.5 mg/m2/d, 54 mg/m2/d, 54.5 mg/m2/d, 55 mg/m2/d, 55.5 mg/m2/d, 56 mg/m2/d, 56.5 mg/m2/d, 57 mg/m2/d, 57.5 mg/m2/d, 58 mg/m2/d, 58.5 mg/m2/d, 59 mg/m2/d or at least 60 mg/m2/d.

Fludarabine may be administered on the same day of solid-organ transplantation. In some cases, the plurality of fludarabine doses may be delivered over a period of time after organ transplantation. In some cases, the plurality of fludarabine doses may be delivered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

In some cases, the fludarabine is delivered intra-operatively before the transplanted organ is perfused with host blood. In other cases, the fludarabine is delivered intraoperatively after the transplanted organ is perfused with host blood. In some cases, the fludarabine is delivered intravenously before the transplanted organ is perfused with host blood. In other cases, the fludarabine is delivered intravenously after the transplanted organ is perfused with host blood. In some cases, the fludarabine is delivered intra-arterially before the transplanted organ is perfused with host blood. In other cases, the fludarabine is delivered intra-arterially after the transplanted organ is perfused with host blood. In some cases, the fludarabine is delivered subcutaneously before the transplanted organ is perfused with host blood. In other cases, the fludarabine is delivered subcutaneously after the transplanted organ is perfused with host blood. In some cases, the fludarabine is delivered intraperitoneally before the transplanted organ is perfused with host blood. In other cases, the fludarabine is delivered intraperitoneally after the transplanted organ is perfused with host blood.

In some cases, recipients are treated with irradiation. The irradiation may be fractionated or unfractionated. In the case that a recipient is treated with more than one dose of irradiation, all doses may be fractionated. In another case that a recipient is treated with more than one dose of irradiation, all doses may be unfractionated. In another case that a recipient is treated with more than one dose of irradiation, the doses may be a mix of fractionated unfractionated.

In some cases, the irradiation is delivered intraoperatively. In some cases, the irradiation is delivered intravenously. In some cases, the irradiation is delivered intraarterially. In some cases, the irradiation is delivered subcutaneously. In some cases, the irradiation is delivered intraperitoneally.

In some cases, a single dose of irradiation may be delivered to the recipient. In other cases, the recipient may receive more than one dose of irradiation. For example, a recipient may receive at least one dose of irradiation, two doses of irradiation, three doses of irradiation, four doses of irradiation, five doses of irradiation, six doses of irradiation, seven doses of irradiation, eight doses of irradiation, nine doses of irradiation, 10 doses of irradiation, 11 doses of irradiation, 12 doses of irradiation, 13 doses of irradiation, 14 doses of irradiation, 15 doses of irradiation, 16 doses of irradiation, 17 doses of irradiation, 18 doses of irradiation, 19 doses of irradiation, or at least 20 doses of irradiation.

In some cases, each dose of irradiation may be at least 1 cGy, 2 cGy, 3 cGy, 4 cGy, 5 cGy, 6 cGy, 7 cGy, 8 cGy, 9 cGy, 10 cGy, 11 cGy, 12 cGy, 13 cGy, 14 cGy, 15 cGy, 16 cGy, 17 cGy, 18 cGy, 19 cGy, 20 cGy, 21 cGy, 22 cGy, 23 cGy, 24 cGy, 25 cGy, 26 cGy, 27 cGy, 28 cGy, 29 cGy, 30 cGy, 31 cGy, 32 cGy, 33 cGy, 34 cGy, 35 cGy, 36 cGy, 37 cGy, 38 cGy, 39 cGy, 40 cGy, 41 cGy, 42 cGy, 43 cGy, 44 cGy, 45 cGy, 46 cGy, 47 cGy, 48 cGy, 49 cGy, 50 cGy, 51 cGy, 52 cGy, 53 cGy, 54 cGy, 55 cGy, 56 cGy, 57 cGy, 58 cGy, 59 cGy, 60 cGy, 61 cGy, 62 cGy, 63 cGy, 64 cGy, 65 cGy, 66 cGy, 67 cGy, 68 cGy, 69 cGy, 70 cGy, 71 cGy, 72 cGy, 73 cGy, 74 cGy, 75 cGy, 76 cGy, 77 cGy, 78 cGy, 79 cGy, 80 cGy, 81 cGy, 82 cGy, 83 cGy, 84 cGy, 85 cGy, 86 cGy, 87 cGy, 88 cGy, 89 cGy, 90 cGy, 91 cGy, 92 cGy, 93 cGy, 94 cGy, 95 cGy, 96 cGy, 97 cGy, 98 cGy, 99 cGy, 100 cGy, 105 cGy, 110 cGy, 115 cGy, 120 cGy, 125 cGy, 130 cGy, 135 cGy, 140 cGy, 145 cGy, 150 cGy, 155 cGy, 160 cGy, 165 cGy, 170 cGy, 175 cGy, 180 cGy, 185 cGy, 190 cGy, 195 cGy, 200 cGy, 205 cGy, 210 cGy, 215 cGy, 220 cGy, 225 cGy, 230 cGy, 235 cGy, 240 cGy, 245 cGy, 250 cGy, 255 cGy, 260 cGy, 265 cGy, 270 cGy, 275 cGy, 280 cGy, 285 cGy, 290 cGy, 295 cGy, 300 cGy, 305 cGy, 310 cGy, 315 cGy, 320 cGy, 325 cGy, 330 cGy, 335 cGy, 340 cGy, 345 cGy, 350 cGy, 355 cGy, 360 cGy, 365 cGy, 370 cGy, 375 cGy, 380 cGy, 385 cGy, 390 cGy, 395 cGy, 400 cGy, 405 cGy, 410 cGy, 415 cGy, 420 cGy, 425 cGy, 430 cGy, 435 cGy, 440 cGy, 445 cGy, 450 cGy, 455 cGy, 460 cGy, 465 cGy, 470 cGy, 475 cGy, 480 cGy, 485 cGy, 490 cGy, 495 cGy or at least 500 cGy.

Irradiation may be administered on the same day of solid-organ transplantation. In some cases, the plurality of irradiation doses may be delivered over a period of time after organ transplantation. In some cases, the plurality of irradiation doses may be delivered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days, 20 days, 20.5 days, 21 days, 21.5 days, 22 days, 22.5 days, 23 days, 23.5 days, 24 days, 24.5 days, 25 days, 25.5 days, 26 days, 26.5 days, 27 days, 27.5 days, 28 days, 28.5 days, 29 days, 30 days, 30.5 days, 31 days, 31.5 days, 32 days, 32.5 days, 33 days, 33.5 days, 34 days, 34.5 days, 35 days, 35.5 days, 36 days, 36.5 days, 37 days, 37.5 days, 38 days, 38.5 days, 39 days, 40 days, 40.5 days, 41 days, 41.5 days, 42 days, 42.5 days, 43 days, 43.5 days, 44 days, 44.5 days, 45 days, 45.5 days, 46 days, 46.5 days, 47 days, 47.5 days, 48 days, 48.5 days, 49 days or at least 50 days.

In some cases, the doses of irradiation are delivered on a regular interval over the course of administration. In other cases, the doses of irradiation are not delivered on a regular interval over the course of administration. For example, irradiation may be delivered to the thymus gland on days 1 through 4, and days 7 through 11 after transplantation.

The irradiation may be targeted to a particular location of the recipient's body. In some cases, the irradiation may be targeted to a tissue, an organ, a region of the body or the whole body. In some cases, irradiation may be targeted to the lymph nodes, the spleen, or the thymus or any other area known to a person of skill in the art. In some cases, the irradiation may be targeted to the same location when at least more than one dose of irradiation is delivered to the patient. In other cases, the irradiation may be targeted a different location when at least more than one dose of irradiation is delivered to the patient.

During non-myeloablative conditioning, recipients may be monitored for the development of conditions associated with non-myeloablative conditioning. Such diseases include neutropenia (e.g., granulocytes <2,000/mL), thrombocytopenia (e.g., platelets <60,000/mL) and secondary infections. In some cases, G-CSF (e.g., 10 µg/kg/day) may be administered for neutropenia. In some cases, any standard treatment known to one of skill in the art may be administered for thrombocytopenia or any secondary infections.

In some cases, non-myeloablative conditioning may be temporarily stopped if a recipient develops neutropenia, thrombocytopenia or any secondary infections. Non-myeloablative conditioning may be continued once neutropenia, thrombocytopenia and or any secondary infections are resolved. In some cases, if the recipient has a white blood count below 1,000 cells/mm$^3$, the recipient may be treated with G-CSF (e.g., 10 µg/kg/day) following non-myeloablative conditioning.

Immunosuppression and Graft Management

Following either HLA-matched or HLA-mismatched solid organ transplantation and administration of the engineered HLA-matched or HLA-mismatched hematopoietic cells, the recipient may receive an immunosuppressive regimen. The immunosuppressive regimen may have two phases, an induction phase and a maintenance phase. Induction and maintenance phase strategies may use different medicines at doses adjusted to achieve target therapeutic levels to enhance long term transplant persistence in the recipient. In some cases, the induction phase may begin perioperatively. In some cases, the induction phase may begin immediately after transplantation. In some cases, the induction phase may be both perioperative and immediately after transplantation. In some cases, the immunosuppressive regimen may continue as a maintenance therapy until the recipient achieves chimerism. For example, chimerism may be stable mixed chimerism as described herein.

In some cases, the immunosuppressive regimen may include one agent. In other cases, the immunosuppressive regimen may include more than one agent. For example, suitable agents for the immunosuppressive regimen may include a calcineurin inhibitor and/or an adjuvant. In some cases, the primary immunosuppressive agents include calcineurin inhibitors, which combine with binding proteins to inhibit calcineurin activity. In some cases, the calcineurin inhibitor may be tacrolimus, cyclosporine A, or any calcineurin inhibitor known to one of skill in the art and may be administered to the recipient at a dose effective to provide targeted immunosuppression as a calcineurin inhibitor.

In some cases, cyclosporine A may be withdrawn from the recipient after a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months.

In some cases, cyclosporine A may be withdrawn from the recipient after a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months.

In some cases, the dose of cyclosporine A may slowly be tapered if the recipient meets clinical criteria for lack of rejection and GVHD. For example, the total amount of the cyclosporine A administered may be reduced over time. In some cases, tapering of the cyclosporine A may occur for a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months such that at the end of the tapering regime, the dose of the cyclosporine A is tapered to zero. In some cases, tapering of the cyclosporine A may occur for a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months such that at the end of the tapering regime, the dose of the cyclosporine A is tapered to zero.

In some cases, the cyclosporine A may be delivered by a single dose to the recipient. In other cases, the recipient may receive more than one dose of cyclosporine A. For example, a recipient may receive at least one dose of cyclosporine A, two doses of cyclosporine A, three doses of cyclosporine A, four doses of cyclosporine A, five doses of cyclosporine A, six doses of cyclosporine A, seven doses of cyclosporine A, eight doses of cyclosporine A, nine doses of cyclosporine A, 10 doses of cyclosporine A, 11 doses of cyclosporine A, 12 doses of cyclosporine A, 13 doses of cyclosporine A, 14 doses of cyclosporine A, 15 doses of cyclosporine A, 16 doses of cyclosporine A, 17 doses of cyclosporine A, 18 doses of cyclosporine A, 19 doses of cyclosporine A, or 20 doses of cyclosporine A.

In some cases, a plurality of cyclosporine A doses may be delivered over a period of time after organ transplantation. In some cases, the plurality of cyclosporine A doses may be delivered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

In some cases, each dose of cyclosporine A may be at least 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, or at least 10 mg/kg.

In some cases, the amount of cyclosporine A administered to the patient may be determined by the amount of the cyclosporine A in the bloodstream. For example, the cyclosporine A may be administered at a dose to achieve a range of 0-40 mg, 5-50 mg, 10-60 mg, 15-65 mg, 20-70 mg, 25-75 mg, 30-80 mg, 35-85 mg, 40-90 mg, 45-95 mg, 50-100 mg, 55-105 mg, 60-110 mg, 65-115 mg, 70-120 mg, 75-125 mg, 80-130 mg, 85-135 mg, 90-140 mg, 95-145 mg, 100-150 mg, 105-155 mg, 110-160 mg, 115-165 mg, 120-170 mg, 125-175 mg, 130-180 mg, 135-185 mg, 140-190 mg, 145-195 mg, 150-200 mg, 160-210 mg, 170-220 mg, 180-230 mg, 190-240 mg, 200-250 mg, 210-260 mg, 220-270 mg, 230-280 mg, 240-290 mg, 250-300 mg, 260-310 mg, 270-320 mg, 280-330 mg, 290-340 mg, 300-350 mg, 310-360 mg, 320-370 mg, 330-380 mg, 340-390 mg, 350-400 mg, 360-410 mg, 370-420 mg, 380-430 mg, 390-440 mg, 400-450 mg, 410-460 mg, 420-470 mg, 430-480 mg, 440-490 mg, 450-500 mg, 46-510 mg, 470-520 mg, 480-530 mg, 490-540 mg, 500-550 mg, 510-560 mg, 520-570 mg, 530-580 mg, 540-590 mg, 550-600 mg, 560-610 mg, 570-620 mg, 580-630 mg, 590-640 mg, 600-650 mg, 610-660 mg, 620-670 mg, 630-680 mg, 640-690 mg, 650-700 mg or more than 700 mg.

In some cases, tacrolimus may be withdrawn from the recipient after a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months. In some cases, the dose of tacrolimus may slowly be tapered providing the recipient meets clinical criteria for lack of rejection and GVHD. For example, the total amount of tacrolimus administered may be reduced over time. In some cases, tapering of tacrolimus may occur for a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months such that at the end of the tapering regime, the dose of tacrolimus is tapered to zero.

In some cases, tacrolimus may be withdrawn from the recipient after a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months. In some cases, the dose of tacrolimus may slowly be tapered providing the recipient meets clinical criteria for lack of rejection and GVHD. For example, the total amount of tacrolimus administered may be reduced over time. In some cases, tapering of tacrolimus may occur for a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months such that at the end of the tapering regime, the dose of tacrolimus is tapered to zero.

In some cases, tacrolimus may be delivered by a single to the recipient. In other cases, the recipient may receive more than one dose of Tacrolimus. For example, a recipient may receive at least one dose of Tacrolimus, two doses of Tacrolimus, three doses of Tacrolimus, four doses of Tacrolimus, five doses of Tacrolimus, six doses of Tacrolimus, seven doses of Tacrolimus, eight doses of Tacrolimus, nine doses of Tacrolimus, 10 doses of Tacrolimus, 11 doses of Tacrolimus, 12 doses of Tacrolimus, 13 doses of Tacrolimus, 14 doses of Tacrolimus, 15 doses of Tacrolimus, 16 doses of Tacrolimus, 17 doses of Tacrolimus, 18 doses of Tacrolimus, 19 doses of Tacrolimus, or at least 20 doses of Tacrolimus.

In some cases, a plurality of tacrolimus doses may be delivered over a period of time after organ transplantation. In some cases, the plurality of tacrolimus doses may be delivered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 d days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

In some cases, each dose of tacrolimus may be at least 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, or at least 10 mg/kg.

In some cases, the amount of tacrolimus administered to the patient is determined by the amount of tacrolimus in the bloodstream. For example, tacrolimus may be administered at a dose to achieve a range of 0-40 mg, 5-50 mg, 10-60 mg, 15-65 mg, 20-70 mg, 25-75 mg, 30-80 mg, 35-85 mg, 40-90 mg, 45-95 mg, 50-100 mg, 55-105 mg, 60-110 mg, 65-115 mg, 70-120 mg, 75-125 mg, 80-130 mg, 85-135 mg, 90-140 mg, 95-145 mg, 100-150 mg, 105-155 mg, 110-160 mg, 115-165 mg, 120-170 mg, 125-175 mg, 130-180 mg, 135-185 mg, 140-190 mg, 145-195 mg, 150-200 mg, 160-210 mg, 170-220 mg, 180-230 mg, 190-240 mg, 200-250 mg, 210-260 mg, 220-270 mg, 230-280 mg, 240-290 mg, 250-300 mg, 260-310 mg, 270-320 mg, 280-330 mg, 290-340 mg, 300-350 mg, 310-360 mg, 320-370 mg, 330-380 mg, 340-390 mg, 350-400 mg, 360-410 mg, 370-420 mg, 380-430 mg, 390-440 mg, 400-450 mg, 410-460 mg, 420-470 mg, 430-480 mg, 440-490 mg, 450-500 mg, 46-510 mg, 470-520 mg, 480-530 mg, 490-540 mg, 500-550 mg, 510-560 mg, 520-570 mg, 530-580 mg, 540-590 mg, 550-600 mg, 560-610 mg, 570-620 mg, 580-630 mg, 590-640 mg, 600-650 mg, 610-660 mg, 620-670 mg, 630-680 mg, 640-690 mg, 650-700 mg or more than 700 mg.

The levels of either cyclosporine or tacrolimus in the recipient may be monitored. At the onset of immunosuppression, the levels of either cyclosporine or tacrolimus may be, for example, in the range of 0-15 ng/mL, 5-15 ng/mL, 10-20 ng/mL, 15-25 ng/mL, 20-30 ng/mL, 25-35 ng/mL, 30-40 ng/mL, 35-45 ng/mL or 40-50 ng/mL in the recipient. In some cases, the levels of either cyclosporine or tacrolimus may be reduced after a period of time in the recipient. For example, the period of time may be less than one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks or less than 33 weeks. In some cases, the levels of either cyclosporine or tacrolimus may be reduced to within the range of 0-1 ng/mL, 0.5-1.5 ng/mL, 1.0-2.0 ng/mL, 1.5-2.5 ng/mL, 2.0-3.0 ng/mL, 2.5-3.5 ng/mL, 3.0-4.0 ng/mL, 3.5-4.5 ng/mL, 4.0-5.0 ng/mL, 5.5-6.5 ng/mL, 6.0-7.0 ng/mL, 6.5-7.5 ng/mL, 7.0-8.0 ng/mL, 8.5-9.5 ng/mL or 9.0-10.0 ng/mL in the recipient.

In some cases, a calcineurin inhibitor may be administered to the recipient in combination with an inhibitor of purine metabolism (e.g., mycophenolate mofetil). For example, cyclosporine A and mycophenolate mofetil may be used in the case of kidney transplantation.

In some cases, the adjuvant may be withdrawn from the recipient after a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months. In some cases, the dose of the adjuvant may slowly be tapered providing the recipient meets clinical criteria for lack of rejection and GVHD. For example, the total amount of the adjuvant administered may be reduced over time. In some cases, tapering of the adjuvant may occur for a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months such that at the end of the tapering regime, the dose of the purine metabolism inhibitor is tapered to zero.

In some cases, the adjuvant may be withdrawn from the recipient after a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months. In some cases, the dose of the adjuvant may slowly be tapered providing the recipient meets clinical criteria for lack of rejection and GVHD. For example, the total amount of the adjuvant administered may be reduced over time. In some cases, tapering of the adjuvant may occur for a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months such that at the end of the tapering regime, the dose of the purine metabolism inhibitor is tapered to zero.

Adjuvant agents may be used to enhance immunosuppression while decreasing the dose and toxicity of other individual agents that are part of the immunosuppressive regimen. In some cases, adjuvant agents may be combined with a calcineurin inhibitor. For example, adjuvant agents may include steroids, azathioprine, mycophenolate mofetil, sirolimus, an antibody or any adjuvant agent known to one of skill in the art and may be administered to the recipient at a dose effective to enhance immunosuppression.

In some cases, antibody-based therapy may be used to avoid or reduce the dose of calcineurin inhibitors in the immunosuppressive regimen. For example, antibody-based therapy may include monoclonal (e.g., muromonab-CD3) antibodies, polyclonal antibodies and/or anti-CD25 antibodies (eg, basiliximab, daclizumab). In some cases, antibody-based therapy may be administered during the early post-transplant period. For example, early post-transplant may be up to 8 weeks following the transplant.

Graft management may include preventing, inhibiting or suppressing acute rejection with immunosuppressive drugs. In some cases, multiple agents may be used to prevent, inhibit or suppress episodes of acute rejection. For example, an agent may be a steroid. In some cases, one or more than one steroid may be used to prevent, inhibit or suppress episodes of acute rejection. Any steroid known to one of skill in the art suitable for preventing, inhibiting or suppressing acute rejection may be used. For example, any dose, mode of administration and duration of administration for any steroid known to one of skill in the art suitable for preventing, inhibiting or suppressing acute rejection may be used. In some cases, administration of the steroid may be tapered to a maintenance dose.

For example, an agent may be antithymocyte globulin. In some cases, antithymocyte globulin may be used to prevent, inhibit or suppress episodes of acute rejection. Any dose, mode of administration and duration of administration for antithymocyte globulin suitable for preventing, inhibiting or suppressing acute rejection may be used. In some cases, administration of antithymocyte globulin may be tapered to a maintenance dose.

For example, an agent may be muromonab-CD3. In some cases, muromonab-CD3 may be used to prevent, inhibit or suppress episodes of acute rejection. Any dose, mode of administration and duration of administration for muromonab-CD3 suitable for preventing, inhibiting or suppressing acute rejection may be used. In some cases, administration of muromonab-CD3 may be tapered to a maintenance dose.

Chimerism

Following either HLA-matched or HLA-mismatched solid organ transplantation and administration of the engineered HLA-matched or HLA-mismatched hematopoietic cells, the recipient may be monitored for chimerism. Recipients who exhibit greater than 95% donor cells in a given blood cell lineage by any analysis to determine chimerism at any time post-transplantation may be classified as having full donor chimerism. In some cases, mixed chimerism may be greater than 1% donor-derived cells of a given lineage but less than 95% donor-derived DNA.

The relative dose of CD3+ cells and CD34+ cells, and the total dose of these cells, can influence whether an individual develops stable mixed chimerism. In some cases, for example where the CD3+ cells and the CD34+ cells are HLA matched between donor and recipient, the dose of CD3+ cells can be at least about $1 \times 10^6$ cells/kg and the dose of CD34+ cells can be at least about $0.5 \times 10^6$/kg. In some cases, where the CD3+ cells and the CD34+ cells are HLA mismatched between donor and recipient, the dose of CD3+ cells can be at least about $10 \times 10^6$ cells/kg and may be less than $50 \times 10^7$ cells/kg, and the dose of CD34+ cells can be at least about $1 \times 10^6$/kg, at least about $5 \times 10^6$/kg, at least about $10 \times 10^6$/kg, at least $15 \times 10^6$/kg or more. Where the dose of CD34+ cells is less than $15 \times 10^6$/kg it may be desirable to administer a higher dose of CD3+ cells, e.g. up to about $25 \times 10^6$/kg, up to about $30 \times 10^6$/kg, up to about $35 \times 10^6$/kg, up to about $40 \times 10^6$/kg, up to about $45 \times 10^6$/kg, up to about $50 \times 10^6$/kg.

HLA matched patients there needs to be at least injected, but in the case of HLA mismatched there needs to be at least $10 \times 10^{\wedge}6$ T cells/kg injected along with CD34 cells to achieve persistent mixed chimerism for at least 6 months. If the CD34 cell dose is below $15 \times 10^{\wedge}6$ cells/kg in mismatched patients, then at least $50 \times 10^{\wedge}6$ T cells/kg is needed.

Individuals who exhibit mixed chimerism may be further classified according to the evolution of chimerism, where improving mixed chimerism may be a continuous increase in the proportion of donor cells over a period of time (e.g., at least a 6-months). In some cases, stable mixed chimerism may include fluctuations in the percentage of recipient cells over time, without complete loss of donor cells.

The doses of CD34+ and CD3+ cells used in the engineered hematopoietic cell composition are selected in order to achieve stable mixed chimerism in the recipient after transplant. Mixed chimerism is defined as greater than 1% recipient DNA. In some cases, mixed chimerism may include a percentage of cells derived from the donor and a percentage of cells derived from the recipient. In some cases, mixed chimerism is more than 70% of the cells in the recipient being derived from the donor. In other cases, mixed chimerism is more than 10% of the cells in the recipient being derived from the donor, more than 15% of the cells in the recipient being derived from the donor, more than 20% of the cells in the recipient being derived from the donor, more than 25% of the cells in the recipient being derived from the donor, more than 30% of the cells in the recipient being derived from the donor, more than 35% of the cells in the recipient being derived from the donor, more than 40% of the cells in the recipient being derived from the donor, more than 45% of the cells in the recipient being derived from the donor, more than 50% of the cells in the recipient being derived from the donor, more than 55% of the cells in the recipient being derived from the donor, more than 56% of the cells in the recipient being derived from the donor, more than 57% of the cells in the recipient being derived from the donor, more than 58% of the cells in the recipient being derived from the donor, more than 59% of the cells in the recipient being derived from the donor, more than 60% of the cells in the recipient being derived from the donor, more than 61% of the cells in the recipient being derived from the donor, more than 62% of the cells in the recipient being derived from the donor, more than 63% of the cells in the recipient being derived from the donor, more than 64% of the cells in the recipient being derived from the donor, more than 65% of the cells in the recipient being derived from the donor, more than 66% of the cells in the recipient being derived from the donor, more than 67% of the cells in the recipient being derived from the donor, more than 68% of the cells in the recipient being derived from the donor, more than 69% of the cells in the recipient being derived from the donor, more than 70% of the cells in the recipient being derived from the donor, more than 71% of the cells in the recipient being derived from the donor, more than 72% of the cells in the recipient being derived from the donor, more than 73% of the cells in the recipient being derived from the donor, more than 74% of the cells in the recipient being derived from the donor, more than 75% of the cells in the recipient being derived from the donor, more than 76% of the cells in the recipient being derived from the donor, more than 77% of the cells in the recipient being derived from the donor, more than 78% of the cells in the recipient being derived from the donor, more than 79% of the cells in the recipient being derived from the donor, more than 80% of the cells in the recipient being derived from the donor, more than 81% of the cells in the recipient being derived from the donor, more than 82% of the cells in the recipient being derived from the donor, more than 83% of the cells in the recipient being derived from the donor, more than 84% of the cells in the recipient being derived from the donor, more than 85% of the cells in the recipient being derived from the donor, more than 86% of the cells in the recipient being derived from the donor, more than 87% of the cells in the recipient being derived from the donor, more than 88% of the cells in the recipient being derived from the donor, more than 89% of the cells in the recipient being derived from the donor, more than 90% of the cells in the recipient being derived from the donor, more than 91% of the cells in the recipient being derived from the donor, more than 92% of the cells in the recipient being derived from the donor, more than 93% of the cells in the recipient being derived from the donor, more than 94% of the cells in the recipient being derived from the donor, more than 95% of the cells in the recipient being derived from the donor, more than 96% of the cells in the recipient being derived from the donor, more than 97% of the cells in the recipient being derived from the donor, more than 98% of the cells in the recipient being derived from the donor ore more than 99% of the cells in the recipient being derived from the donor.

Mixed chimerism may be stable following a transplant using the CD34+/CD3+ engineered hematopoietic cell composition described herein. In some cases, mixed chimerism is stable. In some cases, stable mixed chimerism lasts for at least 6 months after treatment with any engineered hematopoietic cell composition of CD34+/CD3+ cells described herein. In some cases, stable mixed chimerism may persist for more than five days, more than 10 days, more than 15 days, more than 20 days, more than 25 days, more than 30 days, more than 35 days, more than 40 days, more than 45 days, more than 50 days, more than 55 days, more than 60 days, more than 65 days, more than 70 days, more than 75 days, more than 80 days, more than 85 days, more than 90 days, more than 95 days, more than 100 days, more than 105 days, more than 110 days, more than 115 days, more than 120 days, more than 125 days, more than 130 days, more than 135 days, more than 140 days, more than 145 days, more than 150 days, more than 155 days, more than 160 days, more than 165 days, more than 170 days, more than 175 days, more than 180 days, more than 185 days, more than 190 days, more than 195 days, more than 200 days, more than 205 days, more than 210 days, more than 215 days, more than 220 days, more than 225 days, more than 230 days, more than 235 days, more than 240 days, more than 245 days, more than 250 days, more than 255 days, more than 260 days, more than 265 days, more than 270 days, more than 275 days, more than 280 days, more than 285 days, more than 290 days, more than 295 days, more than 300 days, more than 305 days, more than 310 days, more than 315 days, more than 320 days, more than 325 days, more than 330 days, more than 335 days, more than 340 days, more than 345 days, more than 350 days, more than 355 days, more than 360 days, more than 365 days, more than 370 days, more than 375 days, more than 380 days, more than 385 days, more than 390 days, more than 395 days, more than 400 days, more than 405 days, more than 410 days, more than 415 days, more than 420 days, more than 425 days, more than 430 days, more than 435 days, more than 440 days, more than 445 days, more than 450 days, more than 455 days, more than 460 days, more than 465 days, more than 470 days, more than 475 days, more than 480 days, more than 485 days, more than 490 days, more than 495 days, or more than 500 days.

Mixed chimerism may be determined by measuring the percentage of donor cells for a single cell type within the recipient. For example, mixed chimerism may be determined by the percentage of donor-derived granulocytes in the recipient. In some cases, mixed chimerism may be determined by measuring the percentage of donor cells for a plurality of cell types within the recipient. For example, mixed chimerism may be determined by the percentage of donor-derived granulocytes, natural killer cells, B cells and T cells in the recipient.

In some cases, the percentage of donor-derived granulocytes in the recipient may be measured. In some cases, the percentage of donor-derived granulocytes may be constant in the recipient after transplantation. In other cases, the percentage of donor-derived granulocytes may not be constant in the recipient after transplantation. In other cases, the percentage of donor-derived granulocytes changes over time in the recipient after transplantation. For example, over a period of 60 days after transplantation, the percentage of donor-derived granulocytes in the recipient may be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

In some cases, the percentage of donor-derived natural killer cells in the recipient may be measured. In some cases, the percentage of donor-derived natural killer cells may be constant in the recipient after transplantation. In other cases, the percentage of donor-derived natural killer cells may not be constant in the recipient after transplantation. In other cases, the percentage of donor-derived natural killer cells changes over time in the recipient after transplantation. For example, over a period of 60 days after transplantation, the percentage of donor-derived natural killer cells in the recipient may be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

In some cases, the percentage of donor-derived B cells in the recipient may be measured. In some cases, the percentage of donor-derived B cells may be constant in the recipient after transplantation. In other cases, the percentage of donor-derived B cells may not be constant in the recipient after transplantation. In other cases, the percentage of donor-derived B cells change over time in the recipient after transplantation. For example, over a period of 60 days after transplantation, the percentage of donor-derived B cells in the recipient may be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

In some cases, the percentage of donor-derived T cells in the recipient may be measured. In some cases, the percentage of donor-derived T cells may Te constant in the recipient after transplantation. In other cases, the percentage of donor-derived T cells may not be constant in the recipient after transplantation. In other cases, the percentage of donor-derived T cells change over time in the recipient after transplantation. For example, over a period of 60 days after transplantation, the percentage of donor-derived T cells in the recipient may be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

There are a plurality of methods of testing for chimerism that are readily available and known to those of skill in the art. Any method of testing for chimerism that distinguishes donor or recipient origin of a cell is suitable for use in the methods described herein.

In some cases, the methods of testing for chimerism may include genetic based methods. For example, polymerase chain reaction (PCR) based methods which utilize probes may be used. In some cases, probes for PCR based methods may be probes for microsatellite analysis. For another example, commercial kits that distinguish polymorphisms in short terminal repeat lengths of donor and host origin are readily available and known to those of skill in the art.

In some cases, major histocompatibility complex (MHC) typing may be used for testing chimerism. For example, MHC typing may be used to test the type of cells in the blood. In some cases, MHC typing may be used in combination with flow cytometry. In some case, an analysis of HLA-stained cells by flow cytometry may be performed.

The methods described herein are provided such that a recipient may achieve stable mixed chimerism sufficient to allow withdrawal of immunosuppressive drugs. For example, withdrawal of immunosuppressive drugs may include tapering immunosuppressive drugs. In other cases, withdrawal of immunosuppressive drugs may include immediate withdrawal of immunosuppressive drugs. In some cases, mixed chimerism persists for at least six months prior to withdrawal of immunosuppressive drugs. In other cases, mixed chimerism persists for at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. In some cases, the dose of the adjuvant may slowly be tapered providing the recipient meets clinical criteria for lack of rejection and GVHD. For example, the total amount of the adjuvant administered may be reduced over time. In some cases, tapering of the adjuvant may occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In some cases, a lack of rejection episodes may coincide with mixed chimerism prior to withdrawal of immunosuppressive drugs. In some cases, a lack of rejection episodes may be consistent for at least six months prior to withdrawal of immunosuppressive drugs. In other cases, a lack of rejection episodes may be consistent for at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. In some cases, the dose of the adjuvant may slowly be tapered providing the recipient meets clinical criteria for lack of rejection and GVHD. For example, the total amount of the adjuvant administered may be reduced over time. In some cases, tapering of the adjuvant may occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In some cases, a lack of GVHD and lack of rejection episodes coincides with mixed chimerism prior to withdrawal of immunosuppressive drugs. In some cases, a lack of GVHD and lack of rejection episodes may be consistent for at least six months prior to withdrawal of immunosuppressive drugs. In other cases, a lack of GVHD and lack of rejection episodes may be consistent for at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. In some cases, the dose of the adjuvant may slowly be tapered providing the recipient meets clinical criteria for lack of rejection and GVHD. For example, the total amount of the adjuvant administered may be reduced over time. In some cases, tapering of the adjuvant may occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In order to determine if tapering of the immunosuppressive regimen is appropriate for the recipient, the recipient may be tested for mixed chimerism, usually at regular intervals. For example, regular intervals may be monthly, semi-monthly, weekly, bi-monthly, annually, bi-annually or the like.

The invention now being fully described, it is apparent to one of ordinary skill in the art that various changes and modifications can be made without departing from the spirit or scope of the invention.

EXAMPLES

The present disclosure has been described in terms of particular cases found or proposed to comprise preferred modes for the practice of the disclosure. It is appreciated by those of skill in the art that, in light of the present disclosure, numerous modifications and changes can be made in the particular embodiments exemplified without departing from the intended scope of the disclosure. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

For further elaboration of general techniques useful in the practice of this disclosure, the practitioner can refer to standard textbooks and reviews in cell biology, tissue culture, and embryology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following examples are put forth so as to provide those of ordinary skill in the art with a complete disclosure and description of how to make and use the present disclosure and are not intended to limit the scope of what is regarded as the disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1—TLI and ATG Conditioning for Combined Kidney and Blood Stem Cell Transplantation Immune tolerance to HLA haplotype matched living related donor kidney allografts is developed in order to remove the requirement for the lifelong use of immunosuppressive drugs and to improve the long term graft survival. Currently, these haplotype matched recipients account for about half of living related donor kidney transplants performed at most medical centers in the United States. During the past 10 years an increasing proportion of grafts in most centers were from living related donors as an alternative to cadaver grafts. Although the living related donor transplants have improved survival as compared to cadaver transplants, about 40 to 50% of the living donor grafts are still lost within about 10 years. In addition, the recipients usually receive a mixture of 3 maintenance immunosuppressive drugs including a calcineurin inhibitor, prednisone, and mycophenolate mofetil. The latter drugs have side effects that include hypertension, nephrotoxicity, and heart disease that contribute to long term patient disability and graft loss.

Our preclinical studies showed that conditioning with TLI and ATG is advantageous for inducing tolerance after combined organ and bone marrow transplantation because the conditioning regimen prevents GVHD as compared to TBI. Approximately 1,000 fold more donor T cells are needed to induce lethal GVHD using TLI/ATG as compared to TBI conditioning. The basis of protection against GVHD is the change in the balance of residual host T cells that favors the host natural killer (NK) T cell subset. The latter cells become the predominant T cell subset in TLI/ATG conditioned mice and produce large amounts of IL-4 that polarize conventional donor T cells toward a Th2 bias, thereby attenuating GVHD. Several laboratories have shown that NK T cells that survive in vivo irradiation are themselves polarized toward a Th2 bias.

Based on the protective effect of TLI/ATG against GVHD in the preclinical studies, this conditioning regimen has been successfully tested as a non-myeloablative regimen for HLA matched cell transplantation for patients. Modifications were made in the conditioning regimen and make-up of the hematopoetic cell graft for the adaptation. The hematopoietic cell graft was "engineered" to contain a defined number of purified CD34+ hematopoietic progenitor cells selected by immunomagnetic bead columns and a defined number of donor T cells. Other aspects of the conditioning regimen remained the same, including the TLI and ATG schedule. A post-transplant immunosuppressive regimen of 1 month of MMF and 6 months of cyclosporine was adapted from standard protocols for patients receiving hematopoietic cell transplants to treat leukemia and lymphoma. Of note, the conditioning regimen was performed with the start of transplant surgery on day 0, and infusion of donor hematopoietic cells was administered on day 11. This allowed for the further adaptation of the protocol to cadaver transplants in the future, and was the schedule used in the numerous preclinical studies of combined transplantation using TLI/ATG.

Twenty patients were given combined HLA matched grafts, followed up from between 5 to 86 months. Nineteen of these became chimeras without the development of GVHD. Seventeen developed persistent chimerism (>6 months), and of these 14 were withdrawn from immunosuppressive drugs, 2 of the 17 patients are undergoing drug tapering, and 4 of 20 failed drug withdrawal (either due to failure to maintain chimerism for >6 months, or due to rejection episodes). All 20 patients currently had excellent graft function at the last observation point, and were discharged about 5 hospital days after transplant surgery. The patients needed 3-16 CD34+ cell/kg and 1×106 CD3+ cell/Kg.

In order to apply the tolerance protocol described above to HLA mismatched patients, adjustments in the doses of CD34+ and CD3+ donor cells were made based on preliminary studies of 17 HLA halotype mismatched patients who were given the TLI and ATG conditioning regimen and a donor cell transplant to treat leukemia or lymphoma. The dose of CD34+ cells was gradually escalated to ≥10×106 cell/Kg and the CD3+ dose was gradually escalated to 10×106 cells/kg. The majority of patients given the latter cell dose achieved mixed chimerism whereas none of the patients given cell doses lower than these levels achieved mixed chimerism. Accordingly, a dose escalation clinical study was performed on 4 HLA haplotype matched patients given combined kidney and hematopoietic cell transplants with the goal of achieving target doses of ≥10×106/Kg CD34+ cells and ≥10 xl06/Kg CD3+ cells. The purpose of the study was to determine whether the achievement of these target doses would result in the development of mixed chimerism for >6 months and the ability to withdraw immunosuppressive drugs thereafter. Some details of the clinical protocol are given below.

The gene array testing indicates that there is a change in the pre to post-transplant gene expression profiles in patients who met drug withdrawal criteria such that their profiles became considerably better matched to those of the rare "operationally" tolerant patients who stopped conventional immunosuppressive drugs and did not develop graft rejection at their first monitoring time point. This was not the case with the patients who failed to meet withdrawal criteria. The differences in gene expression pattern between the 2 groups decreased at later time points. It should be noted that the "operationally" tolerant patients were all HLA mismatched. This indicates that the tolerant gene expression profiles can be used to predict the tolerant state in both matched and mismatched patients.

Clinical Protocol

This was a single-center, open-label study in adult renal transplant patients. Patients received TLI, RATG and an infusion of G-CSF "mobilized blood" mononuclear cells that had been enriched for CD34+ cells and contained a defined number of CD34+ and CD3+ donor cells. Immunosuppressive drugs consisted of 9 months of mycophenolate mofetil (MMF; 15 mg/Kg twice per day starting on day 10), and a tapering course of daily tacrolimus starting on day 0 that is discontinued at a target of 12 months. The immunosuppressive drug combination of a calcineurin inhibitor and a purine metabolism inhibitor was similar to that used previously. At serial time points (1) graft function was monitored, (2) chimerism was measured in recipient white blood cell subsets and (3) protocol biopsies of the graft is obtained. If chimerism failed to develop or is lost during the first six months, or if a rejection episode or GVHD occurred or if there was histological evidence of rejection in graft biopsies then tacrolimus and/or MMF was not withdrawn, and the patient would be followed thereafter as a treatment failure. Recipients in the study were given a target dose of ≥10×106 CD34+ cells/Kg and an escalating dose of T cells to achieve the target dose of 1×107/Kg T cells from the "mobilized" peripheral blood mononuclear cells harvested from the donor. Of the 4 patients enrolled in the protocol, 2 did not receive the target cell doses and 2 did (Table 1).

Study Therapies. During the course of this study, patients receive 5 intravenous injections of rabbit ATG (Thymoglobulin), a total of 1,200 cGy of total lymphoid irradiation, a single infusion of donor cells, transient immunosuppression (MMF and Tacrolimus), and prophylactic anti-viral, anti-fungal and antibacterial agents.

Patients receive a total of 5 intravenous doses of Thymoglobulin over a 5 day period; each dose is 1.5 mg/kg. Thymoglobulin is administered on the day of transplantation (intra-operatively before the transplanted organ is perfused with host blood) and on the subsequent 4 days post-transplant.

Patients receive ten treatments of fractionated irradiation (120 cGy each) targeted to the lymph nodes, spleen and thymus gland on days 1 through 4, and days 7 through 11, after transplantation such that the total dose of TLI is 1,200 cGy. Two doses are given on day 10 or 11 to achieve a total of 10 doses. TLI is given to the inverted Y and mantle fields. During the administration of TLI, patients are monitored for the development of neutropenia (granulocytes <2,000/mL), thrombocytopenia (platelets <60,000/mL) and infection. TLI is withheld for any of these problems, and G-CSF (10 μg/kg/day) is given for neutropenia. TLI is reinstated once neutropenia and/or thrombocytopenia resolves. At the completion of TLI, all patients are given G-CSF (10 μg/kg/day) if the white blood cell count is below 1,000 cells/mm3. TLI is completed by day 11 if no doses are withheld.

A single intravenous infusion of cryopreserved HLA-haplotype matched living related donor, G-CSF mobilized blood mononuclear cells (recovered from donor peripheral blood using apheresis), that has been "engineered" is administered to patients on the day of completion of TLI. Harvesting of donor cells is performed in the following fashion: Approximately 6 weeks before renal transplantation, the donor is given G-CSF daily (16 mg/kg/day) for five days, and mononuclear cells are harvested by an apheresis of up to 20 liters according to procedures previously approved by the Stanford Committee on Medical Human Subjects for HLA-haplotype matched peripheral blood stem cell (PBSC) transplantation. In addition, a second session of up to 12 liters may be carried out for optimal cell recovery. Cells are selected for CD34+ cells on Isolex columns, Column flow through is collected also. Both CD34+ cells and flow through cells are cryopreserved and thawed according to standard procedures at the Stanford Blood and Marrow Transplantation laboratory. The target dose of CD34+ cells to be injected is ≥10×106 cells/kg. A defined target dose of (1×107/kg CD3+) T cells is administered by injecting column flow through cells along with enriched CD34+ cells intravenously. The dose of flow through cells are calculated based on the content of CD3+ cells determined by immunofluorescent staining. This dose was used in the 17 haplotype matched patients with leukemia and lymphoma. The majority of these patients developed persistent mixed chimerism, and none developed acute GVHD. The dose of T cells is increased if the first 3 recipients of combined transplants fail to achieve persistent chimerism, and is decreased if the first 3 recipients develop complete chimerism or if any patient develops GVHD.

Corticosteroid therapy was limited to 60-120 mg Solumedrol (I.V.) as premedication on the days of ATG infusions to reduce ATG side effects. After the last dose of ATG, a tapering course of prednisone starting at 30 mg/d and reducing by 5 mg/d is given until day 10.

MMF therapy commenced on the day of the donor cell infusion (day 10) at 15 mg/Kg twice per day. MMF therapy was maintained for 6 months, and then tapered and stopped at 9 months.

Tacrolimus was started on day 0, adjusted to achieve a standing whole blood trough level. As long as the criteria for immunosuppressive drug tapering are met, Tacrolimus was tapered beginning at month 9, and stopped by month 12.

Criteria for continued tapering of immunosuppressive drugs (Tacrolimus) through month 12 and MMF through month 9 were as follows: 1) Sustained chimerism for at least 6 months; 2) No clinical rejection episodes; 3) Protocol biopsies show no evidence of acute or chronic rejection; 4) No GVHD. Patients who do not meet these criteria are considered treatment failures, and further tapering of drugs is not performed.

If acute or chronic GVHD is observed that would ordinarily be treated with immunosuppressive drugs, then the patient is considered a treatment failure. Immunosuppressive drugs are administered according to standard practice.

Rejection episodes are treated with standard anti-rejection therapy which includes the use of intravenous methyl prednisolone and the patient is considered a treatment failure. If no response to two courses of steroids is found, then a course of anti-lymphocyte antibody is given. Tacrolimus is given at conventional doses during rejection episodes. Once a rejection episode occurs, patients will return to conventional doses of maintenance immunosuppressive drugs and no further tapering is attempted as per the protocol above. Currently 95% of acute rejection episodes are reversed.

Since the initial course of TLI and ATG is expected to induce a marked depletion of T cells, there is an increased risk of new or recrudescent viral infection, including cytomegalovirus (CMV), Epstein-Barr virus, Herpes zoster and Herpes simplex viruses as compared to conventional immunosuppressive protocols. Anti-viral prophylaxis for CMV is given as follows: Valganciclovir (900 mg/d:P.O.) was given for the first 14 days adjusted for renal function or during the first 14 days, ganciclovir (DHPG), 5 mg/kg, is given IV adjusted for renal function. After the 14-day course all protocol transplant recipients were placed on the valganciclovir (900 mg/d) adjusted for renal function. This was continued for a minimum of 90 days and if the absolute lymphocyte count is under 400, is continued until the time of steroid discontinuation.

Bactrim (1 single strength tablet per day) was given orally for one year for prophylaxis of *Pneumocystis carinii* pneumonia (PCP) and Mycostatin mouthwashes daily for three weeks for *candida* prophylaxis. Standard peri-operative antibiotics will include Ancef (1 mg, i.v., 3 doses at 8-hour intervals) and Gentamicin (1.7 mg/kg, i.v., one dose at the time of transplant). Antibacterial agents are subject to appropriate substitution according to patient allergies.

A surveillance biopsy is performed just before all immunosuppressive drugs are stopped posttransplant. In addition, "for-cause" biopsies are obtained within 48 hours of an unexplained or unresolved 20% increase in serum creatinine.

Of the two patients who failed to receive the targeted cell doses, patient #1 failed to have mixed chimerism persist for more than 1 month. This patient received 3×106 CD3+ cells/Kg as part of the dose escalation study, but did receive the targeted number of CD34+ cells/Kg. This patient was not withdrawn from immunosuppressive drugs, and remains on Tacrolimus and MMF with good graft function.

Patients #2 and #3 received the targeted cell dose of CD3+ T cells (10×106 cells/Kg) and the targeted dose of CD34+ cells. Both patients developed persistent mixed chimerism for 10 months and 5 months respectively at present, and meet drug withdrawal criteria. The pattern of persistent mixed chimerism is shorter for patient #3 in FIG. 2.

Patient #4 received 10×106 CD3+ cells/Kg but did not meet the requisite number of CD34+ cells due to poor mobilization of the donor CD34+ cells despite two courses of G-CSF administered to the donor. This patient failed to develop chimerism, and remains on immunosuppressive drugs with good graft function.

Example 2. Effect of T Cell Dose on Development of Mixed Chimerism

Patients were transplanted as described in Example 1. The HLA-matching characteristics, conditioning regiment and donor cell composition were performed according to Table 1.

TABLE 1

| Patient # months post-transplant | Age/ Gender | ESRD Cause | Total Dose TLI (cGy) | CD34+ Cell Dose (×10⁶/kg) | CD3+ Cell Dose (×10⁶/kg) | Serum Creatinine at last observation (mg/dL) | Duration of Chimerism | Chimerism (>30% donor type cells) |
|---|---|---|---|---|---|---|---|---|
| 1 (37 mo) | 47/M | IgA | 1200 | 11.8 | 3 | 1.7 | 1 mo | − |
| 2 (19 mo) | 24/F | SLE | 1200 | 14.5 | 10 | 1.1 | 12 mo | + |
| 3 (16 mo) | 35/F | unknown | 1200 | 21.9 | 10 | 1.1 | 12 mo | + |
| 4 (16 mo) | 33/M | Unknown | 1200 | 9 | 10 | 1.4 | <1 mo | − |
| 5 (7 mo) | 26/F | SLE | 1200 | 7.5 | 10 | 1.1 | <1 mo | − |
| 6 (4 mo) | 21/M | FSG | 1200 | 7.5 | 20 | 1.3 | <1 mo | − |
| 7 (4 mo) | 47/F | GN | 1200 | 11.0 | 20 | 1.3 | 1 mo | − |
| 8 (2 mo) | 26/F | MGN | 1200 | 8.8 | 50 | 1.3 | >1 mo | + |
| 9 (2 mo) | 55/M | FGN | 1200 | 11.0 | 50 | 1.5 | >1 mo | + |

Figure 4A:
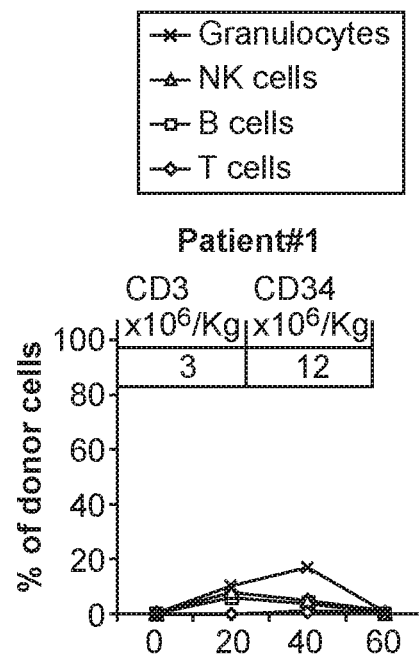
FIG. 4A-4D provide a graph assessment of chimerism for 4 different recipients. Each recipient is shown in one of panels FIG. 4A, FIG. 4B, FIG. 4C and FIG. 4D. The number of CD34+ and CD3+ cells administered to the recipient is shown above the graph.
Figure 4B:
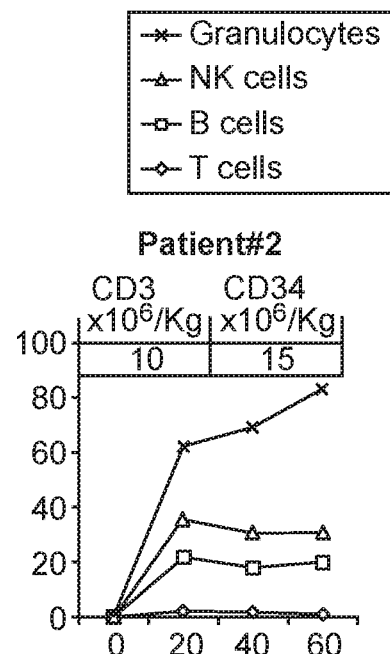
Figure 4C:
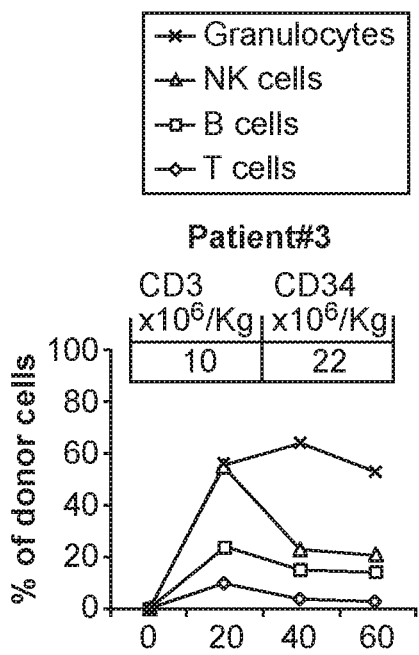
Figure 4D:
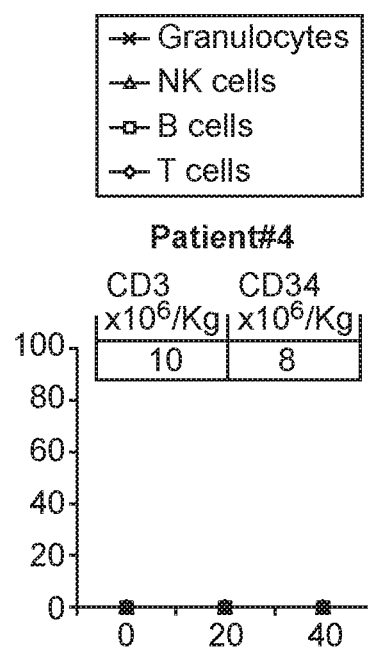

As shown by these data and in FIG. 4, in individuals receiving an HLA mismatched hematopoietic cell transplantation, stable mixed chimerism can be obtained with a high dose of CD3+ cells, up to 50×10⁷/kg, and this dose of T cells can overcome low numbers of CD34+ cells. For example, patient 7 and 9 received the same dose of CD34+ cells, but only patient 9, who received a high T cell dose, achieved mixed chimerism.

Example 3—Collection of Peripheral Blood Progenitor Cells for Use in a Hematopoietic Cell Transplantation To collect peripheral blood progenitor cells that are adequate in quality and quantity, which will result in acceptable progenitor cell viability and recovery for a hematopoietic transplant. This type of procedure may be performed on potential BMT transplant patients or donors as well as for storage purposes.

To collect lymphocytes from a donor where the goal is to create a graft versus leukemia effect.

To collect dendritic cells or another cell line for a research study.

For patients weighing less than 40 Kg see the Pediatric COBER® Spectra™ Procedure for procedure location, blood or albumin prime criteria and other age specific issues.

TABLE 2

| | |
|---|---|
| White Blood Cell Set-Functionally Closed | A functionally closed COBE Spectra disposable tubing set that allows for the addition of anticoagulant to the product bag and in-run or post-procedure sampling. |
| Sample Bulb Assembly | The sample bulb assembly consists of 2 sample bulbs with sampling ports, a Y connector, 3 slide clamps and tubing leading to the product bag. |
| Sample Bulb | A 4 ml plastic bulb for obtaining and removing a product sample. |
| Sampling Port | A port connected to each sample bulb that allows removal of product sample with a blunt needle and syringe. |
| Accessory Line | The accessory line is connected to the collect line and includes a sterile barrier filter with leer connection, a frangible, and a slide clamp. |
| Frangible | A breakable barrier that prevents product from draining into the sterile barrier filter until the nurse is ready to add anticoagulant. |
| Sterile Barrier Filter | A 0.2 micron filter that allows the addition of anticoagulant to the product bag while maintaining a functionally closed tubing set. |

Tubing Installation

Powered on the apheresis machine (e.g., Spectra) to perform a short self-check to ensure the power supplies are operating at the correct voltages. Verified that the "cobe spectra (version_software)" is displayed, the yellow warning led illuminates, the pause led flashes, the cartridge clamps are in unload position, the single stage filler is in place. The disposable set package was placed on the centrifuge cover and paper tapes removed. The package was held securely by placing underneath the hook on front panel.

The inlet coil was removed and hung to ensure access connection on hook on left side of iv pole. The access saline (green) line was placed over the top of the machine. The return line coil was removed and return connection hung on the hook on left side of iv pole. The return saline line was placed over the top of the machine. The bags were hung on iv pole from left to right: ac far left; saline; waste; plasma; product bag on right. The slide clamp was closed between the product bag and the y connector on the sample bulb assembly to prevent product from entering it prematurely. The return pump cartridge was removed from right side of package and snapped into cartridge clamp between plasma and collect/replace pumps.

The access pump cartridge was removed from left side of package and snapped into cartridge clamp between ac and inlet pumps. (cobe labels on cartridges should be upright and facing out. The ac line in ac detector was placed and program continued to load the tubing into pumps. The lines were placed in collect/replace and plasma valves.

The return pressure sensor was placed in its housing and pushed downward and turned clockwise to lock in place. The rbc line was placed in the rbc valve, completely inserted in rbc detector. The return and inlet air chambers were positioned in air detectors with the waste divert lines forward. Air chamber filters were positioned so the top of the chambers were aligned with the air detector housings. The protective caps were removed from the male/female leer connectors above the return air chamber and the waste divert lines placed in waste divert valve assembly. The "y" was pushed in first, then "flossed" the tubing back into place.

The line was placed in the centrifuge pressure sensor housing and the access pressure sensor was placed in its housing, pushed downward and turned clockwise to lock it in place. The return (blue) line was placed in return valve so line sat horizontally through center of valve. The channel was removed from package.

The device was unlocked, and placed in the centrifuge. The centrifuge was rotated such that the loading port was open to the front and the centrifuge collar holder rested on outer rim of the filler. The tubing that was connected to the channel was extended and the centrifuge rotated clockwise several times to ensure tubing did not twist and upper bearing remained in place. The centrifuge door was closed and covered prior to running a standard priming procedure for the disposable tubing set.

Connect Patient and Perform Apheresis

Using Catheter for Access:

the catheter was clamped and the hub connection prepped with an alcohol wipe. The needleless connector was removed and hub and threads cleaned vigorously with a new alcohol wipe. The vacutainer holder was attached and pinch clamp on catheter opened. The first 5 ml drawn from catheter was placed in the waste draw and the lab specimens were drawn. The pinch clamp on the catheter was closed, the attached needle removed from the spectra access line the access line to catheter arterial line attached. Samples were evaluated for hemodilution. Access to the saline roller clamp was closed while the access to the line pinch clamp was opened. The program on the apheresis machine was initiated. The return line was connected to the catheter venous line while the pinch clamps were opened and the roller clamp was closed on return saline line.

Using Venipuncture for Access:

the venipuncture sites were cleaned with chlorhexidine gluconate 2% with alcohol skin prep for about 30 seconds and air dried for approximately 30 seconds. The access venipuncture was performed using a 17 gauge needle attached to spectra access line or 18 gauge needle from stock supply. Lab specimens were drawn for possibility of hemodilution. The return venipuncture was performed with a 20-17 g iv/needle. The spectra access and return lines were connected to access and return needles. The white pinch clamps were opened on access and return lines. The roller clamp was adjusted on the return saline line to keep vein open, to prevent return needle from clotting if there would be a delay in returning through needle. Acces to the access saline roller clamp was closed and pressure in the cuff inflated to 40 mm hg prior to continuing to the start run mode.

Specifications:

mononuclear cells were collected using procedures at an hct of 2-4% on the colorgram (very light, 0.5-1.5% for products which will undergo secondary processing e.g. Isolex or clinimacs). The colorgram was inserted under the smallest clear collect line where it exits the centrifuge chamber, just below the multi-lumen connector. The colored rectangles on the colorgram to the color of the collect line were compared. Mononuclear cell collections should have a minimum number of red cells. Typically, there was a significant number of white blood cells in the top layer of the red blood cells. It was necessary to collect some red blood cells for a maximum mononuclear cell yield. However, if the product is to be further processed for cell selection, granulocytes will compete with the CD34+ cells in the CD34+ selection instruments. The lighter the collection, fewer granulocytes but more platelets were collected. If the color of the collect line is too dark, the plasma pump flow rate was decreased by 0.3 to 1 ml/minute every 3-5 minutes. If the color of the collect line is too light, the plasma pump flow rate was increased by the same adjustment.

Plasma was collected after quick start completed until the end of the target run time. Collecting plasma may cause temporary interface instability and high return pressure alarms. In order to avid this, plasma was collected by opening the slide clamp on the plasma line, pressing the target values, pressing plasma, entering the volume of plasma to collect and pressing enter. Near the end of plasma collection, the rate was slowed to 30-40 ml/min, as the return pressure limit allows, and then gradually increased to the previous rate.

For cryopreserved products: if the white blood cell count is greater or equal to 30 k/ul and platelet count is greater or equal to 30 k/ul on patients, or 200 k/ul on donors, the collect rate is increased to make product bag contain a minimum of 300 ml.

The slide clamp was closed above the frangible on the accessory line and the frangible completely broken by bending the tubing containing the frangible back and forth. Aseptic technique was used to remove the cap from the leer connection below the sterile barrier filter and a syringe containing the desired amount of anticoagulant was attached. The slide clamp above the frangible was opened and the anticoagulant slowly injected through the sterile barrier filter into the product bag. The slide clamp on the tubing just above the frangible was closed before removing the syringe to prevent back flow of fluid. A syringe containing approximately 3 ml of preservative free saline was attached to the luer connection below the sterile barrier filter. The slide clamp was opened above the frangible and the saline injected through the sterile barrier filter to flush the anticoagulant into the product bag. The slide clamp on the tubing was opened just above the frangible and cap replaced.

A midbag sample was obtained by closing the slide clamp between the product bag and the y connector on the bulb assembly and the slide clamp on the tubing between one of the sample bulbs and the y connector. The product bag was mixed well to ensure a representative sample and the slide clamp opened between the product bag and the y connector on the sample bulb assembly. The sample bulb attached to the tubing was squeezed with the open slide clamp to withdraw only the amount of product sample needed. If too much product sample was withdrawn, the excess product sample was expressed back into the product bag by inverting the sample bulb above the fluid level of the product bag, squeezing the sample bulb to express excess product sample back into the product bag and clearing the tubing of product sample using residual air, by holding the sample bulb upright and below the product bag, squeezing the sample bulb using residual air in the sample bulb to push product sample from the tubing into the product bag and while maintaining pressure on the sample bulb, closing the slide clamp just below the y connector.

The product sample was aspirated from the sampling port with a blunt 18 gauge 1 inch needle and a syringe by inserting a blunt needle with attached syringe into the sampling port, inverting the sample bulb, slowly aspirate the product sample into the syringe, removing the needle with attached syringe from the sampling port and transferring the product sample to test tube.

Rinseback

Start Rinseback Using Catheter for Access:

the roller clamp on green saline line was opened and the access catheter flushed with 10 ml of saline, then the white pinch clamp on access line was closed. The return line was flushed with 10 ml of saline and the white pinch clamp on return line was closed. The roller clamps on saline lines were closed and the connection sites cleaned with alcohol. The catheter was clamped and the access line closed before attaching a new needleless connector pre-filled with heparin. The lumen was flushed with 3 ml, 100 units/ml heparin and the syringe and reclamp catheter were removed. The same procedure was repeated for the return line.

Start Rinseback Using Venipunctures for Access:

the pressure on cuff was released and the roller clamp on green saline line opened tto flush needle, then the white pinch clamp on access line closed. The draw line needle was removed. The white pinch clamp on return line was closed and the return needle removed. Pressure was applied to the venipuncture site, and the roller clamps on saline lines closed.

Example 4—Isolation and Purification of CD34+ Cells from Apheresis Products

The CliniMACS system was used for the selection and enrichment of CD34+ hematopoietic progenitor cells (HPC). The CliniMACS system employs CD34 antibodies conjugated to magnetic particles as a means of labeling the target progenitor cells. Once labeled with these magnetic particles, the cell suspension was passed through strong magnetic gradients within the selection column on the CliniMACS device. The magnetically-labeled CD34+ cells were retained within the column while unlabeled cells flowed through the column and were collected in the Reduced Fraction bag. When the column was removed from the magnetic field, the CD34 positive cells are released for collection in the Enriched Fraction bag.

Reagent Preparation

TABLE 3

| Solution | Reagents | Volume | Final Concentration | Storage |
|---|---|---|---|---|
| CliniMACS Buffer | PBS Buffer Containing 1 mM EDTA pH 7.2 25% HSA | 1 L 20 ml | 0.5% HSA in CliniMACS Buffer | 1 bag COBE 1 bag CliniMACS 1 bag BSC/COBE |
| HSA/Normosol Formulation Media | Normosol 25% HSA | 46 ml 4 ml | 2% HSA/Normosol | 4C Fridge |
| Cryoprotectant Media | Hetastarch 25% HSA DMSO | 12.2 ml 4.8 ml 3 ml | 1.8% HES 2.5% HSA 7.5% DMSO | 4C Fridge |

Product Preparation

A settle plate was placed on each side of the biosafety cabinet and product brought into the cabinet. For HPC-Apheresis products test was performed on each product prior to pooling. A 3-way sampling transfer set was inserted into the bag. For products that will be stored in the refrigerator overnight, autologous donor plasma was added to yield a cell concentration of <200×10E6/ml. On the following morning, the product equilibrated at room temperature before processing to prevent clumping.

The cells were transferred from the apheresis collection bag to the 600 ml transfer pack labeled as "cell preparation" (heat seal leaving 6-8 inches of transfer pack tubing for sterile docking later). The product was weighted and the product volume calculated.

Removal of Excess Plasma when Product is >200 ml:

the product was balanced and centrifuged at 250 g for 15 minutes with no brake at room temperature. A sterile product bag was docked to the 600 ml transfer pack labeled "waste plasma" and tubing clamped with a hemostat. The product bag was removed from the centrifuge bucket to avoid disturbing the cell sediment and hung on the plasma extractor. The plasma extractor handle was used, the hemostat opened and plasma expressed into the waste bag. The tubing was clamped with the hemostat to stop the flow. The cell bag was removed from the plasma extractor and the cell pellet resuspended. The cells were placed on the tared scale and both air and plasma expressed back into the cell bag until bag volume was <200 ml. The hemostat was closed and cell pellet resuspended in the cell preparation bag by gently swirling the bag. Proceed to Platelet Wash.

Platelet Wash when Product is <200 ml:

A plasma transfer set was attached to one of the prepared buffer bags and the tubing of the transfer set was sterily docked to the cell bag. The roller clamp was opened and the Cell Preparation bag filled with buffer. The tubing between the Cell Preparation bag and the buffer bag was heat sealed with 6-8 inches of room. The remainder of the buffer bag was retained for Removal of Excess Reagent. The centrifuge was balanced and bags centrifuged at 250 g for 15 minutes at room temperature, no brake. The product bag was sterily docked to the 600 ml transfer pack labeled "Platelet Waste" and tubing clamped with a hemostat. The product bag was hung on plasma extractor pins and plasma released from the plasma extractor handle, the hemostat opened and plasma expressed into the waste bag. The tubing was clamped with a hemostat to stop the flow and the cell bag removed from plasma extractor and cells resuspended. The product bag was placed on a tared scale and adjusted to the appropriate antibody incubation weight (see CD34 reagent weight parameter table below). The total nucleated cell and/or CD34+ cell content and product and reagent volumes were within the specified ranges for optimal labeling of the cells.

TABLE 4

| TNC and CD34 limitations | <60 × 10$^9$ TNC or <600 × 10$^6$ CD34 | >60 × 10$^9$ TNC or >600 × 10$^6$ CD34 |
|---|---|---|
| Incubation Weight | 95 g (90-100 g) | 190 g (180-200 g) |
| CliniMACS CD34 Reagent | 1 vial (7.5 ml) | 2 vials (15.0 ml) |

CliniMACS Set-Up

The tubing set was prepared inside the biological safety cabinet and the "CD34 Enriched" collection bag: heat sealed. 150 ml was removed from a transfer bag and a recipient bag attached, the blue pin inserted and connected to the CliniMACS luer connector. A Pall filter was inserted via the blunt end to the CliniMACS bubble trap spike. The CliniMACS device was powered on and self-diagnostic procedures run.

Priming

The CliniMACS system automatically primed once the program was initiated. Buffer circulated through the tubing set and collected in both the priming waste bag and buffer waste bags.

CD34 Reagent Labeling

The total cell number was counted and required number of vial(s) of CD34 Reagent added to the product bag based on the total number of cells collected. The contents of the cell preparation bag were mixed thoroughly using a gentle end-over-end motion at 5-10 minute intervals or the bag was placed on a rocker at 25 rpm and angle 10% for 30 minutes.

Excess reagent was removed by repeating the steps in the "platelet wash section" except that two transfer bags were labeled, one 'Reagent Wash 1' and one 'Reagent Wash 2', to substitute Platelet Waste bags. CliniMACS Buffer was added and the wash performed. The product was weighted on a tared scale and product weight adjusted to the The Start Product weight range of between 80 g and 318 g.

CD34 Selection

A Start Product Bag was connected to the CliniMACS and the cap from the top of the Pall filter was removed to spike the Start Product bag. The Start Product bag was placed on the center hanger bar and the CD34+ selection procedure initiated by pressing RUN on the CliniMACS. The selection process is automated and lasted about 40 minutes.

Cell Formulation

A sample from the Reduced Fraction Bag was taken to determine cell count, viability, sterility, and perform FACS assays for CD3+ cell counts.

Cryopreservation

The centrifuge was pre-cooled to 4° C. and a sample from the CD34 Enriched Fraction Bag taken to determine cell counts, viability, any colony forming units, and flow cytometry assays. The contents of the CD34 Enriched Fraction bag were transferred equally between two labeled 50 ml conical tubes. The CD34 Enriched Fraction bag was rinsed with Normosol/2% wash mixture and divided between the two tubes. Centrifuge tubes at 1700 rpm for 8 minutes, 4° C. on low brake. The supernatant was removed and transferred to a sterile waste tube(s), the pellets were resuspended by gentle tapping. The supernatant was used for a cell count, sterility and endotoxin testing.

4 ml Normosol/2% HSA was added to one of the tubes, the contents mixed and transferred to the other tube. The first tube was rinsed with 2 ml Normosol/2% HSA and transferred into the other tube, the cell volume adjusted to 7.8 ml and the cell suspension cooled in the refrigerator for 5-30 minutes.

The controlled rate freezer was prepared for a controlled rate freeze according to the manufacturer's protocols and further explained in Example 4 below. Once the controlled rate freezer was at temperature of less than −6° C., 7.8 ml of cryoprotectant solution was added to the cells. 15 ml of cell/cryoprotectant was transferred to a 50 ml cryobag and heat-sealed. The sample probe was attached to the center of the cryobag with a piece of tape and the bag positioned in the press so that the ports protruded from the top of the press. The press was closed and the labeled cassette placed into the controlled rate freezer ahead of activating the controlled rate freezer run.

Example 5—Cryopreservation of CD34+ Cells from Apheresis Products

Optimal viability of frozen therapeutic cells is achieved using cryoprotectant and a slow rate of cooling. A freezing solution using DMSO as a cryoprotectant is added to the cellular product to prevent damage to the cells caused by ice crystal formation. The CBS controlled rate freezing system consists of a freezing chamber, notebook PC equipped with Microsoft Windows operating system, Cryogenic Freezing Software, sample probe, sample racks, and $LN_2$ transfer hose. A printer has been added so that each product may have a copy of the freezing curve for its respective run, to include in the processing record. The CRF freezes at pre-defined user programmable rates. A thermocouple probe is attached to one of the cryobags or inserted into a monitor cryovial. The chamber temperature is continuously monitored. Advancement of the cryopreservation profile steps occur as a thermocouple registers pre-defined target temperatures. When the final chamber temperature specified by the profile is achieved, an alarm sounds and the product is removed and placed into a permanent storage freezer. Audible and visual alarms occur if a deviation between chamber and programmed target temperatures is detected.

Cryoprotectant Preparation

The appropriate cryoprotectant solution was prepared as described in the table below. Cryoprotectant solution was chilled for at least 30 minutes at 4-6° C. before use.

TABLE 5

| Components | Unmanipulated HPC/TC (50 or 100 ml total volume) | | Washed Products (enriched or depleted products - not containing plasma) (1 ml vial or 15 ml bag total volume) | |
|---|---|---|---|---|
| | Cell suspension:cryoprotectant ratio | | | |
| | | 70:30 Final conc. In | | 50:50 Final Conc. In |
| | Volume | product | Volume | Product |
| DMSO | 10 ml | 10% | 3 ml | 7.5% |
| Normosol | 20.4 ml | 20% | | |
| HSA (25%) | | | 4.8 ml | 4% |
| Hetastarch | | | 12.2 ml | 3% |
| Total | 30.4 ml | | 20.0 ml | |

Cryopreservation Container Selection

The appropriate cryopreservation container to use is based on cell density, product type, volume and individual protocol requirements. Per individual processing procedures, the appropriate freezing container and preparation of cell/cryoprotectant volumes was performed per the below.

TABLE 6

| Initial Product TNC | Prefreeze Volume | Freeze Mix Volume | # Freezing Bags/vials |
|---|---|---|---|
| TNC ≤ 3 × 10⁹ | 35 ml | 15 ml | 1 (250 ml) |
| TNC > 3-≤25 × 10⁹ (pediatric patients < 50 kg) | 35 ml | 15 ml | 1 (250 ml) |
| TNC > 3-50 × 10⁹ | 70 ml | 30 ml | 1 (500 ml) |
| TNC > 50-100 × 10⁹ | 140 ml | 60 ml | 2 (500 ml) |
| TNC > 100-150 × 10⁹ | 210 ml | 90 ml | 3 (500 ml) |
| TNC > 150-200 × 10⁹ | 280 ml | 120 ml | 4 (500 ml) |
| TNC > 200-250 × 10⁹ | 350 ml | 150 ml | 5 (500 ml) |
| TNC > 1-100 × 10⁶ | 0.5 ml | 0.5 | 1 ml per 1.8 ml vial |

Addition of Cryoprotectant to Product

Once the controlled rate freezer reached temperature to receive products, the freezing media was added to the product(s). An appropriate volume of cryoprotectant was added to each vial or bag according to individual processing procedures. Optimal viability was achieved when time between the addition of cryoprotectant and placement of the product into the CRF was minimized. Cryobags were heat sealed and excess tubing removed.

The bag(s) were placed in an appropriate storage cassette and each cassette placed into the controlled rate freezer. For 250-0500 ml cryobags, one of the products frozen was placed in a cassette containing the monitoring probe. The cassette prepared for the long term storage of this product was placed in the controlled rate freezer by the monitor cassette, so that the frozen product was transferred into the cold cassette at the end of the run.

Chamber Preparation

The appropriate rack was placed into the chamber, large cassette rack for products in 250-500 ml cryobags, abag press for 50 ml cryo bags or a cryovial rack for products in cryovials. For 250-500 ml cryobags a sample probe was attached to a cassette with tape so that the protruding side of the probe end was facing up and positioned such that it came in contact with the center point (fullest part) of the cryobag. For cryovials, the needle thermocouple probe was inserted through a rubber stopper to seal the monitor cryovial. For small 50 ml cryobags, a sample probe was taped directly to the center of the product before it was placed into the bad press. The sample probe connection is located on the inside of the chamber in the upper left hand corner of the fan guard. The probe was plugged into the jack and the chamber door secured.

Cryopreservation

Once the chamber reached ≤6.5° C., the product(s) prepared for cryopreservation were added to the chamber. For 250 and 500 ml bags, one of the products was placed into the cassette with the attached probe so the probe pressed against the center (fullest part) of the back of the cryobag, and closed it into the cassette. For 50 ml cryobags, the probe was attached to the center back of the bag with a piece of tape, and positioned the product in the bag press so that the ports protrude from the top of the press. The press was closed and a second 50 ml bag was placed in a second press and stacked on top if necessary. The freezing program was initiated per standard procedures.

Example 6—Thawing and Washing Cell Products

This example applies to HPC/TC products that have been collected and processed in-house or collected, processed and shipped by an outside facility for a recipient at SHC or LPCH. Upon the request of the medical and/or lab director and the attending physician, the lab will thaw and wash the cryopreserved product in the lab prior to product infusion. The thawed product is washed with Low Molecular Weight Dextrose and Albumin. Washing the product is done to remove excess hemoglobin for HPC/TC products that exceed red cell volume limitations, to reduce DMSO volume especially for small recipients (<50 kg), to remove excess plasma proteins in the allogeneic setting, and to improve the recovery of viable cells.

Reagent and Equipment Preparation—the Day Before the Infusion

The 10% LMD, ACD-A, and 5% HSA were placed in a monitored refrigerator and sufficient cold gel mats were placed in the refrigerator. The waterbath was prepared.

Reagent and Equipment Preparation—the Day of the Infusion

The water bath, BSC and processing suite were prepared and the centrifuge cooled down to 6° C. for 30 minutes. Two cold gel mats were cleaned with IPA wipes and each placed inside a sterile plastic bag. The bags were sealed and returned to the monitored refrigerator. The transport cooler and a medium sized frozen gel pack were cleaned with IPA wipes Media Preparation Thawing Media:

The tubing on the 150 ml transfer bag labeled "Thawing Media" was heat sealed and a blue dispensing pin attached to one of the ports. A blue dispensing pin was inserted into the appropriate port of the 10% LMD bag. A 60 ml syringe was used to withdraw 60 ml of 10% LMD and transferred to the Thawing Media bag. A mini-spike was inserted into the port of the 5% HSA bottle. A 60 ml syringe was used to withdraw 60 ml of 5% HSA bottle and transferred to the Thawing Media bag. A blue dispensing pin was inserted into the appropriate port of the ACD-A bag. A 12 ml syringe was used to withdraw 12 ml of ACD-A and transferred to the Thawing Media bag. The Thawing Media was mixed thoroughly.

Reconstitution Media:

The tubing on the 150 ml transfer bag labeled "Reconstitution Media" was heat sealed and a blue dispensing pin attached to one of the ports. A 60 ml syringe was used to withdraw 60 ml of 10% LMD and transferred to the Reconstitution Media bag. A 60 ml syringe was used to withdraw 60 ml of 5% HSA and transferred to the Reconstitution Media bag. Mix the Reconstitution Media thoroughly.

Product Thaw

The product was thawed only to the point that it was still "slushy"; some presence of ice is acceptable. The product bag was wiped with IPA wipes and placed inside the BSC. The product was wrapped in the cold gel mat in the BSC, the product kept chilled during the remaining processing steps.

Products Equal to or Less than 30 mls:

a Cell Wash/Infusion bag set of two bags and three tubing sections was used for these volumes. The tubing with the 2 spikes connected to the cryobag, the tubing with the blue luer adapter connected to the syringe containing the thawing media. The washed product was collected and centrifuged in the bag labeled 'Cell Wash/Infusion bag' and the supernatant was be transferred to the remaining bag. The wash/infusion set clamps were closed and the outside port covers of the cryobag with cleaned with sterile alcohol pads.

The bag was held upright and for each port, the hard part of the port was held with the thumb and forefinger of one hand. With the other hand, an infusion set spike was inserted into the disinfected port and secured. Thawing Media was sterily added to the bag by releasing the clamps on the tubing between the Thawing Media syringe and the cryobag. Half of the Thawing Media was transferred into both cryobag compartments with gentle mixing.

The clamp to the Cell Wash/Infusion bag was opened and the diluted cell suspension transferred from the cryobag into the Cell Wash/Infusion bag. The clamp on the Cell Wash/Infusion bag was closed for rinsing process. Small amounts of the remaining Thawing Media were added to rinse both compartments of the cryobag and transferred the rinse to the Cell Wash/Infusion bag. The mixture equilibrated for 5 minutes.

An aliquot of 10% LMD was added to the cryobag, the cryobag rinsed and the rinse transferred to the Cell Wash/Infusion bag. The above step was repeated until an appropriate amount of 10% LMD was dispensed into the cryobag.

The Cell Wash/Infusion bag was placed in a plastic centrifuge bag, the centrifuge balanced and the product centrifuged at 400×g for 20 minutes at 6° C. with low brake.

The bag of diluted product was placed in the plasma expressor and the supernatant slowly expressed into the attached supernatant bag, the flow rate controlled with a hemostat. A dispensing pin was inserted into one of the ports of the Cell Wash/Infusion bag and the cell pellet massaged into resuspension. Reconstitution media was added to the Cell Wash/Infusion bag and the contents thoroughly mixed.

Products Greater than 30 mls:

A dispensing pin was inserted into one of the ports of the cryobag and a syringe containing the Thawing Media was attached to the dispensing pin. Half of the Thawing Media was transferred into the cryobag, mixed, and the cryobag spiked with a 300 or 600 ml transfer pack, the contents of the cryobag transferred to the transfer pack. The cryobag was rinsed with the remaining Thawing Media and added to the transfer pack containing the cells, the mixture equilibrated for 5 minutes.

An aliquot of 10% LMD was added to the cryobag, the cryobag rinsed and the rinse transferred to the Cell Wash/Infusion bag. The above step was repeated until an appropriate amount of 10% LMD was dispensed into the cryobag.

The Cell Wash/Infusion bag was placed in a plastic centrifuge bag, the centrifuge balanced and the product centrifuged at 400×g for 20 minutes at 6° C. with low brake. The bag of diluted product was placed in the plasma expressor and the supernatant slowly expressed into the attached supernatant bag, the flow rate controlled with a hemostat. A dispensing pin was inserted into one of the ports of the Cell Wash/Infusion bag and the cell pellet massaged into resuspension. Reconstitution media was added to the Cell Wash/Infusion bag and the contents thoroughly mixed.

Post Thaw Counts

The supernatant was mixed thoroughly and a sample used for a cell count. The supernatant bag was weighted and the supernatant TNC calculated.

Cells for Infusion

Two samples were removed for analysis, 1 mL for Flow analyses and a 0.2 ml for a nucleated cell count, CFU and viability. The infusion bag was weighed and placed in a sterile plastic bag and stored in a transport cooler with frozen gel pack until infusion. Post thaw TNC and % TNC recovery were calculated and cells re-spun per table 6 below.

TABLE 7

| Supernatant NC × 10E06/ml | Infusion Cells % TNC Recovery | Re-spin Supernatant |
|---|---|---|
| ≤2 | ≥80% | no |
| ≤2 | <80% | Ask supervisor/lab director |
| >2 | <80% | yes |
| >2 | ≥80% | no |

Re-Spin the Supernate

The supernate was transferred to another transfer bag and centrifuged at 400×g for 20 min at 6° C. with low brake. The bag was then placed in the plasma expressor and a blue dispensing pin inserted into one of the ports of the bag. A luer connector was attached to the pin of the transfer bag to the dispensing pin and the expressor handle released to express off the supernatant, the flow rate controlled with the hemostat. 5 ml of each 10% LMD and 5% HSA were added to this second cell bag, the cells resuspended and the recovered cells added to the initial cell infusion bag.

A sample was removed for a nucleated cell count and viability, Flow analyses, and CFU assay from the cell infusion bag. The infusion bag was weighed, the volume calculated and recorded.

Calculations $$\% \, TNC \text{ Recovery} = \text{post thaw } TNC \text{ (cells)} \div [\text{Post thaw } TNC \text{ (cells)} + \text{supernatant } TNC] \times 100$$

$$\text{Total } CFU \text{ Count } X = \frac{TNC \times (\text{colonies counted per } 10E05 \text{ cells plated})}{10E05}$$

$$CD34 \text{ cell count}/\mu l = \frac{(NC \times 10E06/\text{ml}) \times \% \, CD34}{1000}$$

Infusion

The infusion cell bag was removed from the prepared transport cooler with frozen gel pack and the thawed product was taken to the unit.

Example 7—Hematopoietic Progenitor Cell and Therapeutic Cell Infusions from Fresh or Cryopreserved Allografts or Autografts Allograft (allogenic) transplant involves infusing donor bone marrow, hematopoietic progenitor cells (HPC) or therapeutic cells (TC) into a recipient who is genetically different. Matched or partially matched family members or unrelated donors can be used as donors. The hematopoietic cells are collected and then infused into the recipient within 24 hours. Therapeutic cells are collected and infused into the usually within 24 hours. Alternatively, hematopoietic cells maybe collected and cyropreserved.

Unrelated umbilical cord blood (UCB) is a valuable sources of donor cells for HPC transplantation, thus extending this treatment modality to patients who lack other donors.

Autograft (Autologous) transplant involves the recipient receiving his or her own bone marrow or hematopoietic progenitor cells (hpcs).

If a large volume of hpcs (more than 4 bags) are to be infused, physician may stop after half of the bags and resume transplant 1 to 2 hours later. This is to prevent circulatory overload due to the large volume of fluid infused in a short period of time. Check with physician to determine if patient should be remedicated prior to resuming transplant.

TABLE 8.1

| NURSING ACTIONS | KEY POINTS |
| --- | --- |
| Pre-administration: | |
| A. The source of the graft was determined and the method of infusion explained to the patient. The possible side effects were described and patient instructed to notify RN if any occur.<br>1. Administration checks are similar to other blood products.<br>2. Check ABO compatibility for allogeneic patients. | Urine may be pink in color for 24 hours due to culture media that was added to hpcs and/or hemolysis of red cells.<br>Pre-medication was required. If ABO incompatible, red cells must be removed from the graft. |
| B. The approximate time of the planned infusion was determined. The patient was premedicated as ordered prior to the transplant.<br>C. O$_2$ with nasal cannula and suction were setup in room. diphenhydramine (Benadryl) and furosemide (Lasix) were readily available (in the Pyxis Station). Baseline vital signs were established within one hour of infusion.<br>D. Using a primary and secondary IV tubing (no filter), the NS was connected to prime the primary tubing as the backup. Back flush to prime the secondary tubing for which the cells will infuse. A new secondary tubing for each bag of cells to be infused was obtained. | Premedications may consist of diphenhydramine (Benadryl) and hydrocortisone to minimize possible reactions.<br>In the event of an allergic reaction or fluid overload. |
| E. The large lumen of central venous catheter (CVC) was used to remove needleless connector and the IV tubing attached directly to the hub of the large lumen.<br>F. | Patency of line assessed before infusion of cells. Line must run wide open by gravity. If needed be prepared to start a peripheral IV.<br>MD injected anticoagulant into cryopreserved product to prevent cells from clotting. |
| G. The product was brought to the bedside by the MD. (This product is NOT to be irradiated or filtered.) | Cryopreserved hpcs were infused within 10-15 minutes of thawing to preserve cell viability. The cells were completely infused within 30 minutes of thawing. |

TABLE 8.2

| Administration: | |
| --- | --- |
| A. Fresh (not cryopreserved) marrow, HPC or TC:<br>1. A spike of secondary tubing was inserted into the bag of cells. The IV pump was programmed for the appropriate time and volume.<br>2. Cells were infused at 250 ml/hr.<br>3. There may be 1 or 2 bags of cells. | The second bag of cells are not released until infusion of the first bag is complete. Cell infusion length may vary due to total volume of cells<br>Monitored for signs and symptoms of an allergic reaction. |

TABLE 8.2-continued

| | |
|---|---|
| 4. Vital signs were documented 15 minutes after start of infusion. | |
| Cryopreserved HPC or TC: | |
| 1. spike of secondary tubing was inserted into the bag of cells. The IV pump was programmed for the appropriate time and volume | |
| 2. Cryopreserved cells were infused over 10 minutes. | To maintain cell viability, the cells were completely infused by 30 minutes of thawing. |
| 3. After infusing cells, the infusion tubing was rinsed and the bag emptied with a backflush of NS. The remaining cells were infused using this back flush method. | CD 34 selected cells were flushed with a syringe of 2% human serum albumin and normalsol. |
| 4. If a large volume of hpcs (more than 4 bags) are to be infused, repeat vital signs and lung assessment half, way through infusion and as clinically needed. | Large volume of fluids infused over a short period of time may cause fluid overload. Attending physcian must be in direct supervision of infusion of TC. |
| C. Cryopreserved/frozen Therapeutic cells: | |
| 1. If cells are in a small volume (e.g. Tcs), cells were be administered using a syringe by direct IV push method at catheter hub. Flush catheter before and after cell infusion with saline. | |

TABLE 8.3

| | |
|---|---|
| Post-administration: | |
| A. The patient's, respiratory status and skin were assessed for possible reactions at the end of the infusion. The vital signs were assessed again within 1 hour post infusion, C. At the end of the infusion, a new needless connector was set and then heparin-lock the central catheter. The previous solution infusion may also be resumed. | Signs and symptoms of reaction may include nausea, rigors, pulmonary emboli, shortness of breath, tachycardia, bradicardia (with frozen cells) and cardiac overload. |

What is claimed is:

1. A method of manufacturing a cellular product for establishing mixed chimerism in a solid organ transplant recipient, the method comprising:
    obtaining one or more samples comprising CD34+ cells and CD3+ cells;
    processing the one or more samples to substantially remove platelets and red blood cells; and
    further processing the one or more samples to produce a cellular product comprising greater than 5×105 CD34+ cells/kg recipient weight, and greater than 1×105 CD3+ cells/kg recipient weight, wherein the cellular product is substantially devoid of platelets and red blood cells.

2. The method of claim 1, wherein the one or more samples are further processed such that the cellular product comprises at least about 4×106 CD34+ cells/kg recipient weight.

3. The method of claim 1, wherein the one or more samples are further processed such that the cellular product comprises at least about 1×106 CD3+ cells/kg recipient weight.

4. The method of claim 1, wherein the one or more samples are further processed such that the cellular product comprises at least about 4×106 CD34+ cells/kg recipient weight and about 1×106 CD3+ cells/kg recipient weight.

5. The method of claim 1, wherein the one or more samples are further processed such that the cellular product comprises at least about 4×106 CD34+ cells/kg recipient weight and at least about 1×106 CD3+ cells/kg recipient weight.

6. The method of claim 1, wherein the cellular product is produced such that the CD34+ cells and the CD3+ cells are provided in separate containers.

7. The method of claim 1, wherein the cellular product is produced such that the CD34+ cells and the CD3+ cells are provided as a mixture in a common container.

8. The method of claim 1, wherein the CD34+ cells and the CD3+ cells are HLA matched to an HLA type of the solid organ transplant recipient.

9. The method of claim 1, wherein the CD34+ cells and the CD3+ cells are HLA mismatched to an HLA type of the solid organ transplant recipient.

10. The method of claim 1, wherein CD34+ cells and the CD3+ cells are from a single apheresis product.

* * * * *